US012758612B2

(12) United States Patent
Xiong et al.

(10) Patent No.: US 12,758,612 B2
(45) Date of Patent: Oct. 13, 2026

(54) GROWTH DIFFERENTIATION FACTOR 15 COMBINATION THERAPY

(71) Applicant: Amgen Inc., Thousand Oaks, CA (US)

(72) Inventors: YuMei Xiong, Palo Alto, CA (US); Murielle Marie Veniant Ellison, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 1323 days.

(21) Appl. No.: 17/436,696

(22) PCT Filed: Mar. 6, 2020

(86) PCT No.: PCT/US2020/021314

§ 371 (c)(1),
(2) Date: Sep. 7, 2021

(87) PCT Pub. No.: WO2020/185533

PCT Pub. Date: Sep. 17, 2020

(65) Prior Publication Data

US 2022/0152154 A1 May 19, 2022

Related U.S. Application Data

(60) Provisional application No. 62/815,866, filed on Mar. 8, 2019.

(51) Int. Cl.

| | |
|---|---|
| ***C07K 16/28*** | (2006.01) |
| ***A61K 38/18*** | (2006.01) |
| ***A61K 38/26*** | (2006.01) |
| ***A61K 39/395*** | (2006.01) |
| ***A61K 47/68*** | (2017.01) |
| ***A61P 3/04*** | (2006.01) |

(52) U.S. Cl.

CPC .......... *A61K 38/1841* (2013.01); *A61K 38/26* (2013.01); *A61K 39/3955* (2013.01); *A61K 47/6811* (2017.08); *A61P 3/04* (2018.01)

(58) Field of Classification Search

None

See application file for complete search history.

(56) References Cited

U.S. PATENT DOCUMENTS

| | | | |
|---|---|---|---|
| 3,773,919 | A | 11/1973 | Boswell et al. |
| 6,737,056 | B1 | 5/2004 | Presta |
| 7,271,149 | B2 | 9/2007 | Glaesner et al. |
| 8,338,569 | B2 | 12/2012 | Marshall et al. |
| 8,362,210 | B2 | 1/2013 | Lazar et al. |
| 8,372,952 | B2 | 2/2013 | Smith et al. |
| 8,629,244 | B2 | 1/2014 | Kolkman et al. |
| 9,161,966 | B2 | 10/2015 | Matern et al. |
| 9,248,181 | B2 | 2/2016 | De Kruif |
| 9,272,019 | B2 | 3/2016 | Shaw et al. |
| 9,550,819 | B2 | 1/2017 | Lindhout |
| 9,714,276 | B2 | 7/2017 | Xiong et al. |
| 9,827,291 | B2 | 11/2017 | Matern et al. |
| 9,828,415 | B2 | 11/2017 | Matern et al. |
| 9,834,586 | B2 | 12/2017 | Lindhout et al. |
| 9,862,752 | B2 | 1/2018 | Xiong et al. |
| 9,920,118 | B2 | 3/2018 | Shen et al. |
| 10,195,250 | B2 | 2/2019 | Lindhout et al. |
| 10,336,812 | B2 | 7/2019 | Armstrong et al. |
| 10,752,664 | B2 | 8/2020 | Xiong et al. |
| 2004/0053366 | A1 | 3/2004 | Lo et al. |
| 2006/0275283 | A1 | 12/2006 | Van Vlijmen et al. |
| 2007/0054853 | A1 | 3/2007 | Fujise et al. |
| 2009/0004181 | A1 | 1/2009 | Breit |
| 2009/0042780 | A1 | 2/2009 | Knopf et al. |
| 2010/0087627 | A1 | 4/2010 | Marshall et al. |
| 2010/0278843 | A1 | 11/2010 | Breit et al. |
| 2011/0150901 | A1 | 6/2011 | Smith et al. |
| 2011/0195067 | A1 | 8/2011 | Arnason et al. |
| 2011/0229472 | A1 | 9/2011 | Min et al. |
| 2011/0236375 | A1 | 9/2011 | Lazar et al. |
| 2013/0336981 | A1 | 12/2013 | De Kruif et al. |
| 2014/0213511 | A1 | 7/2014 | Matern et al. |
| 2015/0023960 | A1 | 1/2015 | Lindhout et al. |
| 2015/0139996 | A1 | 5/2015 | De Kruif et al. |
| 2016/0030585 | A1 | 2/2016 | Barnes et al. |
| 2016/0031960 | A1 | 2/2016 | Lindhout et al. |

(Continued)

FOREIGN PATENT DOCUMENTS

| | | | |
|---|---|---|---|
| CN | 1723220 | A | 1/2006 |
| CN | 1974601 | A | 6/2007 |

(Continued)

OTHER PUBLICATIONS

Tallarida, R. J., "Quantitative methods for assessing drug synergism" Genes Cancer. Nov. 2011;2(11):1003-8. doi: 10.1177/1947601912440575. PMID: 22737266.*

Blau et al., Lancet. Oct. 23, 2010;376(9750):1417-27. doi: 10.1016/S0140-6736(10)60961-0. PMID: 20971365.*

Abma (Blood Sugar Monitoring: When to Check and Why, 2009).

Alain et al., Therapeutic Fc-fusion proteins and peptides as successful alternatives to antibodies, MABS, 2011, 3:5, 415-416.

American Diabetes Association Standards of Medical Care in Diabetes Care—2011.

Ansel et al., Pharmaceutical Dosage Forms & Drug Delivery Systems, 7th ed. 2000.

Aulton, Pharmaceutics: The Science of Dosage Form Design, Churchill Livingstone, New York, 1988.

Ausubel et al., eds., Current Protocols in Molecular Biology, Green Publishers Inc. and Wiley and Sons, 1994.

Aronne, Treating Obesity: A New Target for Prevention of Coronary Heart Disease (Prog Cardiovasc Nurs. 2001 ; 16(3)).

Baek SJ, J. Biol Chemistry, 2001, 276:33384-33392.

(Continued)

*Primary Examiner* — Michael Szperka

(74) *Attorney, Agent, or Firm* — Amy C. Madl

(57) ABSTRACT

The present disclosure provides combination therapy with GDF15 molecules. In some embodiments, the GDF15 molecule is a GDF15-Fc fusion, in which a GDF15 region is fused to an Fc region, optionally via a linker. In one embodiment, combination therapy comprises administration of a GDF15 molecule with a GLP-1R agonist. In another embodiment, combination therapy comprises administration of a GDF15 molecule with a GIPR antagonist.

12 Claims, 13 Drawing Sheets

Specification includes a Sequence Listing.

(56) References Cited

U.S. PATENT DOCUMENTS

| | | | | |
|---|---|---|---|---|
| 2016/0120999 | A1 * | 5/2016 | Shen | A61P 3/04 435/352 |
| 2016/0129082 | A1 | 5/2016 | Matern et al. | |
| 2016/0200787 | A1 | 7/2016 | Matern et al. | |
| 2017/0107248 | A1 | 4/2017 | Lou et al. | |
| 2017/0204149 | A1 | 7/2017 | Chopra et al. | |
| 2017/0299608 | A1 | 10/2017 | Hsu et al. | |
| 2018/0079790 | A1 | 3/2018 | Xiong et al. | |
| 2019/0000923 | A1 | 1/2019 | Chutkow et al. | |
| 2019/0248852 | A1 | 8/2019 | Zhang et al. | |
| 2019/0292241 | A1 | 9/2019 | Armstrong et al. | |
| 2019/0309033 | A1 | 10/2019 | Gonciarz et al. | |

FOREIGN PATENT DOCUMENTS

| | | | | |
|---|---|---|---|---|
| EP | 0036676 | A1 | 9/1981 | |
| EP | 0036776 | A2 | 9/1981 | |
| EP | 0058481 | A1 | 8/1982 | |
| EP | 0088046 | A2 | 9/1983 | |
| EP | 0133988 | A2 | 3/1985 | |
| EP | 0143949 | B1 | 10/1988 | |
| EP | 2330197 | A2 | 6/2011 | |
| EP | 2439535 | A1 | 4/2012 | |
| EP | 2694092 | B1 | 1/2017 | |
| JP | 2003081831 | A | 3/2003 | |
| JP | 2007532586 | A | 11/2007 | |
| JP | 2010536717 | A | 12/2010 | |
| WO | 199315722 | A1 | 8/1993 | |
| WO | 199906445 | A1 | 8/2005 | |
| WO | 2005077981 | A2 | 8/2005 | |
| WO | 2005099746 | A1 | 10/2005 | |
| WO | 2006000448 | A2 | 1/2006 | |
| WO | 2007041635 | A2 | 4/2007 | |
| WO | 2009021293 | A8 | 2/2009 | |
| WO | 2009089004 | A1 | 7/2009 | |
| WO | 2009141357 | A1 | 11/2009 | |
| WO | 2010017198 | A2 | 2/2010 | |
| WO | 2010048670 | A1 | 5/2010 | |
| WO | 2011/063348 | A1 | 5/2011 | |
| WO | 2011064758 | A2 | 6/2011 | |
| WO | 2012138919 | A1 | 10/2011 | |
| WO | 2012007868 | A2 | 1/2012 | |
| WO | 2012007869 | A2 | 1/2012 | |
| WO | 2012007877 | A2 | 1/2012 | |
| WO | 2012025355 | A1 | 3/2012 | |
| WO | 2012058768 | A1 | 5/2012 | |
| WO | 2012125850 | A1 | 9/2012 | |
| WO | 2012146628 | A1 | 11/2012 | |
| WO | 2013113008 | A1 | 8/2013 | |
| WO | 2013148117 | A1 | 10/2013 | |
| WO | 2013157953 | A1 | 10/2013 | |
| WO | 2013157954 | A1 | 10/2013 | |
| WO | 2014100689 | A1 | 6/2014 | |
| WO | 2014120619 | A2 | 8/2014 | |
| WO | 2015198199 | A1 | 12/2015 | |
| WO | WO-2017112824 | A2 * | 6/2017 | A61K 38/1703 |
| WO | 2019048660 | A1 | 3/2019 | |
| WO | 2019199685 | A1 | 10/2019 | |

OTHER PUBLICATIONS

Baek SJ, Gastroenterology, 2006, 131:1553-1560.
Bauskin AR, EMBO J., 2000, 19:2212-2220; NCBI.
Beck et al., "Therapeutic Fc-fusion proteins and peptides as successful alternatives to antibodies," MABS, 3(5):415-416 (2011).
Berge et al., "Pharmaceutical Salts", J. Pharm. Science, 1977, 6661, 1-19.
Biotek (Determination of Insulin Levels in Human Serum, 2009).
Bootcov MR, 1997, Proc Natl Acad Sci 94:11514-11519.
Bottner M ,Gene, 1999, 237:105-11.
Carrillo et al., Siam J. Applied Math., 1988, 48:1073.
Cekanova M, "Nonsteroidal anti-inflammatory drug-activated gene-1 expression inhibits urethane-induced pulmonary tumorigenesis in transgenic mice", 2009, Cancer Prev Res 2:5, 450-458.
Computational Molecular Biology, Lesk, A. M., ed., 1988, New York: Oxford University Press; Biocomputing Informatics and Genome Projects, Smith, D. W., ed., 1993, New York: Academic Press.
Creative BioMart, Recombinant Human Growth Differentiation Factor 15. Fe Chimera; Oct. 23, 2010 (according to document properties for posted document); (Retrieved from the Internet Apr. 9, 2013 http://img.creativebiomart.net1pdf/GDF15-204H.GDF15 ,Fc%20Chimera. pdf>.
Czajkowsky, et al., EMBO Mol Med, Epub, 2012 4(10), 1015-1028.
Czajkowsky, et al., "Fc-fusion proteins: new developments and future perspectrives". EMBO Mol Med, Epub, 2012 4(10), 1015-1028.
Dayhoff et al., Atlas of Protein Sequence and Structure, 1978, 5:345-352.
Devereux et al., Nucl. Acid Res. 1984, 12:387.
Diabetes self-management (downloaded online from URL:<http://www.diabetesselfmanagement.com/diabetesresources/definitions/prediabetes/>, 2006).
Dinsmoor (downloaded online from URL:<http://www.diabetesselfmanagement.com/managing-diabetes/complicationsprevention/protecting-your-kidneys/, 2009).
Dostalova, et al.: Increased serum concentrations of macrophage inhibitory cytokine-1 in patients with obesity and type 2 diabetes mellitus: the influence of very low calorie diet.: European Journal of Endocrinology /European Federation of Endocrine Societies Sep. 2009, vol. 161 No. 3, (Sep. 2009), pp. 397-404.
Epstein et al., Proc. Natl. Acad. Sci. US, 1985, 82: 3688-3692.
Fairlie WD, Gene, 2000, 254: 67-76.
Freiberg & Zhu, Int. J. Pharm., 2004, 282:1-18.
GenBank: AF003934.1 (*Homo sapiens* prostate differentiation factor mRNA, complete cds, 1997).
Gribskov, M. and Devereux, J., eds., Sequence Analysis Primer, 1991, New York: M. Stockton Press.
Griffin, A. M., and Griffin, H. G., eds., Computer Analysis of Sequence Data, Part I, 1994, New Jersey: Humana Press.
Henikoff et al., Proc. Natl. Acad. Sci. USA 1992, 89:10915-10919.
Hromas R., Biochim Biophys Acta. 1997, 1354:40-44.
Inoue et al., Nat Med. Feb. 2004; 10(2):168-74.
Jenson, et al. "A novel Fc gamma receptor ligand augments humoral responses by targeting antigen to Fc gamma receptors", Eur. J. Immunol, 2007, 37:4, 1139-1148.
Johnen H, Nat Med., 2007, 11:1333-1340.
Katoh M, Int J Mol Med, 2006. 17:951-955.
Kempf T, "The Transforming Growth Factor-{szligbeta} Superfamily Member Growth-Differentiation Factor-15 Protects the Heart From Ischemia/Reperfusion Injury", Circ Res., 2006, 98:351-360.
Lajer Maria, et al.: "Plasma growth differentiation factor-15 independently predicts all-cause and cardiovascular mortality as well as deterioration of kidney function in type 1 diabetic patients with nephropathy.", Diabetes Care, vol. 33, No. 7, Jul. 2010 (Jul. 2010), pp. 1567-1572.
Langer et al., J. Biomed. Mater. Res., 1981, 15:167-277.
Langer, Chem. Tech., 1982, 12: 98-105.
Lawton LN, "Identification of a novel member of the TGF-beta superfamily highly expressed in human placenta", Gene, 1997, 203:17-26.
Lind et al.: "Growth-differentiation factor-15 is an independent marker of cardiovascular dysfunction and disease in the elderly; results from the Prospective Investigation of the Vasculature in Uppsala Seniors (PIVUS) Study", European Heart Journal (Online), Oxford University Press, GB, US, NI., vol. 30, No. 19, Oct. 1, 2009 (Oct. 1, 2009), pp. 2346-2353.
Lo et al. (2005, Protein Engineering, Design & Selection 18:1-10).
Macia L. et al., PLoS One., Apr. 13, 2012, vol. 7, No. 4, pp. e34868.
Mekhaiel, et al. "Polymeric human Fc-fusion proteins with modified effector functions", 2011, Sci Rep. 1:124.
Moore A.G., "The transforming growth factor-ss superfamily cytokine macrophage inhibitory cytokine-1 is present in high concentrations in the serum of pregnant women", J Clin Endocrinol Metab, 2006, 85: 4781-4788.
NCBI Reference Sequence: NP 004855.2 (Jan. 13, 2011).

(56) References Cited

OTHER PUBLICATIONS

Needleman et al., J. Mol. Biol., 1970, 48:443-453.
Paralkar VM, "Cloning and characterization of a novel member of the transforming growth factor-beta/bone morphogenetic protein family", J. Biol. Chemistry, 1998, 273:13760-13767.
Remington: The Science and Practice of Pharmacy, 19th edition, 1995.
Rose-John et al., "The IL-6/sIL-6R complex as a novel target for therapeutic approaches," Expert Opinion on Therapeutic Targets, 11:5, 613-624 (2007).
Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989.
Sidman et al., Biopolymers 1983, 22: 547-56.
Sino Biological Inc. (http://ww.sinobiological.com/GDF-15-Protein-g-570.html; available May 1, 2010).
Smith, D. W., ed, Biocomputing Informatics and Genome Projects, 1993, New York: Academic Press.
Strelau J, "Progressive Postnatal Motoneuron Loss in Mice Lacking GDF-15", J Neuroscience, 2009, 29:13640-13648.
Tamary H, "", Blood, 2008, 112:5241-5244.
Tanno T, "High levels of GDF15 in thalassemia suppress expression of the iron regulatory protein hepcidin", Nat Med, 2007, 13:1096-1101.
Van Heeke & Schuster, "Expression of human asparagine synthetase in *Escherichia coli*", J. Biol. Chem., 1989, 264: 5503-5509.
Von Heinje, G., Sequence Analysis in Molecular Biology, 1987, New York: Academic Press.
White, "Design and expression of polymeric immunoglobulin fusion proteins: a strategy for target in low-affinity Fogamma receptors", Protein Expr, Purif, 2001, 21:3, 446-455.
White et al., "Rapid Immune Responses to a Botulinum Neurotoxin Hc Subunit Vaccine through in Vivo Targeting to Antigen-Presenting Cells," *Infect. Immun.*, Epub, 79(8):3388-3396 (2011).
Wilson and Gisvolds' Textbook of Organic Medicinal and Pharmaceutical Chemistry, Delgado and Remers, Eds., 10th ed., 1998.
Wischke & Schwendeman, Int. J. Pharm., 2008, 364: 298-327.
Xu J, "GDF15/MIC-1 Functions As a Protective and Antihypertrophic Factor Released From the Myocardium in Association With SMAD Protein Activation", Circ Res., 2006, 98:342-350.
Zimmermann MB, "Iron metabolism in heterozygotes for hemoglobin E (HbE),—thalassemia 1, or—thalassemia and in compound heterozygotes for HbE/—thalassemia", Am J Clin Nutr, 2008, 88:1026-1031.
K. Gunasekaran et al: "Enhancing Antibody 2-24 Fc Heterodimer Formation through Electrostatic Steering Effects: Applications to Bispecific Molecules and Monovalent IgG", Journal of Biological Chemistry, vol. 285, No. 25, Jun. 18, 2010 (Jun. 18, 2010), pp. 19637-19646.
International Search Report and Written Opinion for PCT Application No. PCT/US2019/026369, mailed on Jun. 13, 2019.
Arnold, The Impact of Glycosylation on the Biological Function and Structure of Human Immunoglobulins, Annual Rev. Immunol; 25: 21-50, 2007.
Wang, IgG Fc engineering to modulate antibody effector functions; Protein Cell, 9(1): 63-73, 2018.
International Search Report and Written Opinion for PCT Application No. PCT/US2020/021314, mailed on Jun. 5, 2020.
Frikke-Schmidt et al., "GDF15 acts synergistically with liraglutide but is not necessary for weight loss induced by bariatric surgery in mice," Molecular Metabolism, vol. 21: pp. 13-21 (2019).
Killion et al., "Anti-obesity effects of GIPR antagonists alone and in combination with GLP-1R agonists in preclinical models," Sci. Transl. Med., vol. 10(472): pp. 3392 (2018).
Mullican et al., "Uniting GDF15 and GFRAL: Therapeutic Opportunities in Obesity and Beyond," Trends in Endocrinology and Metabolism, vol. 29(8): 560-570 (2018).
Patel et al., "GDF15 Provides an Endocrine Signal of Nutritional Stress in Mice and Humans," Cell Metabolism, vol. 29(3): pp. 707-718 (2019).

* cited by examiner

*p<0.05, p<0.005, *p<0.001, ****p<0.0001 by 2-way ANOVA with Dunnett's analysis in Graphpad prism.

*p<0.05, p<0.005, *p<0.001, ****p<0.0001 by 2-way ANOVA with Dunnett's analysis in Graphpad prism.

*p<0.05, p<0.005, *p<0.001, ****p<0.0001 by 2-way ANOVA with Dunnett's analysis in Graphpad prism.

*p<0.05, p<0.005, *p<0.001, ****p<0.0001 by 2-way ANOVA with Dunnett's analysis in Graphpad prism.

*p<0.05, p<0.005, *p<0.001, ****p<0.0001 by 2-way ANOVA with Dunnett's analysis in Graphpad prism.

*p<0.05, p<0.005, *p<0.001, ****p<0.0001 by 2-way ANOVA with Dunnett's analysis in Graphpad prism.

SEQUENCE LISTING

<160> NUMBER OF SEQ ID NOS: 107

<210> SEQ ID NO 1
<211> LENGTH: 927
<212> TYPE: DNA
<213> ORGANISM: Homo sapiens

<400> SEQUENCE: 1

```
atgcccgggc aagaactcag gacggtgaat ggctctcaga tgctcctggt gttgctggtg     60

ctctcgtggc tgccgcatgg gggcgccctg tctctggccg aggcgagccg cgcaagtttc    120

ccgggaccct cagagttgca ctccgaagac tccagattcc gagagttgcg gaaacgctac    180

gaggacctgc taaccaggct gcgggccaac cagagctggg aagattcgaa caccgacctc    240

gtcccggccc ctgcagtccg gatactcacg ccagaagtgc ggctgggatc cggcggccac    300

ctgcacctgc gtatctctcg ggccgccctt cccgaggggc tccccgaggc ctcccgcctt    360

caccgggctc tgttccggct gtccccgacg gcgtcaaggt cgtgggacgt gacacgaccg    420

ctgcggcgtc agctcagcct tgcaagaccc caggcgcccg cgctgcacct gcgactgtcg    480

ccgccgccgt cgcagtcgga ccaactgctg gcagaatctt cgtccgcacg gccccagctg    540

gagttgcact tgcggccgca agccgccagg gggcgccgca gagcgcgtgc gcgcaacggg    600

gaccactgtc cgctcgggcc cgggcgttgc tgccgtctgc acacggtccg cgcgtcgctg    660

gaagacctgg gctgggccga ttgggtgctg tcgccacggg aggtgcaagt gaccatgtgc    720

atcggcgcgt gcccgagcca gttccgggcg gcaaacatgc acgcgcagat caagacgagc    780

ctgcaccgcc tgaagcccga cacggtgcca gcgccctgct gcgtgcccgc cagctacaat    840

cccatggtgc tcattcaaaa gaccgacacc ggggtgtcgc tccagaccta tgatgacttg    900

ttagccaaag actgccactg catatga                                        927
```

<210> SEQ ID NO 2
<211> LENGTH: 308
<212> TYPE: PRT
<213> ORGANISM: Homo sapiens

<400> SEQUENCE: 2

```
Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160
```

```
Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285

Asp Thr Gly Val Ser Leu Gln Thr Tyr Asp Asp Leu Leu Ala Lys Asp
    290                 295                 300

Cys His Cys Ile
305


<210> SEQ ID NO 3
<211> LENGTH: 840
<212> TYPE: DNA
<213> ORGANISM: Homo sapiens

<400> SEQUENCE: 3

ctgtctctgg ccgaggcgag ccgcgcaagt ttcccgggac cctcagagtt gcactccgaa      60

gactccagat tccgagagtt gcggaaacgc tacgaggacc tgctaaccag gctgcgggcc     120

aaccagagct gggaagattc gaacaccgac ctcgtcccgg cccctgcagt ccggatactc     180

acgccagaag tgcggctggg atccggcggc cacctgcacc tgcgtatctc tcgggccgcc     240

cttcccgagg ggctccccga ggcctcccgc cttcaccggg ctctgttccg gctgtccccg     300

acggcgtcaa ggtcgtggga cgtgacacga ccgctgcggc gtcagctcag ccttgcaaga     360

ccccaggcgc ccgcgctgca cctgcgactg tcgccgccgc cgtcgcagtc ggaccaactg     420

ctggcagaat cttcgtccgc acggccccag ctggagttgc acttgcggcc gcaagccgcc     480

agggggcgcc gcagagcgcg tgcgcgcaac ggggaccact gtccgctcgg gcccgggcgt     540

tgctgccgtc tgcacacggt ccgcgcgtcg ctggaagacc tgggctgggc cgattgggtg     600

ctgtcgccac gggaggtgca agtgaccatg tgcatcggcg cgtgcccgag ccagttccgg     660

gcggcaaaca tgcacgcgca gatcaagacg agcctgcacc gcctgaagcc cgacacggtg     720

ccagcgccct gctgcgtgcc cgccagctac aatcccatgg tgctcattca aaagaccgac     780

accggggtgt cgctccagac ctatgatgac ttgttagcca aagactgcca ctgcatatga     840


<210> SEQ ID NO 4
<211> LENGTH: 279
<212> TYPE: PRT
<213> ORGANISM: Homo sapiens

<400> SEQUENCE: 4

Leu Ser Leu Ala Glu Ala Ser Arg Ala Ser Phe Pro Gly Pro Ser Glu
1               5                   10                  15

Leu His Ser Glu Asp Ser Arg Phe Arg Glu Leu Arg Lys Arg Tyr Glu
```

```
            20                  25                  30

Asp Leu Leu Thr Arg Leu Arg Ala Asn Gln Ser Trp Glu Asp Ser Asn
        35                  40                  45

Thr Asp Leu Val Pro Ala Pro Ala Val Arg Ile Leu Thr Pro Glu Val
    50                  55                  60

Arg Leu Gly Ser Gly Gly His Leu His Leu Arg Ile Ser Arg Ala Ala
65                  70                  75                  80

Leu Pro Glu Gly Leu Pro Glu Ala Ser Arg Leu His Arg Ala Leu Phe
                85                  90                  95

Arg Leu Ser Pro Thr Ala Ser Arg Ser Trp Asp Val Thr Arg Pro Leu
            100                 105                 110

Arg Arg Gln Leu Ser Leu Ala Arg Pro Gln Ala Pro Ala Leu His Leu
        115                 120                 125

Arg Leu Ser Pro Pro Pro Ser Gln Ser Asp Gln Leu Leu Ala Glu Ser
    130                 135                 140

Ser Ser Ala Arg Pro Gln Leu Glu Leu His Leu Arg Pro Gln Ala Ala
145                 150                 155                 160

Arg Gly Arg Arg Arg Ala Arg Ala Arg Asn Gly Asp His Cys Pro Leu
                165                 170                 175

Gly Pro Gly Arg Cys Cys Arg Leu His Thr Val Arg Ala Ser Leu Glu
            180                 185                 190

Asp Leu Gly Trp Ala Asp Trp Val Leu Ser Pro Arg Glu Val Gln Val
        195                 200                 205

Thr Met Cys Ile Gly Ala Cys Pro Ser Gln Phe Arg Ala Ala Asn Met
    210                 215                 220

His Ala Gln Ile Lys Thr Ser Leu His Arg Leu Lys Pro Asp Thr Val
225                 230                 235                 240

Pro Ala Pro Cys Cys Val Pro Ala Ser Tyr Asn Pro Met Val Leu Ile
                245                 250                 255

Gln Lys Thr Asp Thr Gly Val Ser Leu Gln Thr Tyr Asp Asp Leu Leu
            260                 265                 270

Ala Lys Asp Cys His Cys Ile
        275
```

<210> SEQ ID NO 5
<211> LENGTH: 339
<212> TYPE: DNA
<213> ORGANISM: Homo sapiens

<400> SEQUENCE: 5

```
gcgcgcaacg gggaccactg tccgctcggg cccgggcgtt gctgccgtct gcacacggtc     60

cgcgcgtcgc tggaagacct gggctgggcc gattgggtgc tgtcgccacg ggaggtgcaa    120

gtgaccatgt gcatcggcgc gtgcccgagc cagttccggg cggcaaacat gcacgcgcag    180

atcaagacga gcctgcaccg cctgaagccc gacacggtgc cagcgccctg ctgcgtgccc    240

gccagctaca atcccatggt gctcattcaa aagaccgaca ccggggtgtc gctccagacc    300

tatgatgact tgttagccaa agactgccac tgcatatga                           339
```

<210> SEQ ID NO 6
<211> LENGTH: 112
<212> TYPE: PRT
<213> ORGANISM: Homo sapiens

<400> SEQUENCE: 6

```
Ala Arg Asn Gly Asp His Cys Pro Leu Gly Pro Gly Arg Cys Cys Arg
```

-continued

```
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 7
<211> LENGTH: 912
<212> TYPE: DNA
<213> ORGANISM: Mus musculus

<400> SEQUENCE: 7

atggccccgc ccgcgctcca ggcccagcct ccaggcggct ctcaactgag gttcctgctg      60

ttcctgctgc tgttgctgct gctgctgtca tggccatcgc agggggacgc cctggcaatg     120

cctgaacagc gaccctccgg ccctgagtcc caactcaacg ccgacgagct acggggtcgc     180

ttccaggacc tgctgagccg gctgcatgcc aaccagagcc gagaggactc gaactcagaa     240

ccaagtcctg acccagctgt ccggatactc agtccagagg tgagattggg gtcccacggc     300

cagctgctac tccgcgtcaa ccgggcgtcg ctgagtcagg gtctccccga agcctaccgc     360

gtgcaccgag cgctgctcct gctgacgccg acggcccgcc cctgggacat cactaggccc     420

ctgaagcgtg cgctcagcct ccggggaccc cgtgctcccg cattacgcct gcgcctgacg     480

ccgcctccgg acctggctat gctgccctct ggcggcacgc agctggaact gcgcttacgg     540

gtagccgccg gcagggggcg ccgaagcgcg catgcgcacc caagagactc gtgcccactg     600

ggtccggggc gctgctgtca cttggagact gtgcaggcaa ctcttgaaga cttgggctgg     660

agcgactggg tgctgtcccc gcgccagctg cagctgagca tgtgcgtggg cgagtgtccc     720

cacctgtatc gctccgcgaa cacgcatgcg cagatcaaag cacgcctgca tggcctgcag     780

cctgacaagg tgcctgcccc gtgctgtgtc ccctccagct acaccccggt ggttcttatg     840

cacaggacag acagtggtgt gtcactgcag acttatgatg acctggtggc ccggggctgc     900

cactgcgctt ga                                                         912


<210> SEQ ID NO 8
<211> LENGTH: 303
<212> TYPE: PRT
<213> ORGANISM: Mus musculus

<400> SEQUENCE: 8

Met Ala Pro Pro Ala Leu Gln Ala Gln Pro Pro Gly Gly Ser Gln Leu
1               5                   10                  15

Arg Phe Leu Leu Phe Leu Leu Leu Leu Leu Leu Leu Leu Ser Trp Pro
            20                  25                  30

Ser Gln Gly Asp Ala Leu Ala Met Pro Glu Gln Arg Pro Ser Gly Pro
        35                  40                  45

Glu Ser Gln Leu Asn Ala Asp Glu Leu Arg Gly Arg Phe Gln Asp Leu
    50                  55                  60
```

```
Leu Ser Arg Leu His Ala Asn Gln Ser Arg Glu Asp Ser Asn Ser Glu
65                  70                  75                  80

Pro Ser Pro Asp Pro Ala Val Arg Ile Leu Ser Pro Glu Val Arg Leu
                85                  90                  95

Gly Ser His Gly Gln Leu Leu Leu Arg Val Asn Arg Ala Ser Leu Ser
            100                 105                 110

Gln Gly Leu Pro Glu Ala Tyr Arg Val His Arg Ala Leu Leu Leu Leu
        115                 120                 125

Thr Pro Thr Ala Arg Pro Trp Asp Ile Thr Arg Pro Leu Lys Arg Ala
    130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Gly Thr Gln Leu Glu
                165                 170                 175

Leu Arg Leu Arg Val Ala Ala Gly Arg Gly Arg Arg Ser Ala His Ala
            180                 185                 190

His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
    290                 295                 300


<210> SEQ ID NO 9
<211> LENGTH: 816
<212> TYPE: DNA
<213> ORGANISM: Mus musculus

<400> SEQUENCE: 9

tcgcaggggg acgccctggc aatgcctgaa cagcgaccct ccggccctga gtcccaactc      60

aacgccgacg agctacgggg tcgcttccag gacctgctga gccggctgca tgccaaccag     120

agccgagagg actcgaactc agaaccaagt cctgacccag ctgtccggat actcagtcca     180

gaggtgagat tggggtccca cggccagctg ctactccgcg tcaaccgggc gtcgctgagt     240

cagggtctcc ccgaagccta ccgcgtgcac cgagcgctgc tcctgctgac gccgacggcc     300

cgcccctggg acatcactag gcccctgaag cgtgcgctca gcctccgggg accccgtgct     360

cccgcattac gcctgcgcct gacgccgcct ccggacctgg ctatgctgcc ctctggcggc     420

acgcagctgg aactgcgctt acgggtagcc gccggcaggg ggcgccgaag cgcgcatgcg     480

cacccaagag actcgtgccc actgggtccg gggcgctgct gtcacttgga gactgtgcag     540

gcaactcttg aagacttggg ctggagcgac tgggtgctgt ccccgcgcca gctgcagctg     600

agcatgtgcg tgggcgagtg tccccacctg tatcgctccg cgaacacgca tgcgcagatc     660

aaagcacgcc tgcatggcct gcagcctgac aaggtgcctg ccccgtgctg tgtcccctcc     720

agctacaccc cggtggttct tatgcacagg acagacagtg gtgtgtcact gcagacttat     780
```

gatgacctgg tggcccgggg ctgccactgc gcttga 816

<210> SEQ ID NO 10
<211> LENGTH: 271
<212> TYPE: PRT
<213> ORGANISM: Mus musculus

<400> SEQUENCE: 10

Ser Gln Gly Asp Ala Leu Ala Met Pro Glu Gln Arg Pro Ser Gly Pro
1 5 10 15

Glu Ser Gln Leu Asn Ala Asp Glu Leu Arg Gly Arg Phe Gln Asp Leu
20 25 30

Leu Ser Arg Leu His Ala Asn Gln Ser Arg Glu Asp Ser Asn Ser Glu
35 40 45

Pro Ser Pro Asp Pro Ala Val Arg Ile Leu Ser Pro Glu Val Arg Leu
50 55 60

Gly Ser His Gly Gln Leu Leu Leu Arg Val Asn Arg Ala Ser Leu Ser
65 70 75 80

Gln Gly Leu Pro Glu Ala Tyr Arg Val His Arg Ala Leu Leu Leu Leu
85 90 95

Thr Pro Thr Ala Arg Pro Trp Asp Ile Thr Arg Pro Leu Lys Arg Ala
100 105 110

Leu Ser Leu Arg Gly Pro Arg Ala Pro Ala Leu Arg Leu Arg Leu Thr
115 120 125

Pro Pro Pro Asp Leu Ala Met Leu Pro Ser Gly Gly Thr Gln Leu Glu
130 135 140

Leu Arg Leu Arg Val Ala Ala Gly Arg Gly Arg Arg Ser Ala His Ala
145 150 155 160

His Pro Arg Asp Ser Cys Pro Leu Gly Pro Gly Arg Cys Cys His Leu
165 170 175

Glu Thr Val Gln Ala Thr Leu Glu Asp Leu Gly Trp Ser Asp Trp Val
180 185 190

Leu Ser Pro Arg Gln Leu Gln Leu Ser Met Cys Val Gly Glu Cys Pro
195 200 205

His Leu Tyr Arg Ser Ala Asn Thr His Ala Gln Ile Lys Ala Arg Leu
210 215 220

His Gly Leu Gln Pro Asp Lys Val Pro Ala Pro Cys Cys Val Pro Ser
225 230 235 240

Ser Tyr Thr Pro Val Val Leu Met His Arg Thr Asp Ser Gly Val Ser
245 250 255

Leu Gln Thr Tyr Asp Asp Leu Val Ala Arg Gly Cys His Cys Ala
260 265 270

<210> SEQ ID NO 11
<211> LENGTH: 348
<212> TYPE: DNA
<213> ORGANISM: Mus musculus

<400> SEQUENCE: 11
agcgcgcatg cgcacccaag agactcgtgc ccactgggtc cggggcgctg ctgtcacttg 60
gagactgtgc aggcaactct tgaagacttg ggctggagcg actgggtgct gtccccgcgc 120
cagctgcagc tgagcatgtg cgtgggcgag tgtccccacc tgtatcgctc cgcgaacacg 180
catgcgcaga tcaaagcacg cctgcatggc ctgcagcctg acaaggtgcc tgccccgtgc 240
tgtgtcccct ccagctacac cccggtggtt cttatgcaca ggacagacag tggtgtgtca 300
ctgcagactt atgatgacct ggtggcccgg ggctgccact gcgcttga 348

<210> SEQ ID NO 12
<211> LENGTH: 115
<212> TYPE: PRT
<213> ORGANISM: Mus musculus

<400> SEQUENCE: 12

Ser Ala His Ala His Pro Arg Asp Ser Cys Pro Leu Gly Pro Gly Arg
1 5 10 15

Cys Cys His Leu Glu Thr Val Gln Ala Thr Leu Glu Asp Leu Gly Trp
20 25 30

Ser Asp Trp Val Leu Ser Pro Arg Gln Leu Gln Leu Ser Met Cys Val
35 40 45

Gly Glu Cys Pro His Leu Tyr Arg Ser Ala Asn Thr His Ala Gln Ile
50 55 60

Lys Ala Arg Leu His Gly Leu Gln Pro Asp Lys Val Pro Ala Pro Cys
65 70 75 80

Cys Val Pro Ser Ser Tyr Thr Pro Val Val Leu Met His Arg Thr Asp
85 90 95

Ser Gly Val Ser Leu Gln Thr Tyr Asp Asp Leu Val Ala Arg Gly Cys
100 105 110

His Cys Ala
115

<210> SEQ ID NO 13
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 13

Gly Asp His Cys Pro Leu Gly Pro Gly Arg Cys Cys Arg Leu His Thr
1 5 10 15

Val Arg Ala Ser Leu Glu Asp Leu Gly Trp Ala Asp Trp Val Leu Ser
20 25 30

Pro Arg Glu Val Gln Val Thr Met Cys Ile Gly Ala Cys Pro Ser Gln
35 40 45

Phe Arg Ala Ala Asn Met His Ala Gln Ile Lys Thr Ser Leu His Arg
50 55 60

Leu Lys Pro Asp Thr Val Pro Ala Pro Cys Cys Val Pro Ala Ser Tyr
65 70 75 80

Asn Pro Met Val Leu Ile Gln Lys Thr Asp Thr Gly Val Ser Leu Gln
85 90 95

Thr Tyr Asp Asp Leu Leu Ala Lys Asp Cys His Cys Ile
100 105

<210> SEQ ID NO 14
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 14

Ala Arg Gln Gly Asp His Cys Pro Leu Gly Pro Gly Arg Cys Cys Arg
1 5 10 15

```
Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 15
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 15

Ala Arg Asp Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 16
<211> LENGTH: 112
<212> TYPE: PRT
<213> ORGANISM: Artificial Sequence
<220> FEATURE:
<223> OTHER INFORMATION: Synthetic Polyppeptide

<400> SEQUENCE: 16

Ala Arg Asn Gly Glu His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 17
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 17

Gly Glu His Cys Pro Leu Gly Pro Gly Arg Cys Cys Arg Leu His Thr
1 5 10 15

Val Arg Ala Ser Leu Glu Asp Leu Gly Trp Ala Asp Trp Val Leu Ser
20 25 30

Pro Arg Glu Val Gln Val Thr Met Cys Ile Gly Ala Cys Pro Ser Gln
35 40 45

Phe Arg Ala Ala Asn Met His Ala Gln Ile Lys Thr Ser Leu His Arg
50 55 60

Leu Lys Pro Asp Thr Val Pro Ala Pro Cys Cys Val Pro Ala Ser Tyr
65 70 75 80

Asn Pro Met Val Leu Ile Gln Lys Thr Asp Thr Gly Val Ser Leu Gln
85 90 95

Thr Tyr Asp Asp Leu Leu Ala Lys Asp Cys His Cys Ile
100 105

<210> SEQ ID NO 18
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 18

Ala Arg Gln Gly Glu His Cys Pro Leu Gly Pro Gly Arg Cys Cys Arg
1 5 10 15

Leu His Thr Val Arg Ala Ser Leu Glu Asp Leu Gly Trp Ala Asp Trp
20 25 30

Val Leu Ser Pro Arg Glu Val Gln Val Thr Met Cys Ile Gly Ala Cys
35 40 45

Pro Ser Gln Phe Arg Ala Ala Asn Met His Ala Gln Ile Lys Thr Ser
50 55 60

Leu His Arg Leu Lys Pro Asp Thr Val Pro Ala Pro Cys Cys Val Pro
65 70 75 80

Ala Ser Tyr Asn Pro Met Val Leu Ile Gln Lys Thr Asp Thr Gly Val
85 90 95

Ser Leu Gln Thr Tyr Asp Asp Leu Leu Ala Lys Asp Cys His Cys Ile
100 105 110

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Gly Gly Gly Gly Ser
1 5

<210> SEQ ID NO 20
<211> LENGTH: 10

```
<212> TYPE: PRT
<213> ORGANISM: Artificial Sequence
<220> FEATURE:
<223> OTHER INFORMATION: Synthetic Polypeptide

<400> SEQUENCE: 20

Gly Gly Gly Gly Ser Gly Gly Gly Gly Ser
1               5                   10


<210> SEQ ID NO 21
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 21

Gly Gly Gly Gly Ser Gly Gly Gly Gly Ser Gly Gly Gly Gly Ser Gly
1               5                   10                  15

Gly Gly Gly Ser
            20


<210> SEQ ID NO 22
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40


<210> SEQ ID NO 23
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 23

Gly Gly Gly Gly
1


<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Gly Gly Gly Gly Gln
1               5


<210> SEQ ID NO 25
<211> LENGTH: 20
<212> TYPE: PRT
<213> ORGANISM: Artificial Sequence
<220> FEATURE:
<223> OTHER INFORMATION: Synthetic Polypeptide
```

<400> SEQUENCE: 25

Gly Gly Gly Gly Gln Gly Gly Gly Gly Gln Gly Gly Gly Gly Gln Gly
1               5                   10                  15

Gly Gly Gly Gln
            20

<210> SEQ ID NO 26
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 26

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 27
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 27

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

```
Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215


<210> SEQ ID NO 28
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 28

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly
    210                 215


<210> SEQ ID NO 29
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 29

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly
    210


<210> SEQ ID NO 30
<211> LENGTH: 210
<212> TYPE: PRT
<213> ORGANISM: Artificial Sequence
<220> FEATURE:
<223> OTHER INFORMATION: Synthetic Polypeptides

<400> SEQUENCE: 30

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60
```

```
Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly
    210


<210> SEQ ID NO 31
<211> LENGTH: 216
<212> TYPE: PRT
<213> ORGANISM: Artificial Sequence
<220> FEATURE:
<223> OTHER INFORMATION: Synthetic Polypeptides

<400> SEQUENCE: 31

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

Lys Ser Leu Ser Leu Ser Pro Gly
    210                 215

<210> SEQ ID NO 32
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 32

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 33
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 33

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His

```
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 34
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 34

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
```

```
    210                 215


<210> SEQ ID NO 35
<211> LENGTH: 211
<212> TYPE: PRT
<213> ORGANISM: Artificial Sequence
<220> FEATURE:
<223> OTHER INFORMATION: Synthetic Polypeptide

<400> SEQUENCE: 35

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Cys Arg Lys Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Lys Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
    210


<210> SEQ ID NO 36
<211> LENGTH: 211
<212> TYPE: PRT
<213> ORGANISM: Artificial Sequence
<220> FEATURE:
<223> OTHER INFORMATION: Synthetic Polypeptide

<400> SEQUENCE: 36

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80
```

```
Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Lys Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Lys Thr Thr Pro Pro
145                 150                 155                 160

Val Leu Lys Ser Asp Gly Ser Phe Phe Leu Tyr Ser Lys Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Lys
    210


<210> SEQ ID NO 37
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 37

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 38
<211> LENGTH: 630
<212> TYPE: PRT
<213> ORGANISM: Artificial Sequence
<220> FEATURE:
<223> OTHER INFORMATION: Fusion Protein

<400> SEQUENCE: 38

```
Gly Gly Gly Glu Arg Lys Ser Ser Val Glu Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Gly Gly Gly Gly Ser Glu Arg
            260                 265                 270

Lys Ser Ser Val Glu Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Asn Ser Thr Phe Arg
            340                 345                 350

Val Val Ser Val Leu Thr Val Val His Gln Asp Trp Leu Asn Gly Lys
        355                 360                 365
```

Glu Tyr Lys Cys Lys Val Ser Asn Lys Gly Leu Pro Ala Pro Ile Glu
370 375 380

Lys Thr Ile Ser Lys Thr Lys Gly Gln Pro Arg Glu Pro Gln Val Tyr
385 390 395 400

Thr Leu Pro Pro Ser Arg Glu Glu Met Thr Lys Asn Gln Val Ser Leu
405 410 415

Thr Cys Leu Val Lys Gly Phe Tyr Pro Ser Asp Ile Ala Val Glu Trp
420 425 430

Glu Ser Asn Gly Gln Pro Glu Asn Asn Tyr Lys Thr Thr Pro Pro Met
435 440 445

Leu Asp Ser Asp Gly Ser Phe Phe Leu Tyr Ser Lys Leu Thr Val Asp
450 455 460

Lys Ser Arg Trp Gln Gln Gly Asn Val Phe Ser Cys Ser Val Met His
465 470 475 480

Glu Ala Leu His Asn His Tyr Thr Gln Lys Ser Leu Ser Leu Ser Pro
485 490 495

Gly Ser Gly Gly Gly Gly Ser Gly Gly Gly Gly Ser Gly Gly Gly Gly
500 505 510

Ser Gly Gly Gly Gly Ser Ala Arg Asn Gly Asp His Cys Pro Leu Gly
515 520 525

Pro Gly Arg Cys Cys Arg Leu His Thr Val Arg Ala Ser Leu Glu Asp
530 535 540

Leu Gly Trp Ala Asp Trp Val Leu Ser Pro Arg Glu Val Gln Val Thr
545 550 555 560

Met Cys Ile Gly Ala Cys Pro Ser Gln Phe Arg Ala Ala Asn Met His
565 570 575

Ala Gln Ile Lys Thr Ser Leu His Arg Leu Lys Pro Asp Thr Val Pro
580 585 590

Ala Pro Cys Cys Val Pro Ala Ser Tyr Asn Pro Met Val Leu Ile Gln
595 600 605

Lys Thr Asp Thr Gly Val Ser Leu Gln Thr Tyr Asp Asp Leu Leu Ala
610 615 620

Lys Asp Cys His Cys Ile
625 630

<210> SEQ ID NO 39
<211> LENGTH: 348
<212> TYPE: PRT
<213> ORGANISM: Artificial Sequence
<220> FEATURE:
<223> OTHER INFORMATION: Fusion Protein

<400> SEQUENCE: 39

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

```
Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Gly Ser Gly Gly Gly
    210                 215                 220

Gly Ser Gly Gly Gly Gly Ser Gly Gly Gly Gly Ser Ala Arg Asn Gly
225                 230                 235                 240

Asp His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
            340                 345


<210> SEQ ID NO 40
<211> LENGTH: 332
<212> TYPE: PRT
<213> ORGANISM: Artificial Sequence
<220> FEATURE:
<223> OTHER INFORMATION: Fusion Protein

<400> SEQUENCE: 40

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110
```

Pro Arg Glu Pro Gln Val Tyr Thr Leu Pro Pro Ser Arg Lys Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Lys Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Gly Gly Gly Gly Ala Arg Asn Gly
210 215 220

Asp His Cys Pro Leu Gly Pro Gly Arg Cys Cys Arg Leu His Thr Val
225 230 235 240

Arg Ala Ser Leu Glu Asp Leu Gly Trp Ala Asp Trp Val Leu Ser Pro
245 250 255

Arg Glu Val Gln Val Thr Met Cys Ile Gly Ala Cys Pro Ser Gln Phe
260 265 270

Arg Ala Ala Asn Met His Ala Gln Ile Lys Thr Ser Leu His Arg Leu
275 280 285

Lys Pro Asp Thr Val Pro Ala Pro Cys Cys Val Pro Ala Ser Tyr Asn
290 295 300

Pro Met Val Leu Ile Gln Lys Thr Asp Thr Gly Val Ser Leu Gln Thr
305 310 315 320

Tyr Asp Asp Leu Leu Ala Lys Asp Cys His Cys Ile
325 330

<210> SEQ ID NO 41
<211> LENGTH: 325
<212> TYPE: PRT
<213> ORGANISM: Artificial Sequence
<220> FEATURE:
<223> OTHER INFORMATION: Fusion Protein

<400> SEQUENCE: 41

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

```
Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Asp His Cys Pro Leu Gly Pro
    210                 215                 220

Gly Arg Cys Cys Arg Leu His Thr Val Arg Ala Ser Leu Glu Asp Leu
225                 230                 235                 240

Gly Trp Ala Asp Trp Val Leu Ser Pro Arg Glu Val Gln Val Thr Met
                245                 250                 255

Cys Ile Gly Ala Cys Pro Ser Gln Phe Arg Ala Ala Asn Met His Ala
            260                 265                 270

Gln Ile Lys Thr Ser Leu His Arg Leu Lys Pro Asp Thr Val Pro Ala
        275                 280                 285

Pro Cys Cys Val Pro Ala Ser Tyr Asn Pro Met Val Leu Ile Gln Lys
    290                 295                 300

Thr Asp Thr Gly Val Ser Leu Gln Thr Tyr Asp Asp Leu Leu Ala Lys
305                 310                 315                 320

Asp Cys His Cys Ile
                325


<210> SEQ ID NO 42
<211> LENGTH: 328
<212> TYPE: PRT
<213> ORGANISM: Artificial Sequence
<220> FEATURE:
<223> OTHER INFORMATION: Fusion Protein

<400> SEQUENCE: 42

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175
```

```
Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Ala Arg Asp Gly Asp His Cys Pro
    210                 215                 220

Leu Gly Pro Gly Arg Cys Cys Arg Leu His Thr Val Arg Ala Ser Leu
225                 230                 235                 240

Glu Asp Leu Gly Trp Ala Asp Trp Val Leu Ser Pro Arg Glu Val Gln
                245                 250                 255

Val Thr Met Cys Ile Gly Ala Cys Pro Ser Gln Phe Arg Ala Ala Asn
            260                 265                 270

Met His Ala Gln Ile Lys Thr Ser Leu His Arg Leu Lys Pro Asp Thr
        275                 280                 285

Val Pro Ala Pro Cys Cys Val Pro Ala Ser Tyr Asn Pro Met Val Leu
    290                 295                 300

Ile Gln Lys Thr Asp Thr Gly Val Ser Leu Gln Thr Tyr Asp Asp Leu
305                 310                 315                 320

Leu Ala Lys Asp Cys His Cys Ile
                325
```

<210> SEQ ID NO 43
<211> LENGTH: 325
<212> TYPE: PRT
<213> ORGANISM: Artificial Sequence
<220> FEATURE:
<223> OTHER INFORMATION: Fusion Protein

<400> SEQUENCE: 43

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Gly Asp His Cys Pro Leu Gly Pro
    210                 215                 220

Gly Arg Cys Cys Arg Leu His Thr Val Arg Ala Ser Leu Glu Asp Leu
225                 230                 235                 240

Gly Trp Ala Asp Trp Val Leu Ser Pro Arg Glu Val Gln Val Thr Met
                245                 250                 255

Cys Ile Gly Ala Cys Pro Ser Gln Phe Arg Ala Ala Asn Met His Ala
            260                 265                 270

Gln Ile Lys Thr Ser Leu His Arg Leu Lys Pro Asp Thr Val Pro Ala
        275                 280                 285

Pro Cys Cys Val Pro Ala Ser Tyr Asn Pro Met Val Leu Ile Gln Lys
    290                 295                 300

Thr Asp Thr Gly Val Ser Leu Gln Thr Tyr Asp Asp Leu Leu Ala Lys
305                 310                 315                 320

Asp Cys His Cys Ile
                325


<210> SEQ ID NO 44
<211> LENGTH: 328
<212> TYPE: PRT
<213> ORGANISM: Artificial Sequence
<220> FEATURE:
<223> OTHER INFORMATION: Fusion Protein

<400> SEQUENCE: 44

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Ala Arg Asp Gly Asp His Cys Pro
    210                 215                 220

Leu Gly Pro Gly Arg Cys Cys Arg Leu His Thr Val Arg Ala Ser Leu
225                 230                 235                 240
```

```
Glu Asp Leu Gly Trp Ala Asp Trp Val Leu Ser Pro Arg Glu Val Gln
                245                 250                 255

Val Thr Met Cys Ile Gly Ala Cys Pro Ser Gln Phe Arg Ala Ala Asn
            260                 265                 270

Met His Ala Gln Ile Lys Thr Ser Leu His Arg Leu Lys Pro Asp Thr
        275                 280                 285

Val Pro Ala Pro Cys Cys Val Pro Ala Ser Tyr Asn Pro Met Val Leu
    290                 295                 300

Ile Gln Lys Thr Asp Thr Gly Val Ser Leu Gln Thr Tyr Asp Asp Leu
305                 310                 315                 320

Leu Ala Lys Asp Cys His Cys Ile
                325


<210> SEQ ID NO 45
<211> LENGTH: 319
<212> TYPE: PRT
<213> ORGANISM: Artificial Sequence
<220> FEATURE:
<223> OTHER INFORMATION: Fusion Protein

<400> SEQUENCE: 45

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Glu His Cys Pro Leu Gly Pro Gly Arg Cys Cys Arg Leu
    210                 215                 220

His Thr Val Arg Ala Ser Leu Glu Asp Leu Gly Trp Ala Asp Trp Val
225                 230                 235                 240

Leu Ser Pro Arg Glu Val Gln Val Thr Met Cys Ile Gly Ala Cys Pro
                245                 250                 255

Ser Gln Phe Arg Ala Ala Asn Met His Ala Gln Ile Lys Thr Ser Leu
            260                 265                 270
```

His Arg Leu Lys Pro Asp Thr Val Pro Ala Pro Cys Cys Val Pro Ala
275 280 285

Ser Tyr Asn Pro Met Val Leu Ile Gln Lys Thr Asp Thr Gly Val Ser
290 295 300

Leu Gln Thr Tyr Asp Asp Leu Leu Ala Lys Asp Cys His Cys Ile
305 310 315

<210> SEQ ID NO 46
<211> LENGTH: 322
<212> TYPE: PRT
<213> ORGANISM: Artificial Sequence
<220> FEATURE:
<223> OTHER INFORMATION: Fusion Protein

<400> SEQUENCE: 46

Gly Pro Ser Val Phe Leu Phe Pro Pro Lys Pro Lys Asp Thr Leu Met
1 5 10 15

Ile Ser Arg Thr Pro Glu Val Thr Cys Val Val Val Asp Val Ser His
20 25 30

Glu Asp Pro Glu Val Lys Phe Asn Trp Tyr Val Asp Gly Val Glu Val
35 40 45

His Asn Ala Lys Thr Lys Pro Arg Glu Glu Gln Tyr Asn Ser Thr Tyr
50 55 60

Arg Val Val Ser Val Leu Thr Val Leu His Gln Asp Trp Leu Asn Gly
65 70 75 80

Lys Glu Tyr Lys Cys Lys Val Ser Asn Lys Ala Leu Pro Ala Pro Ile
85 90 95

Glu Lys Thr Ile Ser Lys Ala Lys Gly Gln Pro Arg Glu Pro Gln Val
100 105 110

Cys Thr Leu Pro Pro Ser Arg Glu Glu Met Thr Lys Asn Gln Val Ser
115 120 125

Leu Thr Cys Leu Val Lys Gly Phe Tyr Pro Ser Asp Ile Ala Val Glu
130 135 140

Trp Glu Ser Asn Gly Gln Pro Glu Asn Asn Tyr Asp Thr Thr Pro Pro
145 150 155 160

Val Leu Asp Ser Asp Gly Ser Phe Phe Leu Tyr Ser Asp Leu Thr Val
165 170 175

Asp Lys Ser Arg Trp Gln Gln Gly Asn Val Phe Ser Cys Ser Val Met
180 185 190

His Glu Ala Leu His Asn His Tyr Thr Gln Lys Ser Leu Ser Leu Ser
195 200 205

Pro Gly Ala Arg Gln Gly Glu His Cys Pro Leu Gly Pro Gly Arg Cys
210 215 220

Cys Arg Leu His Thr Val Arg Ala Ser Leu Glu Asp Leu Gly Trp Ala
225 230 235 240

Asp Trp Val Leu Ser Pro Arg Glu Val Gln Val Thr Met Cys Ile Gly
245 250 255

Ala Cys Pro Ser Gln Phe Arg Ala Ala Asn Met His Ala Gln Ile Lys
260 265 270

Thr Ser Leu His Arg Leu Lys Pro Asp Thr Val Pro Ala Pro Cys Cys
275 280 285

Val Pro Ala Ser Tyr Asn Pro Met Val Leu Ile Gln Lys Thr Asp Thr
290 295 300

Gly Val Ser Leu Gln Thr Tyr Asp Asp Leu Leu Ala Lys Asp Cys His
305 310 315 320

Cys Ile

<210> SEQ ID NO 47
<211> LENGTH: 322
<212> TYPE: PRT
<213> ORGANISM: Artificial Sequence
<220> FEATURE:
<223> OTHER INFORMATION: Fusion Protein

<400> SEQUENCE: 47

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Glu His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
        275                 280                 285

Val Pro Ala Ser Tyr Asn Pro Met Val Leu Ile Gln Lys Thr Asp Thr
    290                 295                 300

Gly Val Ser Leu Gln Thr Tyr Asp Asp Leu Leu Ala Lys Asp Cys His
305                 310                 315                 320

Cys Ile
```

<210> SEQ ID NO 48
<211> LENGTH: 342
<212> TYPE: PRT
<213> ORGANISM: Artificial Sequence
<220> FEATURE:
<223> OTHER INFORMATION: Fusion Protein

<400> SEQUENCE: 48

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Gln Gly Gly Gly Gly Gln Gly Gly Gly Gly
    210                 215                 220

Gln Gly Gly Gly Gly Gln Ala Arg Asn Gly Asp His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340

<210> SEQ ID NO 49
<211> LENGTH: 342
<212> TYPE: PRT
<213> ORGANISM: Artificial Sequence
<220> FEATURE:
<223> OTHER INFORMATION: Fusion Protein

<400> SEQUENCE: 49

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Gln Gly Gly Gly Gly Gln Gly Gly Gly Gly
    210                 215                 220

Gln Gly Gly Gly Gly Gln Ala Arg Gln Gly Asp His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340
```

<210> SEQ ID NO 50
<211> LENGTH: 342
<212> TYPE: PRT
<213> ORGANISM: Artificial Sequence
<220> FEATURE:
<223> OTHER INFORMATION: Fusion Protein

<400> SEQUENCE: 50

```
Gly Pro Ser Val Phe Leu Phe Pro Pro Lys Pro Lys Asp Thr Leu Met
```

```
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Gln Gly Gly Gly Gly Gln Gly Gly Gly Gly
    210                 215                 220

Gln Gly Gly Gly Gly Gln Ala Arg Gln Gly Glu His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340


<210> SEQ ID NO 51
<211> LENGTH: 332
<212> TYPE: PRT
<213> ORGANISM: Artificial Sequence
<220> FEATURE:
<223> OTHER INFORMATION: Fusion Protein

<400> SEQUENCE: 51

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
```

```
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Ser Gly Gly Gly Gly Ser Ala Arg Gln Gly
    210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330


<210> SEQ ID NO 52
<211> LENGTH: 332
<212> TYPE: PRT
<213> ORGANISM: Artificial Sequence
<220> FEATURE:
<223> OTHER INFORMATION: Fusion Protein

<400> SEQUENCE: 52

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
```

```
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Ser Gly Gly Gly Gly Ser Ala Arg Gln Gly
    210                 215                 220

Glu His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330


<210> SEQ ID NO 53
<211> LENGTH: 327
<212> TYPE: PRT
<213> ORGANISM: Artificial Sequence
<220> FEATURE:
<223> OTHER INFORMATION: Fusion Protein

<400> SEQUENCE: 53

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
```

```
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Ser Ala Arg Gln Gly Asp His Cys Pro Leu
    210                 215                 220

Gly Pro Gly Arg Cys Cys Arg Leu His Thr Val Arg Ala Ser Leu Glu
225                 230                 235                 240

Asp Leu Gly Trp Ala Asp Trp Val Leu Ser Pro Arg Glu Val Gln Val
                245                 250                 255

Thr Met Cys Ile Gly Ala Cys Pro Ser Gln Phe Arg Ala Ala Asn Met
            260                 265                 270

His Ala Gln Ile Lys Thr Ser Leu His Arg Leu Lys Pro Asp Thr Val
        275                 280                 285

Pro Ala Pro Cys Cys Val Pro Ala Ser Tyr Asn Pro Met Val Leu Ile
    290                 295                 300

Gln Lys Thr Asp Thr Gly Val Ser Leu Gln Thr Tyr Asp Asp Leu Leu
305                 310                 315                 320

Ala Lys Asp Cys His Cys Ile
                325


<210> SEQ ID NO 54
<211> LENGTH: 327
<212> TYPE: PRT
<213> ORGANISM: Artificial Sequence
<220> FEATURE:
<223> OTHER INFORMATION: Fusion Protein

<400> SEQUENCE: 54

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
```

```
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Ser Ala Arg Gln Gly Glu His Cys Pro Leu
    210                 215                 220

Gly Pro Gly Arg Cys Cys Arg Leu His Thr Val Arg Ala Ser Leu Glu
225                 230                 235                 240

Asp Leu Gly Trp Ala Asp Trp Val Leu Ser Pro Arg Glu Val Gln Val
                245                 250                 255

Thr Met Cys Ile Gly Ala Cys Pro Ser Gln Phe Arg Ala Ala Asn Met
            260                 265                 270

His Ala Gln Ile Lys Thr Ser Leu His Arg Leu Lys Pro Asp Thr Val
        275                 280                 285

Pro Ala Pro Cys Cys Val Pro Ala Ser Tyr Asn Pro Met Val Leu Ile
    290                 295                 300

Gln Lys Thr Asp Thr Gly Val Ser Leu Gln Thr Tyr Asp Asp Leu Leu
305                 310                 315                 320

Ala Lys Asp Cys His Cys Ile
                325


<210> SEQ ID NO 55
<211> LENGTH: 322
<212> TYPE: PRT
<213> ORGANISM: Artificial Sequence
<220> FEATURE:
<223> OTHER INFORMATION: Fusion Protein

<400> SEQUENCE: 55

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
```

```
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Asp His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
        275                 280                 285

Val Pro Ala Ser Tyr Asn Pro Met Val Leu Ile Gln Lys Thr Asp Thr
    290                 295                 300

Gly Val Ser Leu Gln Thr Tyr Asp Asp Leu Leu Ala Lys Asp Cys His
305                 310                 315                 320

Cys Ile


<210> SEQ ID NO 56
<211> LENGTH: 348
<212> TYPE: PRT
<213> ORGANISM: Artificial Sequence
<220> FEATURE:
<223> OTHER INFORMATION: Fusion Protein

<400> SEQUENCE: 56

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190
```

```
Phe Ser Cys Ser Val Met His Glu Ala Leu His Asn His Tyr Thr Gln
        195                 200                 205

Lys Ser Leu Ser Leu Ser Pro Gly Gly Gly Gly Gly Gln Gly Gly Gly
    210                 215                 220

Gly Gln Gly Gly Gly Gly Gln Gly Gly Gly Gly Gln Ala Arg Gln Gly
225                 230                 235                 240

Asp His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
            340                 345
```

<210> SEQ ID NO 57
<211> LENGTH: 348
<212> TYPE: PRT
<213> ORGANISM: Artificial Sequence
<220> FEATURE:
<223> OTHER INFORMATION: Fusion Protein

<400> SEQUENCE: 57

```
Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205
```

```
Lys Ser Leu Ser Leu Ser Pro Gly Gly Gly Gly Gly Gln Gly Gly Gly
    210                 215                 220

Gly Gln Gly Gly Gly Gly Gln Gly Gly Gly Gly Gln Ala Arg Gln Gly
225                 230                 235                 240

Glu His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
            340                 345
```

<210> SEQ ID NO 58
<211> LENGTH: 41
<212> TYPE: PRT
<213> ORGANISM: Heloderma horridum

<400> SEQUENCE: 58

```
His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Asn His
        35                  40
```

<210> SEQ ID NO 59
<211> LENGTH: 41
<212> TYPE: PRT
<213> ORGANISM: Heloderma suspectum

<400> SEQUENCE: 59

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Asn His
        35                  40
```

<210> SEQ ID NO 60
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 60

```
His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

<210> SEQ ID NO 61
<211> LENGTH: 275
<212> TYPE: PRT
<213> ORGANISM: Artificial Sequence
<220> FEATURE:
<223> OTHER INFORMATION: Synthetic Polypeptide

<400> SEQUENCE: 61

His Gly Glu Gly Thr Phe Thr Ser Asp Val Ser Ser Tyr Leu Glu Glu
1 5 10 15

Gln Ala Ala Lys Glu Phe Ile Ala Trp Leu Val Lys Gly Gly Gly Gly
20 25 30

Gly Gly Gly Ser Gly Gly Gly Gly Ser Gly Gly Gly Gly Ser Ala Glu
35 40 45

Ser Lys Tyr Gly Pro Pro Cys Pro Pro Cys Pro Ala Pro Glu Ala Ala
50 55 60

Gly Gly Pro Ser Val Phe Leu Phe Pro Pro Lys Pro Lys Asp Thr Leu
65 70 75 80

Met Ile Ser Arg Thr Pro Glu Val Thr Cys Val Val Val Asp Val Ser
85 90 95

Gln Glu Asp Pro Glu Val Gln Phe Asn Trp Tyr Val Asp Gly Val Glu
100 105 110

Val His Asn Ala Lys Thr Lys Pro Arg Glu Glu Gln Phe Asn Ser Thr
115 120 125

Tyr Arg Val Val Ser Val Leu Thr Val Leu His Gln Asp Trp Leu Asn
130 135 140

Gly Lys Glu Tyr Lys Cys Lys Val Ser Asn Lys Gly Leu Pro Ser Ser
145 150 155 160

Ile Glu Lys Thr Ile Ser Lys Ala Lys Gly Gln Pro Arg Glu Pro Gln
165 170 175

Val Tyr Thr Leu Pro Pro Ser Gln Glu Glu Met Thr Lys Asn Gln Val
180 185 190

Ser Leu Thr Cys Leu Val Lys Gly Phe Tyr Pro Ser Asp Ile Ala Val
195 200 205

Glu Trp Glu Ser Asn Gly Gln Pro Glu Asn Asn Tyr Lys Thr Thr Pro
210 215 220

Pro Val Leu Asp Ser Asp Gly Ser Phe Phe Leu Tyr Ser Arg Leu Thr
225 230 235 240

Val Asp Lys Ser Arg Trp Gln Glu Gly Asn Val Phe Ser Cys Ser Val
245 250 255

Met His Glu Ala Leu His Asn His Tyr Thr Gln Lys Ser Leu Ser Leu
260 265 270

Ser Leu Gly
275

<210> SEQ ID NO 62
<211> LENGTH: 466
<212> TYPE: PRT
<213> ORGANISM: Artificial Sequence
<220> FEATURE:
<223> OTHER INFORMATION: Synthetic Polypeptide

<400> SEQUENCE: 62

Met Thr Thr Ser Pro Ile Leu Gln Leu Leu Leu Arg Leu Ser Leu Cys
1 5 10 15

Gly Leu Leu Leu Gln Arg Ala Glu Thr Gly Ser Lys Gly Gln Thr Ala
20 25 30

```
Gly Glu Leu Tyr Gln Arg Trp Glu Arg Tyr Arg Arg Glu Cys Gln Glu
        35                  40                  45

Thr Leu Ala Ala Ala Glu Pro Pro Ser Gly Leu Ala Cys Asn Gly Ser
    50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
    130                 135                 140

Tyr Ser Leu Ser Leu Ala Thr Leu Leu Leu Ala Leu Leu Ile Leu Ser
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
            180                 185                 190

Leu Leu Pro Arg Pro Gly Pro Tyr Leu Gly Asp Gln Ala Leu Ala Leu
        195                 200                 205

Trp Asn Gln Ala Leu Ala Ala Cys Arg Thr Ala Gln Ile Val Thr Gln
    210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
            260                 265                 270

Pro Trp Val Ile Val Arg Tyr Leu Tyr Glu Asn Thr Gln Cys Trp Glu
        275                 280                 285

Arg Asn Glu Val Lys Ala Ile Trp Trp Ile Ile Arg Thr Pro Ile Leu
    290                 295                 300

Met Thr Ile Leu Ile Asn Phe Leu Ile Phe Ile Arg Ile Leu Gly Ile
305                 310                 315                 320

Leu Leu Ser Lys Leu Arg Thr Arg Gln Met Arg Cys Arg Asp Tyr Arg
                325                 330                 335

Leu Arg Leu Ala Arg Ser Thr Leu Thr Leu Val Pro Leu Leu Gly Val
            340                 345                 350

His Glu Val Val Phe Ala Pro Val Thr Glu Glu Gln Ala Arg Gly Ala
        355                 360                 365

Leu Arg Phe Ala Lys Leu Gly Phe Glu Ile Phe Leu Ser Ser Phe Gln
    370                 375                 380

Gly Phe Leu Val Ser Val Leu Tyr Cys Phe Ile Asn Lys Glu Val Gln
385                 390                 395                 400

Ser Glu Ile Arg Arg Gly Trp His His Cys Arg Leu Arg Arg Ser Leu
                405                 410                 415

Gly Glu Glu Gln Arg Gln Leu Pro Glu Arg Ala Phe Arg Ala Leu Pro
            420                 425                 430

Ser Gly Ser Gly Pro Gly Glu Val Pro Thr Ser Arg Gly Leu Ser Ser
        435                 440                 445

Gly Thr Leu Pro Gly Pro Gly Asn Glu Ala Ser Arg Glu Leu Glu Ser
```

```
    450                 455                 460

Tyr Cys
465


<210> SEQ ID NO 63
<211> LENGTH: 430
<212> TYPE: PRT
<213> ORGANISM: Artificial Sequence
<220> FEATURE:
<223> OTHER INFORMATION: Synthetic Polypeptide

<400> SEQUENCE: 63

Met Thr Thr Ser Pro Ile Leu Gln Leu Leu Leu Arg Leu Ser Leu Cys
1               5                   10                  15

Gly Leu Leu Leu Gln Arg Ala Glu Thr Gly Ser Lys Gly Gln Thr Ala
            20                  25                  30

Gly Glu Leu Tyr Gln Arg Trp Glu Arg Tyr Arg Arg Glu Cys Gln Glu
        35                  40                  45

Thr Leu Ala Ala Ala Glu Pro Pro Ser Val Ala Ala Gly Phe Val Leu
    50                  55                  60

Arg Gln Cys Gly Ser Asp Gly Gln Trp Gly Leu Trp Arg Asp His Thr
65                  70                  75                  80

Gln Cys Glu Asn Pro Glu Lys Asn Glu Ala Phe Leu Asp Gln Arg Leu
                85                  90                  95

Ile Leu Glu Arg Leu Gln Val Met Tyr Thr Val Gly Tyr Ser Leu Ser
            100                 105                 110

Leu Ala Thr Leu Leu Leu Ala Leu Leu Ile Leu Ser Leu Phe Arg Arg
        115                 120                 125

Leu His Cys Thr Arg Asn Tyr Ile His Ile Asn Leu Phe Thr Ser Phe
    130                 135                 140

Met Leu Arg Ala Ala Ala Ile Leu Ser Arg Asp Arg Leu Leu Pro Arg
145                 150                 155                 160

Pro Gly Pro Tyr Leu Gly Asp Gln Ala Leu Ala Leu Trp Asn Gln Ala
                165                 170                 175

Leu Ala Ala Cys Arg Thr Ala Gln Ile Val Thr Gln Tyr Cys Val Gly
            180                 185                 190

Ala Asn Tyr Thr Trp Leu Leu Val Glu Gly Val Tyr Leu His Ser Leu
        195                 200                 205

Leu Val Leu Val Gly Gly Ser Glu Glu Gly His Phe Arg Tyr Tyr Leu
    210                 215                 220

Leu Leu Gly Trp Gly Ala Pro Ala Leu Phe Val Ile Pro Trp Val Ile
225                 230                 235                 240

Val Arg Tyr Leu Tyr Glu Asn Thr Gln Cys Trp Glu Arg Asn Glu Val
                245                 250                 255

Lys Ala Ile Trp Trp Ile Ile Arg Thr Pro Ile Leu Met Thr Ile Leu
            260                 265                 270

Ile Asn Phe Leu Ile Phe Ile Arg Ile Leu Gly Ile Leu Leu Ser Lys
        275                 280                 285

Leu Arg Thr Arg Gln Met Arg Cys Arg Asp Tyr Arg Leu Arg Leu Ala
    290                 295                 300

Arg Ser Thr Leu Thr Leu Val Pro Leu Leu Gly Val His Glu Val Val
305                 310                 315                 320

Phe Ala Pro Val Thr Glu Glu Gln Ala Arg Gly Ala Leu Arg Phe Ala
                325                 330                 335

Lys Leu Gly Phe Glu Ile Phe Leu Ser Ser Phe Gln Gly Phe Leu Val
```

```
            340                 345                 350

Ser Val Leu Tyr Cys Phe Ile Asn Lys Glu Val Gln Ser Glu Ile Arg
        355                 360                 365

Arg Gly Trp His His Cys Arg Leu Arg Arg Ser Leu Gly Glu Glu Gln
    370                 375                 380

Arg Gln Leu Pro Glu Arg Ala Phe Arg Ala Leu Pro Ser Gly Ser Gly
385                 390                 395                 400

Pro Gly Glu Val Pro Thr Ser Arg Gly Leu Ser Ser Gly Thr Leu Pro
                405                 410                 415

Gly Pro Gly Asn Glu Ala Ser Arg Glu Leu Glu Ser Tyr Cys
            420                 425                 430


<210> SEQ ID NO 64
<211> LENGTH: 493
<212> TYPE: PRT
<213> ORGANISM: Artificial Sequence
<220> FEATURE:
<223> OTHER INFORMATION: Synthetic Polypeptide

<400> SEQUENCE: 64

Met Thr Thr Ser Pro Ile Leu Gln Leu Leu Leu Arg Leu Ser Leu Cys
1               5                   10                  15

Gly Leu Leu Leu Gln Arg Ala Glu Thr Gly Ser Lys Gly Gln Thr Ala
            20                  25                  30

Gly Glu Leu Tyr Gln Arg Trp Glu Arg Tyr Arg Arg Glu Cys Gln Glu
        35                  40                  45

Thr Leu Ala Ala Ala Glu Pro Pro Ser Gly Leu Ala Cys Asn Gly Ser
    50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
    130                 135                 140

Tyr Ser Leu Ser Leu Ala Thr Leu Leu Leu Ala Leu Leu Ile Leu Ser
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
            180                 185                 190

Leu Leu Pro Arg Pro Gly Pro Tyr Leu Gly Asp Gln Ala Leu Ala Leu
        195                 200                 205

Trp Asn Gln Ala Leu Ala Ala Cys Arg Thr Ala Gln Ile Val Thr Gln
    210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
            260                 265                 270

Pro Trp Val Ile Val Arg Tyr Leu Tyr Glu Asn Thr Gln Cys Trp Glu
```

```
        275                 280                 285

Arg Asn Glu Val Lys Ala Ile Trp Trp Ile Ile Arg Thr Pro Ile Leu
    290                 295                 300

Met Thr Ile Leu Ile Asn Phe Leu Ile Phe Ile Arg Ile Leu Gly Ile
305                 310                 315                 320

Leu Leu Ser Lys Leu Arg Thr Arg Gln Met Arg Cys Arg Asp Tyr Arg
                325                 330                 335

Leu Arg Leu Ala Arg Ser Thr Leu Thr Leu Val Pro Leu Leu Gly Val
            340                 345                 350

His Glu Val Val Phe Ala Pro Val Thr Glu Glu Gln Ala Arg Gly Ala
        355                 360                 365

Leu Arg Phe Ala Lys Leu Gly Phe Glu Ile Phe Leu Ser Ser Phe Gln
    370                 375                 380

Gly Phe Leu Val Ser Val Leu Tyr Cys Phe Ile Asn Lys Glu Val Gly
385                 390                 395                 400

Arg Asp Pro Ala Ala Ala Pro Ala Leu Trp Arg Arg Arg Gly Thr Ala
                405                 410                 415

Pro Pro Leu Ser Ala Ile Val Ser Gln Val Gln Ser Glu Ile Arg Arg
            420                 425                 430

Gly Trp His His Cys Arg Leu Arg Arg Ser Leu Gly Glu Glu Gln Arg
        435                 440                 445

Gln Leu Pro Glu Arg Ala Phe Arg Ala Leu Pro Ser Gly Ser Gly Pro
    450                 455                 460

Gly Glu Val Pro Thr Ser Arg Gly Leu Ser Ser Gly Thr Leu Pro Gly
465                 470                 475                 480

Pro Gly Asn Glu Ala Ser Arg Glu Leu Glu Ser Tyr Cys
                485                 490


<210> SEQ ID NO 65
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 65

Arg Ala Ser Gln Ser Val Ser Ser Asn Leu Ala
1               5                   10


<210> SEQ ID NO 66
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 66

Gly Ala Ala Thr Arg Ala Thr
1               5


<210> SEQ ID NO 67
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 67

Gln Gln Tyr Asn Asn Trp Pro Leu Thr
1               5
```

<210> SEQ ID NO 68
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 68

Ser Gly Ser Ser Ser Asn Ile Gly Ser Gln Thr Val Asn
1 5 10

<210> SEQ ID NO 69
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 69

Thr Asn Asn Gln Arg Pro Ser
1 5

<210> SEQ ID NO 70
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 70

Ala Thr Phe Asp Glu Ser Leu Ser Gly Pro Val
1 5 10

<210> SEQ ID NO 71
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 71

Arg Ala Ser Gln Asp Ile Arg Asp Tyr Leu Gly
1 5 10

<210> SEQ ID NO 72
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 72

Gly Ala Ser Ser Leu Gln Ser
1 5

<210> SEQ ID NO 73
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 73

Leu Gln His Asn Asn Tyr Pro Phe Thr
1 5

<210> SEQ ID NO 74
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 74

Arg Ala Ser Gln Gly Leu Ile Ile Trp Leu
1 5 10

<210> SEQ ID NO 75
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 75

Ala Ala Ser Ser Leu Gln Ser
1 5

<210> SEQ ID NO 76
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 76

Gln Gln Thr Asn Ser Phe Pro Pro Thr
1 5

<210> SEQ ID NO 77
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 77

Asn Tyr Gly Met His
1 5

<210> SEQ ID NO 78
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 78

Ala Ile Trp Phe Asp Ala Ser Asp Lys Tyr Tyr Ala Asp Ala Val Lys
1 5 10 15

Gly

<210> SEQ ID NO 79
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 79

Asp Gln Ala Ile Phe Gly Val Val Pro Asp Tyr
1 5 10

<210> SEQ ID NO 80
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 80

Gly Tyr Tyr Met His
1 5

<210> SEQ ID NO 81
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 81

Trp Ile Asn Pro Asn Ser Gly Gly Thr Asn Tyr Ala Gln Lys Phe Gln
1 5 10 15

Gly

<210> SEQ ID NO 82
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 82

Gly Gly Asp Tyr Val Phe Gly Thr Tyr Arg Pro His Tyr Tyr Tyr Gly
1 5 10 15

Met Asp Val

<210> SEQ ID NO 83
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 83

Tyr Phe Gly Met His
1 5

<210> SEQ ID NO 84
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 84

Val Ile Trp Tyr Asp Ala Ser Asn Lys Tyr Tyr Ala Asp Ala Val Lys
1 5 10 15

Gly

<210> SEQ ID NO 85
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 85

Asp Gly Thr Ile Phe Gly Val Leu Leu Gly Asp Tyr
1 5 10

<210> SEQ ID NO 86
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 86

Ser Tyr Tyr Trp Ser
1 5

<210> SEQ ID NO 87
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 87

Arg Ile Tyr Thr Ser Gly Ser Thr Asn Tyr Asn Pro Ser Leu Lys Ser
1 5 10 15

<210> SEQ ID NO 88
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 88

Asp Val Ala Val Ala Gly Phe Asp Tyr
1 5

<210> SEQ ID NO 89
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 89

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

Tyr Gly Ala Ala Thr Arg Ala Thr Gly Ile Pro Ala Arg Val Ser Gly
50 55 60

Ser Gly Ser Gly Thr Glu Phe Thr Leu Thr Ile Ser Ser Leu Gln Ser
65 70 75 80

Glu Asp Phe Ala Val Tyr Tyr Cys Gln Gln Tyr Asn Asn Trp Pro Leu
85 90 95

Thr Phe Gly Gly Gly Thr Lys Val Glu Ile Lys Arg
100 105

<210> SEQ ID NO 90
<211> LENGTH: 120

<212> TYPE: PRT
<213> ORGANISM: Artificial Sequence
<220> FEATURE:
<223> OTHER INFORMATION: Synthetic Polypeptide

<400> SEQUENCE: 90

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser
        115                 120
```

<210> SEQ ID NO 91
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 91

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Gln
            20                  25                  30

Thr Val Asn Trp Tyr Gln His Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Thr Phe Asp Glu Ser Leu
                85                  90                  95

Ser Gly Pro Val Phe Gly Gly Gly Thr Lys Leu Thr Val Leu Gly
            100                 105                 110
```

<210> SEQ ID NO 92
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 92

```
Gln Met Gln Val Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
```

```
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Asp Tyr Val Phe Gly Thr Tyr Arg Pro His Tyr Tyr
            100                 105                 110

Tyr Gly Met Asp Val Trp Gly Gln Gly Thr Thr Val Thr Val Ser Ser
        115                 120                 125


<210> SEQ ID NO 93
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 93

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Asp Ile Arg Asp Tyr
            20                  25                  30

Leu Gly Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Phe
                85                  90                  95

Thr Phe Gly Gln Gly Thr Lys Val Asp Ile Lys Arg
            100                 105


<210> SEQ ID NO 94
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 94

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Phe
            20                  25                  30

Gly Met His Trp Val Arg Gln Ala Pro Gly Lys Gly Leu Glu Trp Val
        35                  40                  45

Ala Val Ile Trp Tyr Asp Ala Ser Asn Lys Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ile Phe Gly Val Leu Leu Gly Asp Tyr Trp Gly
            100                 105                 110
```

```
Gln Gly Thr Leu Val Thr Val Ser Ser
        115                 120


<210> SEQ ID NO 95
<211> LENGTH: 108
<212> TYPE: PRT
<213> ORGANISM: Artificial Sequence
<220> FEATURE:
<223> OTHER INFORMATION: Synthetic Polypeptide

<400> SEQUENCE: 95

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Leu Ile Ile Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Pro
                85                  90                  95

Thr Phe Gly Gln Gly Thr Lys Val Glu Ile Lys Arg
            100                 105


<210> SEQ ID NO 96
<211> LENGTH: 117
<212> TYPE: PRT
<213> ORGANISM: Artificial Sequence
<220> FEATURE:
<223> OTHER INFORMATION: Synthetic Polypeptide

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Ile Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Asp Val Ala Val Ala Gly Phe Asp Tyr Trp Gly Gln Gly Thr Leu
            100                 105                 110

Val Thr Val Ser Ser
        115


<210> SEQ ID NO 97
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 97

Glu Ile Val Met Thr Gln Ser Pro Ala Thr Leu Ser Val Ser Pro Gly
```

```
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ala Thr Arg Ala Thr Gly Ile Pro Ala Arg Val Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 98
<211> LENGTH: 450
<212> TYPE: PRT
<213> ORGANISM: Artificial Sequence
<220> FEATURE:
<223> OTHER INFORMATION: Synthetic Polypeptide

<400> SEQUENCE: 98

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Glu Gly Leu Glu Trp Val
        35                  40                  45

Ala Ala Ile Trp Phe Asp Ala Ser Asp Lys Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Ala Ile Phe Gly Val Val Pro Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Cys Glu Glu Gln Tyr Gly Ser Thr Tyr Arg
    290                 295                 300

Cys Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 99
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 99

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Gln
            20                  25                  30

Thr Val Asn Trp Tyr Gln His Leu Pro Gly Thr Ala Pro Lys Leu Leu
        35                  40                  45

Ile Tyr Thr Asn Asn Gln Arg Pro Ser Gly Val Pro Asp Arg Phe Ser
```

```
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Phe Cys Ala Thr Phe Asp Glu Ser Leu
                85                  90                  95

Ser Gly Pro Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215


<210> SEQ ID NO 100
<211> LENGTH: 458
<212> TYPE: PRT
<213> ORGANISM: Artificial Sequence
<220> FEATURE:
<223> OTHER INFORMATION: Synthetic Polypeptide

<400> SEQUENCE: 100

Gln Met Gln Val Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Asp Tyr Val Phe Gly Thr Tyr Arg Pro His Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
```

```
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Cys Glu
    290                 295                 300

Glu Gln Tyr Gly Ser Thr Tyr Arg Cys Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 101
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 101

```
Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Asp Ile Arg Asp Tyr
            20                  25                  30

Leu Gly Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Phe
                85                  90                  95

Thr Phe Gly Gln Gly Thr Lys Val Asp Ile Lys Arg Thr Val Ala Ala
```

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 102
<211> LENGTH: 451
<212> TYPE: PRT
<213> ORGANISM: Artificial Sequence
<220> FEATURE:
<223> OTHER INFORMATION: Synthetic Polypeptide

<400> SEQUENCE: 102

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Phe
            20                  25                  30

Gly Met His Trp Val Arg Gln Ala Pro Gly Lys Gly Leu Glu Trp Val
        35                  40                  45

Ala Val Ile Trp Tyr Asp Ala Ser Asn Lys Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Ile Phe Gly Val Leu Leu Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
```

```
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Cys Glu Glu Gln Tyr Gly Ser Thr Tyr
    290                 295                 300

Arg Cys Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 103
<211> LENGTH: 214
<212> TYPE: PRT
<213> ORGANISM: Artificial Sequence
<220> FEATURE:
<223> OTHER INFORMATION: Synthetic Polypeptide

<400> SEQUENCE: 103

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Leu Ile Ile Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 104
<211> LENGTH: 447
<212> TYPE: PRT
<213> ORGANISM: Artificial Sequence
<220> FEATURE:
<223> OTHER INFORMATION: Synthetic Polypeptide

<400> SEQUENCE: 104

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
    50                  55                  60

Ser Arg Val Thr Met Ser Ile Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Asp Val Ala Val Ala Gly Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Cys Glu Glu Gln Tyr Gly Ser Thr Tyr Arg Cys Val Ser
```

```
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 105
<211> LENGTH: 239
<212> TYPE: PRT
<213> ORGANISM: Artificial Sequence
<220> FEATURE:
<223> OTHER INFORMATION: Synthetic Polypeptide

<400> SEQUENCE: 105

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asp Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Ala Asp Leu Gly Val Tyr Phe Cys
            100                 105                 110

Ser Gln Ser Thr His Val Pro Pro Phe Thr Phe Gly Gly Gly Thr Lys
        115                 120                 125

Leu Glu Ile Lys Arg Ala Asp Ala Ala Pro Thr Val Ser Ile Phe Pro
    130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
        195                 200                 205

Asp Glu Tyr Glu Arg His Asn Ser Tyr Thr Cys Glu Ala Thr His Lys
```

```
    210                 215                 220

Thr Ser Thr Ser Pro Ile Val Lys Ser Phe Asn Arg Asn Glu Cys
225                 230                 235


<210> SEQ ID NO 106
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 106

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Arg Ala Ser Gly Tyr Thr Phe
        35                  40                  45

Thr Ser Asn Trp Met His Trp Val Lys Gln Arg Pro Arg Gln Gly Leu
    50                  55                  60

Glu Trp Ile Gly Glu Ile Asn Pro Ser Asn Gly Arg Ser Asn Tyr Asn
65                  70                  75                  80

Glu Lys Phe Lys Thr Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Phe Tyr Tyr Gly Thr Ser Trp Phe Ala Tyr Trp
        115                 120                 125

Gly Gln Gly Thr Leu Val Ala Val Ser Ala Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190

Ala Val Leu Gln Ser Asp Leu Tyr Thr Leu Ser Ser Ser Val Thr Val
        195                 200                 205

Pro Ser Ser Thr Trp Pro Ser Glu Thr Val Thr Cys Asn Val Ala His
    210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
        275                 280                 285

Gln Phe Ser Trp Phe Val Asp Asp Val Glu Val His Thr Ala Gln Thr
    290                 295                 300

Gln Pro Arg Glu Glu Gln Phe Ala Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
```

-continued

```
            340                 345                 350

Lys Thr Lys Gly Arg Pro Lys Ala Pro Gln Val Tyr Thr Ile Pro Pro
        355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asp Thr Asp
                405                 410                 415

Gly Ser Tyr Phe Val Tyr Ser Lys Leu Asn Val Gln Lys Ser Asn Trp
            420                 425                 430

Glu Ala Gly Asn Thr Phe Thr Cys Ser Val Leu His Glu Gly Leu His
        435                 440                 445

Asn His His Thr Glu Lys Ser Leu Ser His Ser Pro Gly Lys
    450                 455                 460


<210> SEQ ID NO 107
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 107

Gly Gly Gly Gly Ala
1               5
```

GROWTH DIFFERENTIATION FACTOR 15 COMBINATION THERAPY

RELATED APPLICATIONS

This application is a U.S. national stage filing under 35 U.S.C. § 371 of PCT Application No. PCT/US2020/021314, filed on Mar. 6, 2020, which claims the benefit of U.S. Provisional Application No. 62/815,866, filed on Mar. 8, 2019, both of which are hereby incorporated by reference in its entirety.

SEQUENCE LISTING

The present application is being filed along with a Sequence Listing in electronic format. The Sequence Listing is provided as a file entitled A-2298-WO-PCT_SeqList.txt, created Mar. 2, 2020, which is 166 kb in size. The information in the electronic format of the Sequence Listing is incorporated herein by reference in its entirety.

FIELD OF THE INVENTION

The instant disclosure relates to GDF15 molecules, such as GDF15 fusion proteins, compositions thereof, and methods for making and using such proteins, such as its use in combination therapy.

BACKGROUND

Growth differentiation factor 15 (GDF15), also referred to as macrophage inhibitory cytokine 1 (MIC1) (Bootcov M R, 1997, *Proc Natl Acad Sci* 94:11514-9), placental bone morphogenetic factor (PLAB) (Hromas R 1997, *Biochim Biophys Acta.* 1354:40-4), placental transforming growth factor beta (PTGFB) (Lawton LN 1997, *Gene.* 203:17-26), prostate derived factor (PDF) (Paralkar V M 1998, *J Biol Chem.* 273:13760-7), and nonsteroidal anti-inflammatory drug-activated gene (NAG-1) (Baek S J 2001, *J Biol Chem.* 276: 33384-92), is a secreted protein that circulates in plasma as an ~25 kDa homodimer. GDF15 binds to GDNF family receptor α-like (GFRAL) with high affinity. GDF15-induced cell signaling is believed to require the interaction of GFRAL with the coreceptor RET.

GDF15 has been linked to multiple biological activities. Elevated GDF15 has been shown to be correlated with weight loss and administration of GDF15 has been shown to reduce food intake and body weight.

Glucose-dependent insulinotropic polypeptide (GIP, formerly called gastric inhibitory polypeptide) and glucagon like polypeptide-1 (GLP-1) are known insulinotropic factors ("incretins"). GIP is a single 42-amino acid peptide and human GIP is derived from the processing of proGIP, a 153-amino acid precursor. GIP secretion is induced by food ingestion and has a number of physiological effects, including promotion of fat storage in adipocytes and promotion of pancreatic islet β-cell function and glucose-dependent insulin secretion. Intact GIP is rapidly degraded by DPPIV to an inactive form. The receptor for GIP, GIP receptor (GIPR), is a member of the secretin-glucagon family of G-protein coupled receptors (GPCRs). Human GIPR comprises 466 amino acids.

Glucagon-like peptide-1 (GLP-1) is a 31-amino acid peptide derived from the proglucagon gene. It is secreted by intestinal L-cells and released in response to food ingestion to induce insulin secretion from pancreatic β-cells. In addition to the incretin effects, GLP-1 also decreases glucagon secretion, delays gastric emptying and reduces caloric intake. GLP-1 exerts its effects by activation of the GLP-1 receptor (GLP-1R), which belongs to a class B G-protein-coupled receptor. The function of GLP-1 is limited by rapid degradation by the DPP-IV enzyme. Longer lasting GLP-1R agonists such as exenatide, liraglutide, dulaglutide have been developed and are being used clinically to improve glycemic control in patients with type 2 diabetes. Furthermore, GLP-1R agonists can promote body weight reduction as well as reduction in blood pressure and plasma cholesterol levels in patients.

Accordingly, there is a need for combination therapy comprising a GDF15 molecule with one or more other therapeutic agent(s), such as a GLP-1R agonist (e.g., a GLP-1 analog), and/or a GIPR antagonist (e.g., a GIPR antibody). The present disclosure meets this need and provide related advantages.

SUMMARY

Provided herein is combination therapy comprising a GDF15 molecule, including methods of treating a condition comprising administering a GDF15 molecule and another therapeutic agent. In one embodiment, the other therapeutic agent is a GIPR antagonist, such as a GIPR antigen binding protein. In one embodiment, the GIPR antigen binding protein is an antibody. In another embodiment, the other therapeutic agent is a GLP-1R agonist, such as dulaglutide.

Also provided herein is a method of treating a metabolic condition in a subject comprising administering a GDF15 molecule and a GIPR antagonist, wherein administration of the GDF15 molecule and the GIPR antagonist has a synergistic effect as compared to administration of the GDF15 molecule or GIPR antagonist alone.

The present disclose also provides a method of treating a metabolic condition in a subject comprising administering a GDF15 molecule and dulaglutide, wherein administration of the GDF15 molecule and dulaglutide has a synergistic effect as compared to administration of the GDF15 molecule or dulaglutide alone.

In one embodiment, combination therapy comprises administering a GDF15 molecule with a corresponding Fc molecule, such as described herein and in Table 6.

In one embodiment, the GDF15 molecule and the other therapeutic agent are administered concurrently. In another embodiment, the GDF15 molecule and the other therapeutic agent are administered sequentially.

Also provided herein is a pharmaceutical composition comprising a GDF15 molecule and the other therapeutic agent, such as a pharmaceutical composition comprising a GDF15 molecule a GIPR antagonist, wherein administration of the composition has a synergistic effect as compared to administration of the GDF15 molecule or GIPR antagonist alone. In some embodiments, the GIPR antagonist is an antibody. In some embodiments, the synergistic effect is in decreasing body weight. The GIPR antagonist of the composition may comprise a CDRL1, CDRL2, CDRL3, CDRH1, CDRH2, and CDRH3, wherein the CDRL1, CDRL2, CDRL3, CDRH1, CDRH2, and CDRH3 comprises the amino acid sequences of SEQ ID NOs: 65-67 and 77-79; SEQ ID NOs: 68-70 and 80-82; SEQ ID NOs: 71-73 and 83-85; or SEQ ID NOs: 74-76 and 86-88; respectively. In some embodiments, the GIPR antagonist of the composition comprises a light chain variable region and a heavy chain variable region comprising the amino acid sequences of SEQ ID NOs: 89 and 90; 91 and 92; 93 and 94; or 95 and 96, respectively. In some embodiments, the GIPR antagonist of the composition comprises a light chain and a heavy chain comprising the amino acid sequences of SEQ ID NOs: 97 and 98; 99 and 100; 101 and 102; 103 and 104, or 105 and 106, respectively. In some embodiments, the GDF15 molecule of the composition is a fusion protein comprising a GDF15 region joined to an Fc region. In some embodiments, the GDF15 region is joined to the Fc region via a linker. In some embodiments, the GDF15 region comprises the amino acid sequence of SEQ ID NO: 6 and at least one mutation. In some embodiments, at least one of the mutations is of the aspartate at position 5. In some embodiments, the aspartate at position 5 is mutated to glutamate. In some embodiments, the GDF15 region further comprises a mutation of the asparagine at position 3. In some embodiments, the asparagine at position 3 mutated to glutamine. In some embodiments, the linker of the GDF molecule joined to the Fc region is a (G4S)n or (G4Q)n linker, wherein n is greater than 0 (e.g., n is 1 or 2). The Fc region may comprise a charged pair mutation or a truncated hinge region, or both. In some embodiments, the Fc region is selected from Table 3. In yet other embodiments, the composition further comprises a corresponding Fc molecule to the GDF15 molecule, e.g., as described herein and in Table 6.

Also provided herein is a pharmaceutical composition comprising a GDF15 molecule and dulaglutide, wherein administration of the composition has a synergistic effect as compared to administration of the GDF15 molecule or dulaglutide alone. A pharmaceutical composition comprising a GDF15 molecule and dulaglutide, wherein administration of the composition has a synergistic effect as compared to administration of the GDF15 molecule or dulaglutide alone. In some embodiments, the synergistic effect is in decreasing body weight. In some embodiments, the GDF15 molecule of the composition is a fusion protein comprising a GDF15 region joined to an Fc region. In some embodiments, the GDF15 region is joined to the Fc region via a linker. In some embodiments, the GDF15 region comprises the amino acid sequence of SEQ ID NO: 6 and at least one mutation. In some embodiments, at least one of the mutations is of the aspartate at position 5. In some embodiments, the aspartate at position 5 is mutated to glutamate. In some embodiments, the GDF15 region further comprises a mutation of the asparagine at position 3. In some embodiments, the asparagine at position 3 mutated to glutamine. In some embodiments, the linker of the GDF molecule joined to the Fc region is a (G4S)n or (G4Q)n linker, wherein n is greater than 0 (e.g., n is 1 or 2). The Fc region may comprise a charged pair mutation or a truncated hinge region, or both. In some embodiments, the Fc region is selected from Table 3. In yet other embodiments, the composition further comprises a corresponding Fc molecule to the GDF15 molecule, e.g., as described herein and in Table 6.

DETAILED DESCRIPTION

Figure 1A:
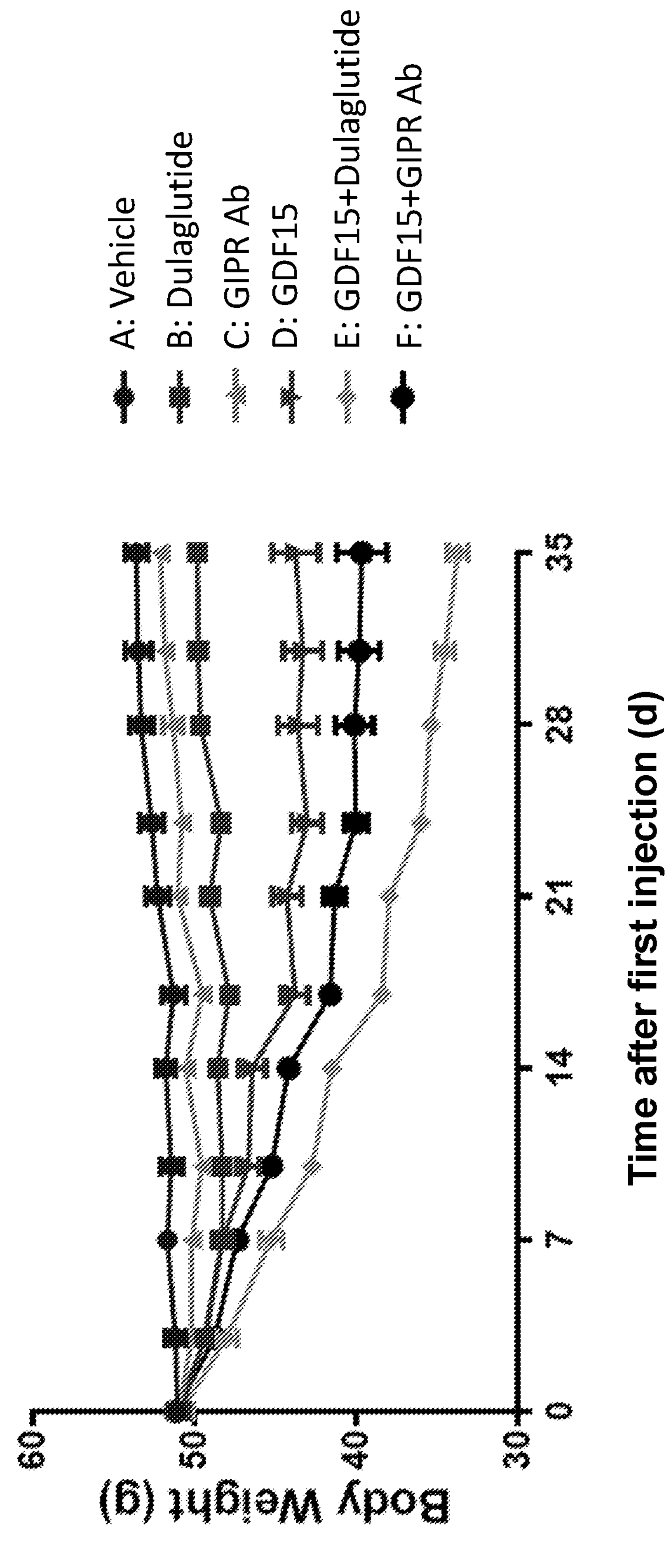
FIG. 1A shows the body weight change in grams in mice administered vehicle weekly (Group A); dulaglutide twice per week (Group B); GIPR antibody 2.63.1 weekly and vehicle weekly, the latter being on the alternate dulaglutide dosing day (Group C); FcΔ10(−)-(G4S)4-GDF15 (SEQ ID NO: 39) (along with its heterodimerization partner, FcΔ10 (+,K) (SEQ ID NO: 32)) weekly and vehicle weekly, the latter on the alternate dulaglutide dosing day (Group D); FcΔ10(−)-(G4S)4-GDF15) (along with its heterodimerization partner, FcΔ10(+,K)) weekly and dulaglutide twice per week (Group E); FcΔ10(−)-(G4S)4-GDF15 (along with its heterodimerization partner, FcΔ10(+,K)) weekly and GIPR antibody 2.63.1 weekly (Group F).

Provided herein is combination therapy comprising a GDF15 molecule and another therapeutic agent or molecule. In one embodiment, the other agent or molecule is a molecule that reduces body weight, food intake and/or treat obesity and/or a related condition. Also provided herein are methods of making the molecules and methods of using the molecules.

In some embodiments, the GDF15 molecule is a GDF15-Fc fusion protein. The fusion protein can comprise a GDF15 region joined to an Fc region. In some embodiments, the GDF15 region is joined to the Fc via a linker. In some embodiments, the GDF15 region comprises wild type GDF15. Both the human and murine GDF15 have a signal peptide and prodomain. The nucleotide sequence for full length human GDF15 is:

```
                                      (SEQ ID NO: 1)
atgcccgggc aagaactcag gacggtgaat ggctctcaga

tgctcctggt gttgctggtg ctctcgtggc tgccgcatgg

gggcgccctg tctctggccg aggcgagccg cgcaagtttc

ccgggaccct cagagttgca ctccgaagac tccagattcc

gagagttgcg gaaacgctac gaggacctgc taaccaggct

gcgggccaac cagagctggg aagattcgaa caccgacctc

gtcccggccc ctgcagtccg gatactcacg ccagaagtgc

ggctgggatc cggcggccac ctgcacctgc gtatctctcg
```

-continued

```
ggccgccctt cccgaggggc tccccgaggc ctcccgcctt
caccgggctc tgttccggct gtccccgacg gcgtcaaggt
cgtgggacgt gacacgaccg ctgcggcgtc agctcagcct
tgcaagaccc caggcgcccg cgctgcacct gcgactgtcg
ccgccgccgt cgcagtcgga ccaactgctg gcagaatctt
cgtccgcacg gccccagctg gagttgcact tgcggccgca
agccgccagg gggcgccgca gagcgcgtgc gcgcaacggg
gaccactgtc cgctcgggcc cgggcgttgc tgccgtctgc
acacggtccg cgcgtcgctg gaagacctgg gctgggccga
ttgggtgctg tcgccacggg aggtgcaagt gaccatgtgc
atcggcgcgt gcccgagcca gttccgggcg gcaaacatgc
acgcgcagat caagacgagc ctgcaccgcc tgaagcccga
cacggtgcca gcgccctgct gcgtgcccgc cagctacaat
cccatggtgc tcattcaaaa gaccgacacc ggggtgtcgc
tccagaccta tgatgacttg ttagccaaag actgccactg
catatga
```

The amino acid sequence for full length human GDF15 (308 amino acids) is:

(SEQ ID NO: 2)

```
MPGQELRTVNGSQMLLVLLVLSWLPHGGALSLAEASRASFPGPSELHSEDS
RFRELRKRYEDLLTRLRANQSWEDSNTDLVPAPAVRILTPEVRLGSGGHLH
LRISRAALPEGLPEASRLHRALFRLSPTASRSWDVTRPLRRQLSLARPQAP
ALHLRLSPPPSQSDQLLAESSSARPQLELHLRPQAARGRRRARARNGDHCP
LGPGRCCRLHTVRASLEDLGWADWVLSPREVQVTMCIGACPSQFRAANMHA
QIKTSLHRLKPDTVPAPCCVPASYNPMVLIQKTDTGVSLQTYDDLLAKDCH
CI
```

The nucleotide sequence for human GDF15 without its signal sequence is:

(SEQ ID NO: 3)

```
ctgtctctgg ccgaggcgag ccgcgcaagt ttcccgggac
cctcagagtt gcactccgaa gactccagat tccgagagtt
gcggaaacgc tacgaggacc tgctaaccag gctgcgggcc
aaccagagct gggaagattc gaacaccgac ctcgtcccgg
cccctgcagt ccggatactc acgccagaag tgcggctggg
atccggcggc cacctgcacc tgcgtatctc tcgggccgcc
cttcccgagg ggctccccga ggcctcccgc cttcaccggg
ctctgttccg gctgtccccg acggcgtcaa ggtcgtggga
cgtgacacga ccgctgcggc gtcagctcag ccttgcaaga
ccccaggcgc ccgcgctgca cctgcgactg tcgccgccgc
cgtcgcagtc ggaccaactg ctggcagaat cttcgtccgc
```

-continued

```
acggccccag ctggagttgc acttgcggcc gcaagccgcc
agggggcgcc gcagagcgcg tgcgcgcaac ggggaccact
gtccgctcgg gcccgggcgt tgctgccgtc tgcacacggt
ccgcgcgtcg ctggaagacc tgggctgggc cgattgggtg
ctgtcgccac gggaggtgca agtgaccatg tgcatcggcg
cgtgcccgag ccagttccgg gcggcaaaca tgcacgcgca
gatcaagacg agcctgcacc gcctgaagcc cgacacggtg
ccagcgccct gctgcgtgcc cgccagctac aatcccatgg
tgctcattca aaagaccgac accggggtgt cgctccagac
ctatgatgac ttgttagcca aagactgcca ctgcatatga
```

The amino acid sequence for human GDF15 without its 29 amino acid signal sequence (279 amino acids) is:

(SEQ ID NO: 4)

```
LSLAEASRASFPGPSELHSEDSRFRELRKRYEDLLTRLRANQSWEDSNTDL
VPAPAVRILTPEVRLGSGGHLHLRISRAALPEGLPEASRLHRALFRLSPTA
SRSWDVTRPLRRQLSLARPQAPALHLRLSPPPSQSDQLLAESSSARPQLEL
HLRPQAARGRRRARARNGDHCPLGPGRCCRLHTVRASLEDLGWADWVLSPR
EVQVTMCIGACPSQFRAANMHAQIKTSLHRLKPDTVPAPCCVPASYNPMVL
IQKTDTGVSLQTYDDLLAKDCHCI
```

The nucleotide sequence for human GDF15 without its signal peptide or prodomain is:

(SEQ ID NO: 5)

```
gcgcgcaacggggaccactgtccgctcgggcccgggcgttgctgccgtctg
cacacggtccgcgcgtcgctggaagacctgggctgggccgattgggtgctg
tcgccacgggaggtgcaagtgaccatgtgcatcggcgcgtgcccgagccag
ttccgggcggcaaacatgcacgcgcagatcaagacgagcctgcaccgcctg
aagcccgacacggtgccagcgccctgctgcgtgcccgccagctacaatccc
atggtgctcattcaaaagaccgacaccggggtgtcgctccagacctatgat
gacttgttagccaaagactgccactgcatatga
```

The amino acid sequence for human GDF15 without its signal peptide or prodomain (the active domain of GDF15 of 112 amino acids) is:

(SEQ ID NO: 6)

```
ARNGDHCPLGPGRCCRLHTVRASLEDLGWADWVLSPREVQVTMCIGACPSQ
FRAANMHAQIKTSLHRLKPDTVPAPCCVPASYNPMVLIQKTDTGVSLQTYD
DLLAKDCHCI
```

The nucleotide sequence for full length murine GDF15 is:

(SEQ ID NO: 7)

```
atggccccgc ccgcgctcca ggcccagcct ccaggcggct
ctcaactgag gttcctgctg ttcctgctgc tgttgctgct
gctgctgtca tggccatcgc agggggacgc cctggcaatg
```

-continued cctgaacagc gaccctccgg ccctgagtcc caactcaacg ccgacgagct acggggtcgc ttccaggacc tgctgagccg gctgcatgcc aaccagagcc gagaggactc gaactcagaa ccaagtcctg acccagctgt ccggatactc agtccagagg tgagattggg gtcccacggc cagctgctac tccgcgtcaa ccgggcgtcg ctgagtcagg gtctccccga agcctaccgc gtgcaccgag cgctgctcct gctgacgccg acggcccgcc cctgggacat cactaggccc ctgaagcgtg cgctcagcct ccggggaccc cgtgctcccg cattacgcct gcgcctgacg ccgcctccgg acctggctat gctgccctct ggcggcacgc agctggaact gcgcttacgg gtagccgccg gcagggggcg ccgaagcgcg catgcgcacc caagagactc gtgcccactg ggtccggggc gctgctgtca cttggagact gtgcaggcaa ctcttgaaga cttgggctgg agcgactggg tgctgtcccc gcgccagctg cagctgagca tgtgcgtggg cgagtgtccc cacctgtatc gctccgcgaa cacgcatgcg cagatcaaag cacgcctgca tggcctgcag cctgacaagg tgcctgcccc gtgctgtgtc ccctccagct acaccccggt ggttcttatg cacaggacag acagtggtgt gtcactgcag acttatgatg acctggtggc ccggggctgc cactgcgctt ga The amino acid sequence for full length murine GDF15 (303 amino acids) is:

(SEQ ID NO: 8)
MAPPALQAQPPGGSQLRFLLFLLLLLLLLSWPSQGDALAMPEQRPSGPESQ

LNADELRGRFQDLLSRLHANQSREDSNSEPSPDPAVRILSPEVRLGSHGQL

LLRVNRASLSQGLPEAYRVHRALLLLTPTARPWDITRPLKRALSLRGPRAP

ALRLRLTPPPDLAMLPSGGTQLELRLRVAAGRGRRSAHAHPRDSCPLGPGR

CCHLETVQATLEDLGWSDWVLSPRQLQLSMCVGECPHLYRSANTHAQIKAR

LHGLQPDKVPAPCCVPSSYTPVVLMHRTDSGVSLQTYDDLVARGCHCA

The nucleotide sequence for murine GDF15 without its signal sequence is:

(SEQ ID NO: 9)
tcgcagggggacgccctggcaatgcctgaacagcgaccctccggccctgag tcccaactcaacgccgacgagctacggggtcgcttccaggacctgctgagc cggctgcatgccaaccagagccgagaggactcgaactcagaaccaagtcct gacccagctgtccggatactcagtccagaggtgagattggggtcccacggc cagctgctactccgcgtcaaccgggcgtcgctgagtcagggtctccccgaa gcctaccgcgtgcaccgagcgctgctcctgctgacgccgacggcccgcccc tgggacatcactaggcccctgaagcgtgcgctcagcctccggggaccccgt gctcccgcattacgcctgcgcctgacgccgcctccggacctggctatgctg ccctctggcggcacgcagctggaactgcgcttacgggtagccgccggcagg -continued gggcgccgaagcgcgcatgcgcacccaagagactcgtgcccactgggtccg gggcgctgctgtcacttggagactgtgcaggcaactcttgaagacttgggc tggagcgactgggtgctgtccccgcgccagctgcagctgagcatgtgcgtg ggcgagtgtccccacctgtatcgctccgcgaacacgcatgcgcagatcaaa gcacgcctgcatggcctgcagcctgacaaggtgcctgccccgtgctgtgtc ccctccagctacaccccggtggttcttatgcacaggacagacagtggtgtg tcactgcagacttatgatgacctggtggcccggggctgccactgcgcttga The amino acid sequence for murine GDF15 without its 32 amino acid signal sequence (271 amino acids) is:

(SEQ ID NO: 10)
SQGDALAMPEQRPSGPESQLNADELRGRFQDLLSRLHANQSREDSNSEPSP

DPAVRILSPEVRLGSHGQLLLRVNRASLSQGLPEAYRVHRALLLLTPTARP

WDITRPLKRALSLRGPRAPALRLRLTPPPDLAMLPSGGTQLELRLRVAAGR

GRRSAHAHPRDSCPLGPGRCCHLETVQATLEDLGWSDWVLSPRQLQLSMCV

GECPHLYRSANTHAQIKARLHGLQPDKVPAPCCVPSSYTPVVLMHRTDSGV

SLQTYDDLVARGCHCA

The nucleotide sequence for murine GDF15 without its signal sequence or prodomain is:

(SEQ ID NO: 11)
agcgcgcatgcgcacccaagagactcgtgcccactgggtccggggcgctgc tgtcacttggagactgtgcaggcaactcttgaagacttgggctggagcgac tgggtgctgtccccgcgccagctgcagctgagcatgtgcgtgggcgagtgt ccccacctgtatcgctccgcgaacacgcatgcgcagatcaaagcacgcctg catggcctgcagcctgacaaggtgcctgccccgtgctgtgtcccctccagc tacaccccggtggacttatgcacaggacagacagtggtgtgtcactgcaga cttatgatgacctggtggcccggggctgccactgcgcttga The amino acid sequence for murine GDF15 without its signal peptide or prodomain (active domain of 115 amino acids) is:

(SEQ ID NO: 12)
SAHAHPRDSCPLGPGRCCHLETVQATLEDLGWSDWVLSPRQLQLSMCVGEC

PHLYRSANTHAQIKARLHGLQPDKVPAPCCVPSSYTPVVLMHRTDSGVSLQ

TYDDLVARGCHCA

In some embodiments, the GDF15 molecule comprises a GDF15 region comprising an active domain of GDF15, e.g., GDF15 without its signal peptide or prodomain. In some embodiments, the GDF15 region comprises the amino acid sequence of SEQ ID NO: 6 or 12. In some embodiments, the GDF15 region comprises a GDF15 sequence with one or more mutations, such as at least one mutation in the active domain of GDF15. In particular embodiments, the mutation or mutations do not reduce or eliminate the activity of GDF15. In some embodiments, the GDF15 region comprises a mutation in the active domain of human GDF15. In one embodiment, the mutation is a deletion of the first three amino acids of the active domain, such as "GDF15(Δ3)"

which is an active domain of human GDF15 in which the first three amino acids removed (i.e., SEQ ID NO: 13).

In some embodiments, the GDF15 region comprises a mutation of the asparagine at position 3 (N3) of the active domain of human GDF15 (SEQ ID NO: 6). An N3 mutation can refer to the mutation of the asparagine residue at position 3 of SEQ ID NO: 6 or the mutation of an asparagine residue corresponding to the asparagine at position 3 of SEQ ID NO: 6 in a GDF15 amino acid sequence. In some embodiments, the asparagine at position 3 is mutated to glutamine (N3Q) or aspartate (N3D). Accordingly, in some embodiments, the GDF15 molecule comprises a GDF15 region of GDF15 (N3Q), which has the amino acid sequence of SEQ ID NO: 14. In other embodiments, the GDF15 molecule comprises a GDF15 region of GDF15(N3D), which has the amino acid sequence of SEQ ID NO: 15. In some embodiments, the GDF15 region comprises a mutation of the aspartate at position 5 (D5) of the active domain of human GDF15 (SEQ ID NO: 6). A D5 mutation can refer to the mutation of the aspartate residue at position 5 of SEQ ID NO: 6 or the mutation of an aspartate residue corresponding to the aspartate at position 5 of SEQ ID NO: 6 in a GDF15 amino acid sequence. In one embodiment, the aspartate at position 5 is mutated to glutamate (D5E). Accordingly, in some embodiments, the GDF15 molecule comprises a GDF15 region of GDF15(D5E), which has the amino acid sequence of SEQ ID NO: 16.

In yet other embodiments, the GDF15 region comprises a combination of mutations, such as a combination of 43 and D5 mutations, e.g., GDF15(Δ3/D5E) (SEQ ID NO: 17) or a combination of N3 and D5 mutations, e.g., GDF15(N3D/D5E) or GDF15(N3Q/D5E). In, the GDF15 region comprises the amino acid sequence of SEQ ID NO: 18.

Table 1 provides examples of GDF15 regions that can be used in the GDF15 molecules.

TABLE 1

GDF15 Regions

| SEQ ID NO: | Designation | Sequence |
|---|---|---|
| 6 | GDF15 | ARNGDHCPLGPGRCCRLHTVRASLEDLGWADWVLSPREVQ VTMCIGACPSQFRAANMHAQIKTSLHRLKPDTVPAPCCVPAS YNPMVLIQKTDTGVSLQTYDDLLAKDCHCI |
| 13 | GDF15(Δ3) | GDHCPLGPGRCCRLHTVRASLEDLGWADWVLSPREVQVTM CIGACPSQFRAANMHAQIKTSLHRLKPDTVPAPCCVPASYNP MVLIQKTDTGVSLQTYDDLLAKDCHCI |
| 14 | GDF15(N3Q) | ARQGDHCPLGPGRCCRLHTVRASLEDLGWADWVLSPREVQ VTMCIGACPSQFRAANMHAQIKTSLHRLKPDTVPAPCCVPAS YNPMVLIQKTDTGVSLQTYDDLLAKDCHCI |
| 15 | GDF15(N3D) | ARDGDHCPLGPGRCCRLHTVRASLEDLGWADWVLSPREVQ VTMCIGACPSQFRAANMHAQIKTSLHRLKPDTVPAPCCVPAS YNPMVLIQKTDTGVSLQTYDDLLAKDCHCI |
| 16 | GDF15(D5E) | ARNGEHCPLGPGRCCRLHTVRASLEDLGWADWVLSPREVQ VTMCIGACPSQFRAANMHAQIKTSLHRLKPDTVPAPCCVPAS YNPMVLIQKTDTGVSLQTYDDLLAKDCHCI |
| 17 | GDF15(Δ3/D5E) | GEHCPLGPGRCCRLHTVRASLEDLGWADWVLSPREVQVTM CIGACPSQFRAANMHAQIKTSLHRLKPDTVPAPCCVPASYNP MVLIQKTDTGVSLQTYDDLLAKDCHCI |
| 18 | GDF15(N3Q/D5E) | ARQGEHCPLGPGRCCRLHTVRASLEDLGWADWVLSPREVQ VTMCIGACPSQFRAANMHAQIKTSLHRLKPDTVPAPCCVPAS YNPMVLIQKTDTGVSLQTYDDLLAKDCHCI |

In some embodiments, the GDF15 molecule is fused to an Fc directly. In other embodiments, the Fc is fused to the GDF15 molecule via a linker. In some embodiments, the linker is a G4S (SEQ ID NO: 19) linker. In other embodiments, the linker is a G4Q (SEQ ID NO: 24) linker. The linker can be a (G4S)n or (G4Q)n linker, wherein n is greater than 0. In some embodiments, n is 1 or 2. In some embodiments, the fusion protein has a linker that is a G4A (SEQ ID NO: 107) linker, such as a (G4A)n linker, wherein n is greater than 0. In some embodiments, n is 1 or 2. In some embodiments, n is greater than 2, such as 3, 4, 5, 6, 7, or 8. In some embodiments, the linker comprises the amino acid sequence of SEQ ID NO: 19, 20, 21, 22, 23, 24, 25 or 107, as shown in Table 2.

TABLE 2

Linkers

| SEQ ID NO: | Designation | Sequence |
|---|---|---|
| 19 | G4S | GGGGS |
| 20 | (G4S)2 | GGGGSGGGGS |
| 21 | (G4S)4 | GGGGSGGGGSGGGGSGGGGS |
| 22 | (G4S)8 | GGGGSGGGGSGGGGSGGGGSGGGGSG GGGSGGGGSGGGGS |
| 23 | G4 | GGGG |
| 24 | G4Q | GGGGQ |
| 25 | (G4Q)4 | GGGGQGGGGQGGGGQGGGGQ |
| 107 | G4A | GGGGA |

In some embodiments, the GDF15 molecule comprises an Fc region. The Fc region can comprise or be derived from the Fc domain of a heavy chain of an antibody. In some embodiments, the Fc region may comprise an Fc domain with a mutation, such as a charged pair mutation, a mutation in a glycosylation site or the inclusion of an unnatural amino acid. The Fc region can be derived from a human IgG constant domain of IgG1, IgG2, IgG3 or IgG4. In some embodiments, the Fc region comprises the constant domain of an IgA, IgD, IgE, and IgM heavy chain.

In some embodiments, the Fc region comprises an Fc domain with a charged pair mutation. By introducing a mutation resulting in a charged Fc region, the GDF15 molecule can dimerize with a corresponding Fc molecule having the opposite charge. For example, an aspartate-to-lysine mutation (E356K, wherein 356 is the position using EU numbering, and corresponds to the positions as noted in Tables 3-5) and a glutamate-to-lysine mutation (D399K wherein 399 is the position using EU numbering, and corresponds to positions as noted in Tables 3-5) can be introduced into the Fc region that is joined to a GDF15 region, optionally via a linker, resulting in a positively charged Fc region for the GDF15 molecule. Lysine-to-aspartate mutations (K392D, K409D; wherein 392 and 409 are the positions using EU numbering and corresponds to the positions as noted in Tables 3-5) can be introduced into an Fc domain of a separate molecule, resulting in a negatively charged Fc molecule. The aspartate residues in the negatively charged Fc molecule can associate with the lysine residues of the positively charged Fc region of the GDF15 molecule through electrostatic force, facilitating formation of Fc heterodimers between the Fc region of the GDF15 molecule and the Fc molecule, while reducing or preventing formation of Fc homodimers between the Fc regions of the GDF15 molecules or between Fc molecules.

In some embodiments, one or more lysine-to-aspartate mutations (K392D, K409D) are introduced into the Fc region that is joined to a GDF15 region, optionally via a linker and an aspartate-to-lysine mutation (E356K) and a glutamate-to-lysine mutation (D399K) is introduced into the Fc domain of another molecule. The aspartate residues in the Fc region of the GDF15 molecule can associate with the lysine residues of the Fc molecule through electrostatic force, facilitating formation of Fc heterodimers between the Fc region of the GDF15 molecule and the Fc molecule, and reducing or preventing formation of Fc homodimers between the Fc regions of the GDF15 molecules or between Fc molecules.

In some embodiments, the GDF15 molecule comprises an Fc region comprising an Fc domain with a mutated hinge region. In some embodiments, the Fc domain comprises a deletion in the hinge. In some embodiments, ten amino acids from the hinge are deleted, e.g., FcΔ10. In other embodiments, sixteen amino acids from the hinge are deleted, e.g., FcΔ16. In some embodiments, the Fc domain comprises a hinge deletion (e.g., FcΔ10 or FcΔ16) and a charged pair mutation, such that the Fc domain is positively or negatively charged. For example, the Fc domain can comprise a ten-amino acid deletion in the hinge and lysine-to-aspartate mutations (K392D, K409D), such as FcΔ10(−). In another embodiment, the Fc domain can comprise a ten-amino acid deletion in the hinge and an aspartate-to-lysine mutation (E356K) and a glutamate-to-lysine mutation (D399K), such as an FcΔ10(+). In another embodiment, the Fc domain can comprise a sixteen-amino acid deletion in the hinge and lysine-to-aspartate mutations (K392D, K409D), such as FcΔ16(−). In another embodiment, the Fc domain can comprise a sixteen-amino acid deletion in the hinge and an aspartate-to-lysine mutation (E356K) and a glutamate-to-lysine mutation (D399K), such as an FcΔ16(+).

In some embodiments, an Fc molecule comprising a hinge deletion and a charged pair mutation heterodimerizes with such a GDF15 molecule. For example, the Fc molecule can have a hinge deletion and charged pair mutation that complements the hinge deletion and charged pair mutation of the Fc region of a GDF15 molecule. For example, an Fc molecule can comprise an Fc domain with a ten-amino acid deletion in the hinge and lysine-to-aspartate mutations (K392D, K409D), such as FcΔ10(−), which can optionally comprise a C-terminal lysine (e.g., FcΔ10(−, K)). The Fc molecule can heterodimerize with a GDF15 molecule that comprises an FcΔ10(+). In another embodiment, the Fc molecule can comprise a ten-amino acid deletion in the hinge and an aspartate-to-lysine mutation (E356K) and a glutamate-to-lysine mutation (D399K), such as an FcΔ10 (+), which can optionally comprise a C-terminal lysine (e.g., FcΔ10(+, K)). The Fc molecule can heterodimerize with a GDF15 molecule that comprises an FcΔ10(−). In another embodiment, the Fc molecule can comprise a sixteen-amino acid deletion in the hinge and lysine-to-aspartate mutations (K392D, K409D), such as FcΔ16(−), which can optionally comprise a C-terminal lysine (e.g., FcΔ16(−, K)). The Fc molecule which can heterodimerize with a GDF15 molecule that comprises an FcΔ16(+). In another embodiment, the Fc molecule can comprise a sixteen-amino acid deletion in the hinge and an aspartate-to-lysine mutation (E356K) and a glutamate-to-lysine mutation (D399K), such as an FcΔ16 (+), which can optionally comprise a C-terminal lysine (e.g., FcΔ16(−, K)). The Fc molecule can heterodimerize with a GDF15 molecule that comprises an FcΔ16(−).

In some embodiments, the Fc region or Fc molecule comprises an Fc domain with an L234A and/or L235A mutation, wherein 234 and 235 are the positions using EU numbering and corresponds to the positions as noted in Tables 3-5. The Fc domain can comprise an L234A mutation, an L235A mutation, a charged pair mutation, a hinge deletion, or any combination thereof. In some embodiments, the Fc domain comprises both an L234A mutation and an L235A mutation. In some embodiments, the Fc domain comprises a hinge deletion, an L234A mutation, an L235A mutation, and a charged pair mutation, such as FcΔ10(+, L234A/L235A), FcΔ10(−, L234A/L235A), FcΔ16(+, L234A/L235A), or FcΔ16(−, L234A/L235A). In some embodiments, the Fc domain comprises an optional C-terminal lysine, e.g., FcΔ10(+,K,L234A/L235A), FcΔ10(−,K, L234A/L235A), FcΔ16(+,K,L234A/L235A), or FcΔ16(−,K, L234A/L235A).

In some embodiments, the Fc region or Fc molecule comprises an Fc domain with a "cysteine clamp" A cysteine clamp mutation involves the introduction of a cysteine into the Fc domain at a specific location through mutation so that when incubated with another Fc domain that also has a cysteine introduced at a specific location through mutation, a disulfide bond (cysteine clamp) may be formed between the two Fc domains (e.g., between an FcΔ16 (+) domain having a "cysteine clamp" mutation and an FcΔ16(−) domain having a "cysteine clamp" mutation). The cysteine can be introduced into the CH3 domain of an Fc domain. In some embodiments, an Fc domain may contain one or more such cysteine clamp mutations. In one embodiment, a cysteine clamp is provided by introducing a serine to cysteine mutation (S354C, wherein 354 is the position using EU numbering, and corresponds to the position as noted in Tables 3-5) into a first Fc domain and a tyrosine to cysteine mutation (Y349C, wherein 349 is the position using EU numbering, and corresponds to the position as noted in Tables 3-5) into a second Fc domain. In one embodiment, a GDF15 molecule comprises an Fc region comprising an Fc domain with a cysteine clamp, a negatively charged pair mutation and a sixteen-amino acid hinge deletion (e.g., GDF15-FcΔ16(−,CC)), and an Fc molecule comprising an Fc domain comprising a cysteine clamp, a positively charged pair mutation and a sixteen-amino acid hinge deletion, and an optional C-terminal lysine (e.g., FcΔ16(+,K, CC)). The cysteine clamp may augment the heterodimerization of the GDF-Fc molecule with the Fc molecule.

Examples of Fc regions that can be used in a GDF15 molecule are shown in Table 3.

TABLE 3

Fc Regions

| SEQ ID NO: | Designation | Sequence |
|---|---|---|
| 26 | FcΔ10(-) | APELLGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALPAPIEKTISKAKGQPR<br>EPQVYTLPPSREEMTKNQVSLTCLVKGFYPSDIAVEWES<br>NGQPENNYDTTPPVLDSDGSFFLYSDLTVDKSRWQQGN<br>VFSCSVMHEALHNHYTQKSLSLSPG<br>Underlined and bolded residues are K392D and K409D mutations. |
| 27 | FcΔ10(+) | APELLGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALPAPIEKTISKAKGQPR<br>EPQVYTLPPSRKEMTKNQVSLTCLVKGFYPSDIAVEWES<br>NGQPENNYKTTPPVLKSDGSFFLYSKLTVDKSRWQQGN<br>VFSCSVMHEALHNHYTQKSLSLSPG<br>Underlined and bolded residues are E356K and D399K mutations. |
| 28 | FcΔ10(-,CC) | APELLGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALPAPIEKTISKAKGQPR<br>EPQVCTLPPSREEMTKNQVSLTCLVKGFYPSDIAVEWES<br>NGQPENNYDTTPPVLDSDGSFFLYSDLTVDKSRWQQGN<br>VFSCSVMHEALHNHYTQKSLSLSPG<br>Underlined and italicized residue is Y349C mutation; underlined and bolded residues are K392D and K409D mutations. |
| 29 | FcΔ16(-,CC) | GPSVFLFPPKPKDTLMISRTPEVTCVVVDVSHEDPEVKF<br>NWYVDGVEVHNAKTKPREEQYNSTYRVVSVLTVLHQD<br>WLNGKEYKCKVSNKALPAPIEKTISKAKGQPREPQVCTL<br>PPSREEMTKNQVSLTCLVKGFYPSDIAVEWESNGQPENN<br>YDTTPPVLDSDGSFFLYSDLTVDKSRWQQGNVFSCSVM<br>HEALHNHYTQKSLSLSPG<br>Underlined and italicized residue is Y349C mutation; underlined and bolded residues are K392D and K409D mutations. |
| 30 | FcΔ16(-) | GPSVFLFPPKPKDTLMISRTPEVTCVVVDVSHEDPEVKF<br>NWYVDGVEVHNAKTKPREEQYNSTYRVVSVLTVLHQD<br>WLNGKEYKCKVSNKALPAPIEKTISKAKGQPREPQVYT<br>LPPSREEMTKNQVSLTCLVKGFYPSDIAVEWESNGQPEN<br>NYDTTPPVLDSDGSFFLYSDLTVDKSRWQQGNVFSCSV<br>MHEALHNHYTQKSLSLSPG<br>Underlined and bolded residues are K392D and K409D mutations. |
| 31 | FcΔ10(-, L234A/ L235A) | APEAAGGPSVFLFPPKPKDTLMISRTPEVTCVVVDVSHE<br>DPEVKFNWYVDGVEVHNAKTKPREEQYNSTYRVVSVL<br>TVLHQDWLNGKEYKCKVSNKALPAPIEKTISKAKGQPR<br>EPQVYTLPPSREEMTKNQVSLTCLVKGFYPSDIAVEWES<br>NGQPENNYDTTPPVLDSDGSFFLYSDLTVDKSRWQQGN<br>VFSCSVMHEALHNHYTQKSLSLSPG<br>Underlined and italicized residues are L234A and L235A mutations; underlined and bolded residues are K392D and K409D mutations. |

Examples of Fc molecules are shown in Table 4, in which the C-terminal lysine is optional.

TABLE 4

Fc Molecules

| SEQ ID NO: | Designation | Sequence |
|---|---|---|
| 32 | FcΔ10(+,K) | APELLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYTL PPSR**K**EMTKNQVSLTCLVKGFYPSDIAVEWESNGQPENNY KTTPPVL**K**SDGSFFLYSKLTVDKSRWQQGNVFSCSVMHEA LHNHYTQKSLSLSPGK<br>Underlined and bolded residues are E356K and D399K mutations. |
| 33 | FcΔ10(-,K) | APELLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYTL PPSREEMTKNQVSLTCLVKGFYPSDIAVEWESNGQPENNY **D**TTPPVLDSDGSFFLYS**D**LTVDKSRWQQGNVFSCSVMHEA LHNHYTQKSLSLSPGK<br>Underlined and bolded residues are K392D and K409D mutations. |
| 34 | FcΔ10(+,K,CC) | APELLGGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYTL PP*C*R**K**EMTKNQVSLTCLVKGFYPSDIAVEWESNGQPENNY KTTPPVL**K**SDGSFFLYSKLTVDKSRWQQGNVFSCSVMHEA LHNHYTQKSLSLSPGK<br>Underlined and italicized residue is S354C mutation; underlined and bolded residues are E356K and D399K mutations. |
| 35 | FcΔ16(+,K,CC) | GPSVFLFPPKPKDTLMISRTPEVTCVVVDVSHEDPEVKFNW YVDGVEVHNAKTKPREEQYNSTYRVVSVLTVLHQDWLNG KEYKCKVSNKALPAPIEKTISKAKGQPREPQVYTLPP*C*R**K**E MTKNQVSLTCLVKGFYPSDIAVEWESNGQPENNYKTTPPV L**K**SDGSFFLYSKLTVDKSRWQQGNVFSCSVMHEALHNHY TQKSLSLSPGK<br>Underlined and italicized residue is S354C mutation; underlined and bolded residues are E356K and D399K mutations. |
| 36 | FcΔ16(+,K) | GPSVFLFPPKPKDTLMISRTPEVTCVVVDVSHEDPEVKFNW YVDGVEVHNAKTKPREEQYNSTYRVVSVLTVLHQDWLNG KEYKCKVSNKALPAPIEKTISKAKGQPREPQVYTLPPSR**K**E MTKNQVSLTCLVKGFYPSDIAVEWESNGQPENNYKTTPPV L**K**SDGSFFLYSKLTVDKSRWQQGNVFSCSVMHEALHNHY TQKSLSLSPGK<br>Underlined and bolded residues are E356K and D399K mutations. |
| 37 | FcΔ10(+,K, L234A/L235A) | APE*AA*GGPSVFLFPPKPKDTLMISRTPEVTCVVVDVSHEDPE VKFNWYVDGVEVHNAKTKPREEQYNSTYRVVSVLTVLHQ DWLNGKEYKCKVSNKALPAPIEKTISKAKGQPREPQVYTL PPSR**K**EMTKNQVSLTCLVKGFYPSDIAVEWESNGQPENNY KTTPPVL**K**SDGSFFLYSKLTVDKSRWQQGNVFSCSVMHEA LHNHYTQKSLSLSPGK<br>Underlined and italicized residues are L234A and L235A mutations; underlined and bolded residues are E356K and D399K mutations. |

The Fc molecules can be used to dimerize with a molecule comprising a complementary Fc domain. For example, an Fc molecule of FcΔ10(+,K) can dimerize with a molecule comprising an Fc region comprising a ten-amino acid hinge deletion and a negatively charged pair mutation such as FcΔ10(−) (e.g., a GDF15 molecule comprising an Fc region of FcΔ10(−)). An Fc molecule of FcΔ10(−,K) can dimerize with a molecule comprising an Fc region comprising a ten-amino acid hinge deletion and a negatively charged pair mutation such as FcΔ10(+) (e.g., a GDF15 molecule comprising an Fc region of FcΔ10(+)).

An Fc molecule of FcΔ10(+,K,CC) can dimerize with a molecule comprising an Fc region comprising a ten-amino acid hinge deletion and a negatively charged pair mutation such as FcΔ10(−,CC) (e.g., a GDF15 molecule comprising an Fc region of FcΔ10(−, CC)). An Fc molecule of FcΔ16 (+,K,CC) can dimerize with a molecule comprising an Fc region comprising a ten-amino acid hinge deletion and a negatively charged pair mutation such as FcΔ16(−, CC) (e.g., a GDF15 molecule comprising an Fc region of FcΔ16 (−, CC)). An Fc molecule of FcΔ16(+,K) can dimerize with a molecule comprising an Fc region comprising a ten-amino acid hinge deletion and a negatively charged pair mutation such as FcΔ16(−) (e.g., a GDF15 molecule comprising an Fc region of FcΔ16(+)). An Fc molecule of FcΔ10(+,K,L234A/L235A) can dimerize with a molecule comprising an Fc region comprising a ten-amino acid hinge deletion and a negatively charged pair mutation such as FcΔ10(−,L234A/L235A) (e.g., a GDF15 molecule comprising an Fc region of FcΔ10(−, L234A/L235A)).

Examples of GDF15 molecules that are GDF15-Fc fusion proteins are shown in Table 5.

TABLE 5

| GDF15 Molecules | | | | | |
|---|---|---|---|---|---|
| GDF15-Fc Fusion Protein | | | CDF15-Fc Fusion Protein Components SEQ ID NOs | | |
| SEQ ID NO. | Designation | Sequence | Fc Region | Linker | GDF15 Region |
| 38 | scFc-GDF15 | GGGERKSSVECPPCPAPPVA<br>GPSVFLFPPKPKDTLMISRT<br>PEVTCVVVDVSHEDPEVQF<br>NWYVDGVEVHNAKTKPRE<br>EQFNSTFRVVSVLTVVHQD<br>WLNGKEYKCKVSNKGLPA<br>PIEKTISKTKGQPREPQVYT<br>LPPSREEMTKNQVSLTCLV<br>KGFYPSDIAVEWESNGQPE<br>NNYKTTPPMLDSDGSFFLY<br>SKLTVDKSRWQQGNVFSCS<br>VMHEALHNHYTQKSLSLSP<br>GGGGGSGGGGSGGGGSGG<br>GGSGGGGSGGGGSGGGGS<br>GGGGSERKSSVECPPCPAPP<br>VAGPSVFLFPPKPKDTLMIS<br>RTPEVTCVVVDVSHEDPEV<br>QFNWYVDGVEVHNAKTKP<br>REEQFNSTFRVVSVLTVVH<br>QDWLNGKEYKCKVSNKGL<br>PAPIEKTISKTKGQPREPQV<br>YTLPPSREEMTKNQVSLTC<br>LVKGFYPSDIAVEWESNGQ<br>PENNYKTTPPMLDSDGSFFL<br>YSKLTVDKSRWQQGNVFS<br>CSVMHEALHNHYTQKSLSL<br>SPGSGGGGSGGGGSGGGGS<br>GGGGSARNGDHCPLGPGRC<br>CRLHTVRASLEDLGWADW<br>VLSPREVQVTMCIGACPSQF<br>RAANMHAQIKTSLHRLKPD<br>TVPAPCCVPASYNPMVLIQ<br>KTDTGVSLQTYDDLLAKDC<br>HCI | — | — | — |
| 39 | FcΔ10(-)-(G4S)4-GDF15 | APELLGGPSVFLFPPKPKDT<br>LMISRTPEVTCVVVDVSHE<br>DPEVKFNWYVDGVEVHNA<br>KTKPREEQYNSTYRVVSVL<br>TVLHQDWLNGKEYKCKVS<br>NKALPAPIEKTISKAKGQPR<br>EPQVYTLPPSREEMTKNQV<br>SLTCLVKGFYPSDIAVEWES<br>NGQPENNY**D**TTPPVLDSDG<br>SFFLYS**D**LTVDKSRWQQGN<br>VFSCSVMHEALHNHYTQKS<br>LSLSPGGGGGSGGGGSGGG<br>GSGGGGSARNGDHCPLGPG<br>RCCRLHTVRASLEDLGWA<br>DWVLSPREVQVTMCIGACP<br>SQFRAANMHAQIKTSLHRL<br>KPDTVPAPCCVPASYNPMV<br>LIQKTDTGVSLQTYDDLLA<br>KDCHCI<br>Underlined and bolded residues are K392D and K409D mutations. | 26 | 21 | 6 |
| 40 | FcΔ10(+)-(G4)-GDF15 | APELLGGPSVFLFPPKPKDT<br>LMISRTPEVTCVVVDVSHE<br>DPEVKFNWYVDGVEVHNA<br>KTKPREEQYNSTYRVVSVL<br>TVLHQDWLNGKEYKCKVS<br>NKALPAPIEKTISKAKGQPR<br>EPQVYTLPPSR**K**EMTKNQV<br>SLTCLVKGFYPSDIAVEWES<br>NGQPENNYKTTPPVL**K**SDG<br>SFFLYSKLTVDKSRWQQGN | 27 | 23 | 6 |

TABLE 5-continued

| GDF15 Molecules | | | | | |
|---|---|---|---|---|---|
| GDF15-Fc Fusion Protein | | | CDF15-Fc Fusion Protein Components SEQ ID NOs | | |
| SEQ ID NO. | Designation | Sequence | Fc Region | Linker | GDF15 Region |
| | | VFSCSVMHEALHNHYTQKS LSLSPGGGGGARNGDHCPL GPGRCCRLHTVRASLEDLG WADWVLSPREVQVTMCIG ACPSQFRAANMHAQIKTSL HRLKPDTVPAPCCVPASYN PMVLIQKTDTGVSLQTYDD LLAKDCHCI Underlined and bolded residues are E356K and D399K mutations. | | | |
| 41 | FcΔ10(-)-GDF15(43) | APELLGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNYDTTPPVLDSDG SFFLYSDLTVDKSRWQQGN VFSCSVMHEALHNHYTQKS LSLSPGGDHCPLGPGRCCRL HTVRASLEDLGWADWVLS PREVQVTMCIGACPSQFRA ANMHAQIKTSLHRLKPDTV PAPCCVPASYNPMVLIQKT DTGVSLQTYDDLLAKDCHC I Underlined and bolded residues are K392D and K409D mutations. | 26 | — | 13 |
| 42 | FcΔ10(-)-GDF15(N3 D) | APELLGGSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNYDTTPPVLDSDG SFFLYSDLTVDKSRWQQGN VFSCSVMHEALHNHYTQKS LSLSPGARDGDHCPLGPGR CCRLHTVRASLEDLGWAD WVLSPREVQVTMCIGACPS QFRAANMHAQIKTSLHRLK PDTVPAPCCVPASYNPMVLI QKTDTGVSLQTYDDLLAKD CHCI Underlined and bolded residues are K392D and K409D mutations. | 26 | — | 15 |
| 43 | FcΔ10(-, CC)-GDF15(Δ3) | APELLGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVCTLPPSREEMTKNQV SLTCLVKGFYPSDIAVEWES NGQPENNYDTTPPVLDSDG SFFLYSDLTVDKSRWQQGN VFSCSVMHEALHNHYTQKS LSLSPGGDHCPLGPGRCCRL HTVRASLEDLGWADWVLS PREVQVTMCIGACPSQFRA ANMHAQIKTSLHRLKPDTV | 28 | — | 13 |

TABLE 5-continued

| GDF15 Molecules | | | | | |
|---|---|---|---|---|---|
| GDF15-Fc Fusion Protein | | | CDF15-Fc Fusion Protein Components SEQ ID NOs | | |
| SEQ ID NO. | Designation | Sequence | Fc Region | Linker | GDF15 Region |
| | | PAPCCVPASYNPMVLIQKT DTGVSLQTYDDLLAKDCHC I Underlined and italicized residue is Y349C mutation; underlined and bolded residues are K392D and K409D mutations. | | | |
| 44 | FcΔ10(-, CC)-GDF15(N3 D) | APELLGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVCTLPPSREEMTKNQV SLTCLVKGFYPSDIAVEWES NGQPENNYDTTPPVLDSDG SFFLYSDLTVDKSRWQQGN VFSCSVMHEALHNHYTQKS LSLSPGARDGDHCPLGPGR CCRLHTVRASLEDLGWAD WVLSPREVQVTMCIGACPS QFRAANMHAQIKTSLHRLK PDTVPAPCCVPASYNPMVLI QKTDTGVSLQTYDDLLAKD CHCI Underlined and italicized residue is Y349C mutation; underlined and bolded residues are K392D and K409D mutations. | 28 | — | 15 |
| 45 | FcΔ16(-, CC)-GDF15(Δ3/ D5E) | GPSVFLFPPKPKDTLMISRT PEVTCVVVDVSHEDPEVKF NWYVDGVEVHNAKTKPRE EQYNSTYRVVSVLTVLHQD WLNGKEYKCKVSNKALPA PIEKTISKAKGQPREPQVCT LPPSREEMTKNQVSLTCLV KGFYPSDIAVEWESNGQPE NNYDTTPPVLDSDGSFFLYS DLTVDKSRWQQGNVFSCS VMHEALHNHYTQKSLSLSP GGEHCPLGPGRCCRLHTVR ASLEDLGWADWVLSPREV QVTMCIGACPSQFRAANMH AQIKTSLHRLKPDTVPAPCC VPASYNPMVLIQKTDTGVS LQTYDDLLAKDCHCI Underlined and italicized residue is Y349C mutation; underlined and bolded residues are K392D and K409D mutations. | 29 | — | 17 |
| 46 | FcΔ16(-, CC)-GDF15(N3 Q/D5E) | GPSVFLFPPKPKDTLMISRT PEVTCVVVDVSHEDPEVKF NWYVDGVEVHNAKTKPRE EQYNSTYRVVSVLTVLHQD WLNGKEYKCKVSNKALPA PIEKTISKAKGQPREPQVCT LPPSREEMTKNQVSLTCLV KGFYPSDIAVEWESNGQPE NNYDTTPPVLDSDGSFFLYS DLTVDKSRWQQGNVFSCS VMHEALHNHYTQKSLSLSP GARQGEHCPLGPGRCCRLH TVRASLEDLGWADWVLSP REVQVTMCIGACPSQFRAA NMHAQIKTSLHRLKPDTVP | 29 | — | 18 |

TABLE 5-continued

GDF15 Molecules

| GDF15-Fc Fusion Protein | | | CDF15-Fc Fusion Protein Components SEQ ID NOs | | |
|---|---|---|---|---|---|
| SEQ ID NO. | Designation | Sequence | Fc Region | Linker | GDF15 Region |
| | | APCCVPASYNPMVLIQKTD<br>TGVSLQTYDDLLAKDCHCI<br>Underlined and italicized residue is Y349C mutation; underlined and bolded residues are K392D and K409D mutations. | | | |
| 47 | FcΔ16(-)-GDF15(N3Q/D5E) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GARQGEHCPLGPGRCCRLH<br>TVRASLEDLGWADWVLSP<br>REVQVTMCIGACPSQFRAA<br>NMHAQIKTSLHRLKPDTVP<br>APCCVPASYNPMVLIQKTD<br>TGVSLQTYDDLLAKDCHCI<br>Underlined and bolded residues are K392D and K409D mutations. | 30 | — | 18 |
| 48 | FcΔ16(-)-(G4Q)4-GDF15 | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGQGGGGQGGGGQG<br>GGGQARNGDHCPLGPGRC<br>CRLHTVRASLEDLGWADW<br>VLSPREVQVTMCIGACPSQF<br>RAANMHAQIKTSLHRLKPD<br>TVPAPCCVPASYNPMVLIQ<br>KTDTGVSLQTYDDLLAKDC<br>HCI<br>Underlined and bolded residues are K392D and K409D mutations. | 30 | 25 | 6 |
| 49 | FcΔ16(-)-(G4Q)4-GDF15(N3Q) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGQGGGGQGGGGQG<br>GGGQARQGDHCPLGPGRC<br>CRLHTVRASLEDLGWADW | 30 | 25 | 14 |

TABLE 5-continued

| GDF15 Molecules | | | | | |
|---|---|---|---|---|---|
| GDF15-Fc Fusion Protein | | | CDF15-Fc Fusion Protein Components SEQ ID NOs | | |
| SEQ ID NO. | Designation | Sequence | Fc Region | Linker | GDF15 Region |
| | | VLSPREVQVTMCIGACPSQF<br>RAANMHAQIKTSLHRLKPD<br>TVPAPCCVPASYNPMVLIQ<br>KTDTGVSLQTYDDLLAKDC<br>HCI<br>Underlined and bolded residues are K392D and K409D mutations. | | | |
| 50 | FcΔ16(-)-(G4Q)4-GDF15(N3Q/D5E) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGQGGGGQGGGGQG<br>GGGQARQGEHCPLGPGRCC<br>RLHTVRASLEDLGWADWV<br>LSPREVQVTMCIGACPSQFR<br>AANMHAQIKTSLHRLKPDT<br>VPAPCCVPASYNPMVLIQK<br>TDTGVSLQTYDDLLAKDCH<br>CI<br>Underlined and bolded residues are K392D and K409D mutations. | 30 | 25 | 18 |
| 51 | FcΔ16(-)-(G4S)2-GDF15(N3Q) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGSGGGGSARQGDHC<br>PLGPGRCCRLHTVRASLED<br>LGWADWVLSPREVQVTMC<br>IGACPSQFRAANMHAQIKT<br>SLHRLKPDTVPAPCCVPAS<br>YNPMVLIQKTDTGVSLQTY<br>DDLLAKDCHCI<br>Underlined and bolded residues are K392D and K409D mutations. | 30 | 20 | 14 |
| 52 | FcΔ16(-)-(G4S)2-GDF15(N3Q/D5E) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGSGGGGSARQGEHC<br>PLGPGRCCRLHTVRASLED<br>LGWADWVLSPREVQVTMC | 30 | 20 | 18 |

TABLE 5-continued

| GDF15 Molecules | | | | | |
|---|---|---|---|---|---|
| GDF15-Fc Fusion Protein | | | CDF15-Fc Fusion Protein Components SEQ ID NOs | | |
| SEQ ID NO. | Designation | Sequence | Fc Region | Linker | GDF15 Region |
| | | IGACPSQFRAANMHAQIKT SLHRLKPDTVPAPCCVPAS YNPMVLIQKTDTGVSLQTY DDLLAKDCHCI Underlined and bolded residues are K392D and K409D mutations. | | | |
| 53 | FcΔ16(-)-G4S-GDF15(N3Q) | GPSVFLFPPKPKDTLMISRT PEVTCVVVDVSHEDPEVKF NWYVDGVEVHNAKTKPRE EQYNSTYRVVSVLTVLHQD WLNGKEYKCKVSNKALPA PIEKTISKAKGQPREPQVYT LPPSREEMTKNQVSLTCLV KGFYPSDIAVEWESNGQPE NNY**D**TTPPVLDSDGSFFLYS **D**LTVDKSRWQQGNVFSCS VMHEALHNHYTQKSLSLSP GGGGGSARQGDHCPLGPG RCCRLHTVRASLEDLGWA DWVLSPREVQVTMCIGACP SQFRAANMHAQIKTSLHRL KPDTVPAPCCVPASYNPMV LIQKTDTGVSLQTYDDLLA KDCHCI Underlined and bolded residues are K392D and K409D mutations. | 30 | 19 | 14 |
| 54 | FcΔ16(-)-G4S-GDF15(N3Q/D5E) | GPSVFLFPPKPKDTLMISRT PEVTCVVVDVSHEDPEVKF NWYVDGVEVHNAKTKPRE EQYNSTYRVVSVLTVLHQD WLNGKEYKCKVSNKALPA PIEKTISKAKGQPREPQVYT LPPSREEMTKNQVSLTCLV KGFYPSDIAVEWESNGQPE NNY**D**TTPPVLDSDGSFFLYS **D**LTVDKSRWQQGNVFSCS VMHEALHNHYTQKSLSLSP GGGGGSARQGEHCPLGPGR CCRLHTVRASLEDLGWAD WVLSPREVQVTMCIGACPS QFRAANMHAQIKTSLHRLK PDTVPAPCCVPASYNPMVLI QKTDTGVSLQTYDDLLAKD CHCI Underlined and bolded residues are K392D and K409D mutations. | 30 | 19 | 18 |
| 55 | FcΔ16(-)-GDF15(N3Q) | GPSVFLFPPKPKDTLMISRT PEVTCVVVDVSHEDPEVKF NWYVDGVEVHNAKTKPRE EQYNSTYRVVSVLTVLHQD WLNGKEYKCKVSNKALPA PIEKTISKAKGQPREPQVYT LPPSREEMTKNQVSLTCLV KGFYPSDIAVEWESNGQPE NNY**D**TTPPVLDSDGSFFLYS **D**LTVDKSRWQQGNVFSCS VMHEALHNHYTQKSLSLSP GARQGDHCPLGPGRCCRLH TVRASLEDLGWADWVLSP | 30 | — | 14 |

TABLE 5-continued

| GDF15 Molecules | | | | | |
|---|---|---|---|---|---|
| GDF15-Fc Fusion Protein | | | CDF15-Fc Fusion Protein Components SEQ ID NOs | | |
| SEQ ID NO. | Designation | Sequence | Fc Region | Linker | GDF15 Region |
| | | REVQVTMCIGACPSQFRAA NMHAQIKTSLHRLKPDTVP APCCVPASYNPMVLIQKTD TGVSLQTYDDLLAKDCHCI Underlined and bolded residues are K392D and K409D mutations. | | | |
| 56 | FcΔ10(-, L234A/L235A)-(G4Q)4-GDF15(N3Q) | APEAAGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNY**D**TTPPVLDSDG SFFLYS**D**LTVDKSRWQQGN VFSCSVMHEALHNHYTQKS LSLSPGGGGGQGGGGQGG GGQGGGGQARQGDHCPLG PGRCCRLHTVRASLEDLGW ADWVLSPREVQVTMCIGAC PSQFRAANMHAQIKTSLHR LKPDTVPAPCCVPASYNPM VLIQKTDTGVSLQTYDDLL AKDCHCI Underlined and italicized residues are L234A and L235A mutations; underlined and bolded residues are K392D and K409D mutations. | 31 | 25 | 14 |
| 57 | Fc1810(-, L234A/L235A)-(G4Q)4-GDF15(N3Q/D5E) | APEAAGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNY**D**TTPPVLDSDG SFFLYS**D**LTVDKSRWQQGN VFSCSVMHEALHNHYTQKS LSLSPGGGGGQGGGGQGG GGQGGGGQARQGEHCPLG PGRCCRLHTVRASLEDLGW ADWVLSPREVQVTMCIGAC PSQFRAANMHAQIKTSLHR LKPDTVPAPCCVPASYNPM VLIQKTDTGVSLQTYDDLL AKDCHCI Underlined and italicized residues are L234A and L235A mutations; underlined and bolded residues are K392D and K409D mutations. | 31 | 25 | 18 |

In some embodiments, the fusion protein is an scFc-GDF15 in which the GDF15 region is joined to two Fc regions. In some embodiments, the fusion protein comprises an amino acid sequence that has at least 85%, 90%, 95% or 99% sequence identity to SEQ ID NO: 38. In some embodiments, the fusion protein comprises an amino acid sequence of SEQ ID NO: 38. In calculating percent sequence identity, the sequences being compared are aligned in a way that gives the largest match between the sequences. A computer program that can be used to determine percent identity is the GCG program package, which includes GAP (Devereux et al., (1984) Nucl. Acid Res. 12:387; Genetics Computer Group, University of Wisconsin, Madison, Wis.). The computer algorithm GAP can be used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992) Proc. Natl. Acad. Sci. U.S.A. 9:10915-10919 for the BLOSUM 62 comparison matrix) is also used by the algorithm. Parameters that can be used for determining percent identity using the GAP program are the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

In some embodiments, the GDF15 molecule is FcΔ10(−)-(G4S)4-GDF15, FcΔ10(+)-(G4)-GDF15, FcΔ10(−)-GDF15(Δ3), FcΔ10(−)-GDF15(N3D), FcΔ10(−,CC)-GDF15(Δ3), FcΔ10(−,CC)-GDF15(N3D), FcΔ16(−,CC)-GDF15(Δ3/D5E), FcΔ16(−,CC)-GDF15(N3Q/D5E), FcΔ16(−)-GDF15(N3Q/D5E), FcΔ16(−)-(G4Q)4-GDF15, FcΔ16(−)-(G4Q)4-GDF15(N3Q), FcΔ16(−)-(G4Q)4-GDF15(N3Q/D5E), FcΔ16(−)-(G4S)2-GDF15(N3Q), FcΔ16(−)-(G4S)2-GDF15(N3Q/D5E), FcΔ16(−)-G4S-GDF15(N3Q), FcΔ16(−)-G4S-GDF15(N3Q/D5E), FcΔ16(−)-GDF15(N3Q), FcΔ10(−,L234A/L235A)-(G4Q)4-GDF15(N3Q), or FcΔ10(−,L234A/L235A)-(G4Q)4-GDF15(N3Q/D5E).

In some embodiments, the GDF15 molecule comprises the amino acid sequence of SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 85% sequence identity to SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 90% sequence identity to SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 95% sequence identity to SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 99% sequence identity to SEQ ID NO: 39, 40, 41, 42, 43, 44, 45, 46, 47, 48, 49, 50, 51, 52, 53, 54, 55, 56, or 57.

In some embodiments, the GDF15 molecule is a FcΔ10(−)-(G4S)4-GDF15, FcΔ10(+)-(G4)-GDF15, FcΔ10(−)-GDF15(A3), FcΔ10(−)-GDF15(N3D), FcΔ10(−,CC)-GDF15(A3), FcΔ10(−,CC)-GDF15(N3D), FcΔ16(−,CC)-GDF15(A3/D5E), FcΔ16(−,CC)-GDF15(N3Q/D5E), FcΔ16(−)-GDF15(N3Q/D5E), FcΔ16(−)-(G4Q)4-GDF15, FcΔ16(−)-(G4Q)4-GDF15(N3Q), FcΔ16(−)-(G4Q)4-GDF15(N3Q/D5E), FcΔ16(−)-(G4S)2-GDF15(N3Q), FcΔ16(−)-(G4S)2-GDF15(N3Q/D5E), FcΔ16(−)-G4S-GDF15(N3Q), FcΔ16(−)-G4S-GDF15(N3Q/D5E), FcΔ16(−)-GDF15(N3Q), FcΔ10(−,L234A/L235A)-(G4Q)4-GDF15(N3Q), or FcΔ10(−,L234A/L235A)-(G4Q)4-GDF15(N3Q/D5E) molecule that has at least 85%, 90%, 95% or 99% sequence identity to its Fc region and/or GDF15 region. For example, a FcΔ10(−)-(G4S)4-GDF15 molecule with at least 85%, 90%, 95% or 99% sequence identity to its Fc region and/or GDF15 region, includes a GDF15 molecule with an Fc region that has a ten-amino acid deletion of the hinge region and a negatively charged pair mutation, and has at least 85%, 90%, 95% or 99% sequence identity to SEQ ID NO: 26 and/or a GDF15 region that has at least 85%, 90%, 95% or 99% sequence identity to SEQ ID NO: 6. In another example, a FcΔ16(−)-(G4Q)4-GDF15(N3Q/D5E) molecule with at least 85%, 90%, 95% or 99% sequence identity to its Fc region and/or a GDF15 region, includes a GDF15 molecule with an Fc region that has a sixteen-amino acid deletion of the hinge region and a negatively charged pair mutation that has at least 85%, 90%, 95% or 99% sequence identity to SEQ ID NO: 30 and/or a GDF15 region that has at least 85%, 90%, 95% or 99% sequence identity to SEQ ID NO: 18. In yet another example, a FcΔ10(−,L234A/L235A)-(G4Q)4-GDF15(N3Q/D5E) molecule with at least 85%, 90%, 95% or 99% sequence identity to its Fc region and/or a GDF15 region, includes a GDF15 molecule with an Fc region that has a ten-amino acid deletion of the hinge region, a negatively charged pair mutation and leucine to alanine mutations at positions 234 and 235 and has at least 85%, 90%, 95% or 99% sequence identity to SEQ ID NO: 31 and/or a GDF15 region that has at least 85%, 90%, 95% or 99% sequence identity to SEQ ID NO: 18.

Also provided herein are dimers and tetramers comprising a GDF15 molecule provided herein. In one embodiment, the dimer comprises a GDF15-Fc fusion comprising the amino acid sequence of any one of SEQ ID NOs: 39-57. In some embodiments, a GDF15-Fc fusion comprising the amino acid sequence of SEQ ID NO: 39, 40, 41, 42, 43, 44, 45, 46, 47, 48, 49, 50, 51, 52, 53, 54, 55, 56 or 57 dimerizes with an Fc molecule comprising the amino acid sequence of SEQ ID NO: 32, 33, 34, 35, 36, or 37 (in which the C-terminal lysine is optional), such as shown in Table 6. For example, in some embodiments, the dimer is FcΔ10(−)-(G4S)4-GDF15: FcΔ10(+,K). In another embodiment, the dimer is FcΔ10(−,L234A/L235A)-(G4Q)4-GDF15(N3Q): FcΔ10(+,K,L234A/L235A). In yet another embodiment, the dimer is FcΔ10(−,L234A/L235A)-(G4Q)4-GDF15(N3Q):FcΔ10(+,K,L234A/L235A).

TABLE 6

| Dimers | | | |
|---|---|---|---|
| GDF15-Fc Fusion SEQ ID NO. | GDF15-Fc Fusion Designation | Fc Molecule SEQ ID NO. | Corresponding Fc Molecule Designation |
| 39 | FcΔ10(−)-(G4S)4-GDF15 | 32 | FcΔ10(+, K) |
| 40 | FcΔ10(+)-(G4)-GDF15 | 33 | FcΔ10(−, K) |
| 41 | FcΔ10(−)-GDF15(Δ3) | 32 | FcΔ10(+, K) |
| 42 | FcΔ10(−)-GDF15(N3D) | 32 | FcΔ10(+, K) |
| 43 | FcΔ10(−, CC)-GDF15(Δ3) | 34 | FcΔ10(+, K, CC) |
| 44 | FcΔ10(−, CC)-GDF15(N3D) | 34 | FcΔ10(+, K, CC) |
| 45 | FcΔ16(−, CC)-GDF15(Δ3/D5E) | 35 | FcΔ16(+, K, CC) |
| 46 | FcΔ16(−, CC)-GDF15(N3Q/D5E) | 35 | FcΔ16(+, K, CC) |

TABLE 6-continued

Dimers

| GDF15-Fc Fusion SEQ ID NO. | GDF15-Fc Fusion Designation | Fc Molecule SEQ ID NO. | Corresponding Fc Molecule Designation |
|---|---|---|---|
| 47 | FcΔ16(−)-GDF15(N3Q/D5E) | 36 | FcΔ16(+, K) |
| 48 | FcΔ16(−)-(G4Q)4-GDF15 | 36 | FcΔ16(+, K) |
| 49 | FcΔ16(−)-(G4Q)4-GDF15(N3Q) | 36 | FcΔ16(+, K) |
| 50 | FcΔ16(−)-(G4Q)4-GDF15(N3Q/D5E) | 36 | FcΔ16(+, K) |
| 51 | FcΔ16(−)-(G4S)2-GDF15(N3Q) | 36 | FcΔ16(+, K) |
| 52 | FcΔ16(−)-(G4S)2-GDF15(N3Q/D5E) | 36 | FcΔ16(+, K) |
| 53 | FcΔ16(−)-G4S-GDF15(N3Q) | 36 | FcΔ16(+, K) |
| 54 | FcΔ16(−)-G4S-GDF15(N3Q/D5E) | 36 | FcΔ16(+, K) |
| 55 | FcΔ16(−)-GDF15(N3Q) | 36 | FcΔ16(+, K) |
| 56 | FcΔ10(−, L234A/L235A)-(G4Q)4-GDF15(N3Q) | 37 | FcΔ10(+, K, L234A/L235A) |
| 57 | FcΔ10(−, L234A/L235A)-(G4Q)4-GDF15(N3Q/D5E) | 37 | FcΔ10(+, K, L234A/L235A) |

In one embodiment, a GDF15-Fc fusion comprising the amino acid sequence of SEQ ID NO: 39 dimerizes with an Fc molecule comprising SEQ ID NO: 32 (C-terminal lysine optional). In another embodiment, a GDF15-Fc fusion comprising the amino acid sequence of SEQ ID NO: 40 dimerizes with an Fc molecule comprising SEQ ID NO: 33 (C-terminal lysine optional). In another embodiment, a GDF15-Fc fusion comprising the amino acid sequence of SEQ ID NO: 41 dimerizes with an Fc molecule comprising SEQ ID NO: 32 (C-terminal lysine optional). In another embodiment, a GDF15-Fc fusion comprising the amino acid sequence of SEQ ID NO: 42 dimerizes with an Fc molecule comprising SEQ ID NO: 32 (C-terminal lysine optional). In another embodiment, a GDF15-Fc fusion comprising the amino acid sequence of SEQ ID NO: 43 dimerizes with an Fc molecule comprising SEQ ID NO: 34 (C-terminal lysine optional). In another embodiment, a GDF15-Fc fusion comprising the amino acid sequence of SEQ ID NO: 44 dimerizes with an Fc molecule comprising SEQ ID NO: 34 (C-terminal lysine optional). In another embodiment, a GDF15-Fc fusion comprising the amino acid sequence of SEQ ID NO: 44 dimerizes with an Fc molecule comprising SEQ ID NO: 34 (C-terminal lysine optional). In another embodiment, a GDF15-Fc fusion comprising the amino acid sequence of SEQ ID NO: 45 dimerizes with an Fc molecule comprising SEQ ID NO: 35 (C-terminal lysine optional). In another embodiment, a GDF15-Fc fusion comprising the amino acid sequence of SEQ ID NO: 46 dimerizes with an Fc molecule comprising SEQ ID NO: 35 (C-terminal lysine optional). In another embodiment, a GDF15-Fc fusion comprising the amino acid sequence of SEQ ID NO: 47 dimerizes with an Fc molecule comprising SEQ ID NO: 36 (C-terminal lysine optional). In another embodiment, a GDF15-Fc fusion comprising the amino acid sequence of SEQ ID NO: 48 dimerizes with an Fc molecule comprising SEQ ID NO: 36 (C-terminal lysine optional). In another embodiment, a GDF15-Fc fusion comprising the amino acid sequence of SEQ ID NO: 49 dimerizes with an Fc molecule comprising SEQ ID NO: 36 (C-terminal lysine optional). In another embodiment, a GDF15-Fc fusion comprising the amino acid sequence of SEQ ID NO: 50 dimerizes with an Fc molecule comprising SEQ ID NO: 36 (C-terminal lysine optional). In another embodiment, a GDF15-Fc fusion comprising the amino acid sequence of SEQ ID NO: 51 dimerizes with an Fc molecule comprising SEQ ID NO: 36 (C-terminal lysine optional). In another embodiment, a GDF15-Fc fusion comprising the amino acid sequence of SEQ ID NO: 52 dimerizes with an Fc molecule comprising SEQ ID NO: 36 (C-terminal lysine optional). In another embodiment, a GDF15-Fc fusion comprising the amino acid sequence of SEQ ID NO: 53 dimerizes with an Fc molecule comprising SEQ ID NO: 36 (C-terminal lysine optional). In another embodiment, a GDF15-Fc fusion comprising the amino acid sequence of SEQ ID NO: 54 dimerizes with an Fc molecule comprising SEQ ID NO: 36 (C-terminal lysine optional). In another embodiment, a GDF15-Fc fusion comprising the amino acid sequence of SEQ ID NO: 55 dimerizes with an Fc molecule comprising SEQ ID NO: 36 (C-terminal lysine optional). In another embodiment, a GDF15-Fc fusion comprising the amino acid sequence of SEQ ID NO: 56 dimerizes with an Fc molecule comprising SEQ ID NO: 37 (C-terminal lysine optional). In another embodiment, a GDF15-Fc fusion comprising the amino acid sequence of SEQ ID NO: 57 dimerizes with an Fc molecule comprising SEQ ID NO: 37 (C-terminal lysine optional).

In some embodiments, the dimers form tetramers. For example, the dimers in Table 6 can form tetramers. In some embodiments, the tetramers are formed form the same dimers. In some embodiments, two dimers of FcΔ10(−)-(G4S)4-GDF15:FcΔ10(+,K); FcΔ10(+)-(G4)-GDF15:FcΔ10(−,K); FcΔ10(−)-GDF15(Δ3):FcΔ10(+,K); FcΔ10(−)-GDF15(N3D):FcΔ10(+,K); FcΔ10(−,CC)-GDF15(Δ3):FcΔ10(+,K,CC); FcΔ10(−,CC)-GDF15(N3D):FcΔ10(+,K,CC); FcΔ16(−,CC)-GDF15(Δ3/D5E):FcΔ16(+,K,CC); FcΔ16(−,CC)-GDF15(N3Q/D5E):FcΔ16(+,K,CC); FcΔ16(−)-GDF15(N3Q/D5E):FcΔ16(+,K); FcΔ16(−)-(G4Q)4-GDF15:FcΔ16(+,K); FcΔ16(−)-(G4Q)4-GDF15(N3Q):FcΔ16(+,K); FcΔ16(−)-(G4Q)4-GDF15(N3Q/D5E):FcΔ16(+,K); FcΔ16(−)-(G4S)2-GDF15(N3Q):FcΔ16(+,K); FcΔ16(−)-(G4S)2-GDF15(N3Q/D5E):FcΔ16(+,K); FcΔ16(−)-G4S-GDF15(N3Q):FcΔ16(+,K); FcΔ16(−)-G4S-GDF15(N3Q/D5E): FcΔ16(+,K); FcΔ16(−)-GDF15(N3Q): FcΔ16(+,K); FcΔ10(−,L234A/L235A)-(G4Q)4-GDF15(N3Q):FcΔ10(+,K,L234A/L235A); or FcΔ10(−,L234A/L235A)-(G4Q)4-GDF15(N3Q/D5E):FcΔ10(+,K,L234A/L235A) form a tetramer, such as through the dimerization of the two GDF15 regions.

Also provided herein are host cells comprising the nucleic acids and vectors for producing the GDF15 and Fc molecules disclosed herein. In various embodiments, the vector or nucleic acid is integrated into the host cell genome, which in other embodiments the vector or nucleic acid is extra-chromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments, cells comprising a non-integrated nucleic acid, such as a plasmid, cosmid, phagemid, or linear expression element, which comprises a sequence coding for expression of a GDF15 molecule and/or an Fc molecule. In some embodiments, the cell comprises a nucleic acid for producing a GDF15 molecule and another cell comprises a nucleic acid for producing an Fc molecule for dimerization with the GDF15 molecule (e.g., a vector for encoding a GDF15 molecule in one cell and a second vector for encoding an Fc molecule in a second cell). In other embodiments, a host cell comprises a nucleic acid for producing a GDF15 molecule and an Fc molecule (e.g., a vector that encodes both molecules). In another embodiment, a host cell comprises a nucleic acid for producing a GDF15 molecule and another nucleic acid for producing an Fc molecule (e.g., two separate vectors, one that encodes a GDF15 molecule and one that encodes an Fc molecule, in a single host cell)

A vector comprising a nucleic acid sequence encoding a GDF15 molecule and/or an Fc molecule can be introduced into a host cell by transformation or by transfection, such as by methods known in the art.

A nucleic acid encoding a GDF15 molecule can be positioned in and/or delivered to a host cell or host animal via a viral vector. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a nucleic acid encoding a polypeptide comprising a GDF15 region. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

A GDF15 molecule can be isolated using standard protein purification methods. A polypeptide comprising a GDF15 region can be isolated from a cell that has been engineered to express a polypeptide comprising a GDF15 region, for example a cell that does not naturally express native GDF15. Protein purification methods known in the art can be employed to isolate GDF15 molecules, as well as associated materials and reagents. Methods of purifying a GDF15 molecule are also provided in the Examples herein. Additional purification methods that may be useful for isolating GDF15 molecules can be found in references such as Bootcov M R, 1997, *Proc. Natl. Acad. Sci. USA* 94:11514-9, Fairlie W D, 2000, *Gene* 254: 67-76.

Pharmaceutical compositions comprising a GDF15 molecule (and optionally, an Fc molecule, such as a dimer or tetramer disclosed herein) are also provided. Such polypeptide pharmaceutical compositions can comprise a therapeutically effective amount of a GDF15 molecule in admixture with a pharmaceutically or physiologically acceptable formulation agent or carrier selected for suitability with the mode of administration. The pharmaceutically or physiologically acceptable formulation agent can be one or more formulation agents suitable for accomplishing or enhancing the delivery of a GDF15 molecule into the body of a human or non-human subject. Pharmaceutically acceptable substances such as wetting or emulsifying agents, preservatives or buffers, which enhance the shelf life or effectiveness of the GDF15 molecule can also act as, or form a component of, a formulation carrier. Acceptable pharmaceutically acceptable carriers are preferably nontoxic to recipients at the dosages and concentrations employed. The pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition.

The effective amount of pharmaceutical composition comprising a GDF15 molecule which is to be employed therapeutically will depend, for example, upon the therapeutic context and objectives. One skilled in the art will appreciate that the appropriate dosage levels for treatment will thus vary depending, in part, upon the molecule delivered, the indication for which a GDF15 molecule is being used, the route of administration, and the size (body weight, body surface, or organ size) and condition (the age and general health) of the subject. The frequency of dosing will depend upon the pharmacokinetic parameters of the GDF15 molecule in the formulation being used.

The route of administration of the pharmaceutical composition can be orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by an implantation device. The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

A GDF15 molecule can be used to treat, diagnose or ameliorate, a metabolic condition or disorder. In one embodiment, the metabolic disorder is diabetes, e.g., type 2 diabetes. In another embodiment, the metabolic condition or disorder is obesity. In other embodiments, the metabolic condition or disorder is dyslipidemia, elevated glucose levels, elevated insulin levels or diabetic nephropathy. For example, a metabolic condition or disorder that can be treated or ameliorated using a GDF15 molecule includes a state in which a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a GDF15 molecule can also be found in the American Diabetes Association Standards of Medical Care in Diabetes Care-2011, American Diabetes Association, Diabetes Care Vol. 34, No. Supplement 1, S11-S61, 2010.

The administration can be performed such as by IV injection, intraperitoneal (IP) injection, subcutaneous injection, intramuscular injection, or orally in the form of a tablet or liquid formation. A therapeutically effective dose of a GDF15 molecule will depend upon the administration schedule, the unit dose of agent administered, whether the GDF15 molecule is administered in combination with other therapeutic agents, the immune status and the health of the recipient. A therapeutically effective dose is an amount of a GDF15 molecule that elicits a biological or medicinal response in a tissue system, animal, or human being sought by a researcher, medical doctor, or other clinician, which includes alleviation or amelioration of the symptoms of the disease or disorder being treated, i.e., an amount of a GDF15 molecule that supports an observable level of one or more desired biological or medicinal response, for example, lowering blood glucose, insulin, triglyceride, or cholesterol levels; reducing body weight; or improving glucose tolerance, energy expenditure, or insulin sensitivity; or reducing food intake. A therapeutically effective dose of a GDF15 molecule can also vary with the desired result.

Also provided herein is a method comprising measuring a baseline level of one or more metabolically-relevant compounds such as glucose, insulin, cholesterol, lipid in a subject, administering a pharmaceutical composition comprising a GDF15 molecule to the subject, and after a desired period of time, measure the level of the one or more metabolically-relevant compounds (e.g., blood glucose, insulin, cholesterol, lipid) in the subject. The two levels can then be compared to determine the relative change in the metabolically-relevant compound in the subject. Depending on the outcome of that comparison another dose of the pharmaceutical composition can be administered to achieve a desired level of one or more metabolically-relevant compound.

A GDF15 molecule (and optionally, its corresponding Fc molecule) can be administered in combination with another therapeutic agent, such as an agent that lowers blood glucose, insulin, triglyceride, or cholesterol levels; lowers body weight; reduces food intake; improves glucose tolerance, energy expenditure, or insulin sensitivity; or any combination thereof (e.g., antidiabetic agent, hypolipidemic agent, anti-obesity agent, anti-hypertensive agent, or agonist of peroxisome proliferator-activator receptor). For example, the agent can be selected from insulin, insulin derivatives and mimetics; insulin secretagogues; glyburide, Amaryl; insulinotropic sulfonylurea receptor ligands; thiazolidinediones, pioglitazone, balaglitazone, rivoglitazone, netoglitazone, troglitazone, englitazone, ciglitazone, adaglitazone, darglitazone, Cholesteryl ester transfer protein (CETP) inhibitors, GSK3 (glycogen synthase kinase-3) inhibitors; RXR ligands; sodium-dependent glucose cotransporter inhibitors; glycogen phosphorylase A inhibitors; biguanides; alpha-glucosidase inhibitors, GLP-1 (glucagon like peptide-1), GLP-1 analogs, GLP-1 mimetics; DPPIV (dipeptidyl peptidase IV) inhibitors, 3-hydroxy-3-methyl-glutaryl coenzyme A (HMG-CoA) reductase inhibitors; squalene synthase inhibitors; FXR (farnesoid X receptor), LXR (liver X receptor) ligands; cholestyramine; fibrates; nicotinic acid, aspirin; orlistat or rimonabant; loop diuretics, furosemide, torsemide; angiotensin converting enzyme (ACE) inhibitors; inhibitors of the Na—K-ATPase membrane pump; neutralendopeptidase (NEP) inhibitors; ACE/NEP inhibitors; angiotensin II antagonists; renin inhibitors; .beta.-adrenergic receptor blockers; inotropic agents, dobutamine, milrinone; calcium channel blockers; aldosterone receptor antagonists; aldosterone synthase inhibitors; fenofibrate, pioglitazone, rosiglitazone, tesaglitazar, BMS-298585 and L-796449.

The agent administered with a GDF15 molecule disclosed herein can be a GLP-1R agonist or a GIPR antagonist. A GLP-1R agonist can be a compound with GLP-1R activity. The GLP-1R agonist can be an exendin, exendin analog, or exendin agonist. Exendin includes naturally occurring (or synthetic versions of naturally occurring) exendin peptides that are found in the salivary secretions of the Gila monster. The exendin can be exendin-3: HSDGTFTSDLSKQMEEEAVRLFIEWLKNGGPSSGAPPPS-$NH_2$ (SEQ ID NO: 58); or exendin-4: HGEGTFTSDLSKQMEEEAVRLFIEWLKNGGPSSGAPPPS-$NH_2$ (SEQ ID NO: 59). The exendin, exendin analog, and exendin agonist described herein may optionally be amidated, in an acid form, in a pharmaceutically acceptable salt form, or any other physiologically active form. Synthetic exendin-4, also known as exenatide, is commercially available as BYETTA® (Amylin Pharmaceuticals, Inc. and Eli Lilly and Company). Other examples of exendin analogs and exendin agonists that can be used in combination with a GDF15 molecule disclosed herein are described in WO 98/05351; WO 99/07404; WO 99/25727; WO 99/25728; WO 99/40788; WO 00/41546; WO 00/41548; WO 00/73331; WO 01/51078; WO 03/099314; U.S. Pat. Nos. 6,956,026; 6,506,724; 6,703,359; 6,858,576; 6,872,700; 6,902,744; 7,157,555; 7,223,725; 7,220,721; US Publication No. 2003/0036504; US Publication No. 2006/0094652; and US Publication No. 2018/0311372, the disclosures of which are incorporated by reference herein in their entirety.

In one embodiment, the GLP-1R agonist is GLP-1 or analog thereof, such as GLP-1(7-37): HAEGTFTSDVSSYLEGQAAKEFIAWLVKGRG (SEQ ID NO: 60) or a GLP-1(7-37) analog. A GLP-1(7-37) analog can be a peptide that elicits a biological activity similar to that of GLP-1(7-37) when evaluated by art-known measures such as receptor binding assays or in vivo blood glucose assays as described, e.g., by Hargrove et al., *Regulatory Peptides,* 141:113-119 (2007), the disclosure of which is incorporated by reference herein. In one embodiment, a GLP-1(7-37) analog refers to a peptide that has an amino acid sequence with 1, 2, 3, 4, 5, 6, 7 or 8 amino acid substitutions, insertions, deletions, or a combination of two or more thereof, when compared to the amino acid sequence of GLP-1(7-37). In one embodiment, the GLP-1(7-37) analog is GLP-1(7-36)-$NH_2$. GLP-1(7-37) analogs include the amidated forms, the acid form, the pharmaceutically acceptable salt form, and any other physiologically active form of the molecule. In some embodiments a simple nomenclature is used to describe the GLP-1R agonist, e.g., [Aib8]GLP-1(7-37) designates an analogue of GLP-1(7-37) wherein the naturally occurring Ala in position 8 has been substituted with Aib. Other GLP-1(7-37) or GLP-1(7-37) analogs that can be used in combination with a GDF15 molecule disclosed herein include liraglutide (VICTOZA®, Novo Nordisk); albiglutide (SYNCRIA®, GlaxoSmithKline); taspoglutide (Hoffman La-Roche); dulaglutide (also known LY2189265; Eli Lilly and Company); or LY2428757 (Eli Lilly and Company). In one embodiment, the GLP-1R agonist is dulaglutide and comprises the amino acid sequence:

```
                                    (SEQ ID NO: 61)
HGEGTFTSDVSSYLEEQAAKEFIAWLVKGGGGGGGSGGGGSGGGGSAES

KYGPPCPPCPAPEAAGGPSVFLFPPKPKDTLMISRTPEVTCVVVDVSQE

DPEVQFNWYVDGVEVHNAKTKPREEQFNSTYRVVSVLTVHQDWLNGKEY

KCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRW

QEGNVFSCSVMHEALHNHYTQKSLSLSLG,
```

which optionally has a lysine at its C-terminus. One or more of the GLP-1 analogs described in U.S. Pat. Nos. 6,268,343; 7,452,966; and US Publication No. 2018/0311372, which is incorporated by reference herein in its entirety, can also be used in combination with a GDF15 molecule disclosed herein.

In one embodiment, a GDF15 molecule comprising the amino acid sequence of SEQ ID NO: 39, 40, 41, 42, 43, 44, 45, 46, 47, 48, 49, 50, 51, 52, 53, 54, 55, 56 or 57 is administered with a molecule comprising the amino acid sequence of SEQ ID NO: 58, 59, 60 or an amidated analog there. In one embodiment, a GDF15 molecule comprising the amino acid sequence of SEQ ID NO: 39, 40, 41, 42, 43, 44, 45, 46, 47, 48, 49, 50, 51, 52, 53, 54, 55, 56 or 57 is administered with dulaglutide, such as a molecule comprising the amino acid sequence of SEQ ID NO: 61.

In another embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; is administered with a molecule comprising the amino acid sequence of SEQ ID NO: 58, 59, 60 or an amidated analog there.

In another embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; is administered with dulaglutide, such as a molecule comprising the amino acid sequence of SEQ ID NO: 61.

In another embodiment, a GDF15 molecule and corresponding Fc molecule comprising the amino acid sequences of SEQ ID NOs: 50 and 36 (C-terminal lysine optional), respectively, is administered with a molecule comprising the amino acid sequence of SEQ ID NO: 58, 59, 60 or an amidated analog there. In another embodiment, a GDF15 molecule and corresponding Fc molecule comprising the amino acid sequences of SEQ ID NOs: 50 and 36 (C-terminal lysine optional), respectively, is administered with dulaglutide, such as a molecule comprising the amino acid sequence of SEQ ID NO: 61.

In another embodiment, a GDF15 molecule and corresponding Fc molecule comprising the amino acid sequences of SEQ ID NOs: 57 and 37 (C-terminal lysine optional), respectively, is administered with a molecule comprising the amino acid sequence of SEQ ID NO: 58, 59, 60 or an amidated analog there. In another embodiment, a GDF15 molecule and corresponding Fc molecule comprising the amino acid sequences of SEQ ID NOs: 57 and 37 (C-terminal lysine optional), respectively, is administered with dulaglutide, such as a molecule comprising the amino acid sequence of SEQ ID NO: 61.

In some embodiments, a GDF15 molecule disclosed herein is administered with an antagonist to GIPR, such as an antigen binding protein that specifically binds to a human GIPR. In one embodiment, the antigen binding protein specifically binds to human GIPR comprising or consisting of the amino acid sequence of:

MTTSPILQLLLRLSLCGLLLQRAETGSKGQTAGELYQRWERYRRECQETLAAAEPPS
GLACNGSFDMYVCWDYAAPNATARASCPWYLPWHHHVAAGFVLRQCGSDGQWG
LWRDHTQCENPEKNEAFLDQRLILERLQVMYTVGYSLSLATLLLALLILSLFRRLHCT
RNYIHINLFTSFMLRAAAILSRDRLLPRPGPYLGDQALALWNQALAACRTAQIVTQY
CVGANYTWLLVEGVYLHSLLVLVGGSEEGHFRYYLLLGWGAPALFVIPWVIVRYLY
ENTQCWERNEVKAIWWIIRTPILMTILINFLIFIRILGILLSKLRTRQMRCRDYRLRLAR
STLTLVPLLGVHEVVFAPVTEEQARGALRFAKLGFEIFLSSFQGFLVSVLYCFINKEVQ
SEIRRGWHHCRLRRSLGEEQRQLPERAFRALPSGSGPGEVPTSRGLSSGTLPGPGNEA
SRELESYC (SEQ ID NO: 62);
MTTSPILQLLLRLSLCGLLLQRAETGSKGQTAGELYQRWERYRRECQETLAAAEPPS
VAAGFVLRQCGSDGQWGLWRDHTQCENPEKNEAFLDQRLILERLQVMYTVGYSLS
LATLLLALLILSLFRRLHCTRNYIHINLFTSFMLRAAAILSRDRLLPRPGPYLGDQALA
LWNQALAACRTAQIVTQYCVGANYTWLLVEGVYLHSLLVLVGGSEEGHFRYYLLL
GWGAPALFVIPWVIVRYLYENTQCWERNEVKAIWWIIRTPILMTILINFLIFIRILGILLS
KLRTRQMRCRDYRLRLARSTLTLVPLLGVHEVVFAPVTEEQARGALRFAKLGFEIFL
SSFQGFLVSVLYCFINKEVQSEIRRGWHHCRLRRSLGEEQRQLPERAFRALPSGSGPG
EVPTSRGLSSGTLPGPGNEASRELESYC (SEQ ID NO: 63); or
MTTSPILQLLLRLSLCGLLLQRAETGSKGQTAGELYQRWERYRRECQETLAAAEPPS
GLACNGSFDMYVCWDYAAPNATARASCPWYLPWHHHVAAGFVLRQCGSDGQWG
LWRDHTQCENPEKNEAFLDQRLILERLQVMYTVGYSLSLATLLLALLILSLFRRLHCT
RNYIHINLFTSFMLRAAAILSRDRLLPRPGPYLGDQALALWNQALAACRTAQIVTQY
CVGANYTWLLVEGVYLHSLLVLVGGSEEGHFRYYLLLGWGAPALFVIPWVIVRYLY

-continued

ENTQCWERNEVKAIWWIIRTPILMTILINFLIFIRILGILLSKLRTRQMRCRDYRLRLAR
STLTLVPLLGVHEVVFAPVTEEQARGALRFAKLGFEIFLSSFQGFLVSVLYCFINKEVG
RDPAAAPALWRRRGTAPPLSAIVSQVQSEIRRGWHHCRLRRSLGEEQRQLPERAFRA
LPSGSGPGEVPTSRGLSSGTLPGPGNEASRELESYC (SEQ ID NO: 64).

The antigen binding protein that specifically binds to a human GIPR polypeptide can inhibit activation of GIPR by GIP ligand and/or inhibit GIP ligand binding to GIPR. The antigen binding protein may have the ability to prevent or reduce binding of GIP to GIPR, where the levels can be measured, for example, by the methods such as radioactive- or fluorescence-labeled ligand binding study, or by the methods described herein (e.g. cAMP assay or other functional assays). The decrease can be at least 10, 25, 50, 100% or more relative to the pre-treatment levels of SEQ ID NO: 62, 63, or 64 under comparable conditions. In certain embodiments, the antigen binding protein has a KD (equilibrium binding affinity) of less than 25 pM, 50 pM, 100 pM, 500 pM, 1 nM, 5 nM, 10 nM, 25 nM or 50 nM.

The antigen binding protein can be a human antigen binding protein, such as a human antibody. In another embodiment, the antigen binding protein is an antibody, such as a monoclonal antibody. In some embodiments, the antigen binding protein is a GIPR antibody disclosed in US Publication No. 2017/0275370 or 2018/0311372, each of which is incorporated by reference herein in its entirety.

In one embodiment, the GIPR antigen binding protein, such as an antibody, comprises a CDRL1, CDRL2 and CDRL3 comprising the amino acid sequence of: RASQSVSSNLA (SEQ ID NO: 65), GAATRAT (SEQ ID NO: 66) and QQYNNWPLT (SEQ ID NO: 67), respectively; SGSSSNIGSQTVN (SEQ ID NO: 68), TNNQRPS (SEQ ID NO: 69) and ATFDESLSGPV (SEQ ID NO: 70), respectively; RASQDIRDYLG (SEQ ID NO: 71), GASSLQS (SEQ ID NO: 72) and LQHNNYPFT (SEQ ID NO: 73), respectively; or RASQGLIIWL (SEQ ID NO: 74), AASSLQS (SEQ ID NO: 75) and QQTNSFPPT (SEQ ID NO: 76), respectively. In one embodiment, the GIPR antigen binding protein comprises a CDRH1, CDRH2 and CDRH3 comprising the amino acid sequence of: NYGMH (SEQ ID NO: 77), AIWFDASDKYYADAVKG (SEQ ID NO: 78) and DQAIFGVVPDY (SEQ ID NO: 79), respectively; GYYMH (SEQ ID NO: 80), WINPNSGGTNYAQKFQG (SEQ ID NO: 81) and GGDYVFGTYRPHYYYGMDV (SEQ ID NO: 82), respectively; YFGMH (SEQ ID NO: 83), VIWYDASNKYYADAVKG (SEQ ID NO: 84) and DGTIFGVLLGDY (SEQ ID NO: 85), respectively; or SYYWS (SEQ ID NO: 86), RIYTSGSTNYNPSLKS (SEQ ID NO: 87) and DVAVAGFDY (SEQ ID NO: 88), respectively.

In one embodiment, the GIPR antigen binding protein, such as an antibody, comprises a CDRL1, CDRL2, CDRL3, CDRH1, CDRH2, and CDRH3 comprising the amino acid sequences of: SEQ ID NOs: 65-67 and 77-79; SEQ ID NOs: 68-70 and 80-82; SEQ ID NOs: 71-73 and 83-85; or SEQ ID NOs: 74-76 and 86-88; respectively.

In one embodiment, the GIPR antigen binding protein, such as an antibody, comprises a light chain variable region and heavy chain variable region comprising the amino acid sequences of (SEQ ID NO: 89)
EIVMTQSPATLSVSPGERATLSCRASQSVSSNLAWYQQKPGQAPRLLIY
GAATRATGIPARVSGSGSGTEFTLTISSLQSEDFAVYYCQQYNNWPLTF
GGGTKVEIKR and (SEQ ID NO: 90)
QVQLVESGGGVVQPGRSLRLSCAASGFTFSNYGMHWVRQAPGEGLEWVA
AIWFDASDKYYADAVKGRFTISRDNSKNTLYLQMNSLRAEDTAVYYCAR
DQAIFGVVPDYWGQGTLVTVSS, respectively;

(SEQ ID NO: 91)
QSVLTOPPSASGTPGQRVTISCSGSSSNIGSQTVNWYQHLPGTAPKLLI
YTNNORPSGVPDRFSGSKSGTSASLAISGLOSEDEADYFCATFDESLSG
PVFGGGTKLTVLG and (SEQ ID NO: 92)
QMQVVQSGAEVKKPGASVKVSCKASGYTFTGYYMHWVRQAPGQGLEWMG
WINPNSGGTNYAQKFOGRVTMTRDTSISTAYMELSRLRSDDTAVYYCAR
GGDYVFGTYRPHYYYGMDVWGQGTTVTVSS, respectively;

(SEQ ID NO: 93)
DIQMTQSPSSLSASIGDRVTITCRASQDIRDYLGWYQQKPGKAPKLLIY
GASSLQSGVPSRFSGSGSGTEFTLTISSLQPEDFATYYCLQHNNYPFTF
GQGTKVDIKR and (SEQ ID NO: 94)
QVQLVESGGGVVQPGRSLRLSCAASGFTFSYFGMHWVRQAPGKGLEWVA
VIWYDASNKYYADAVKGRFTISRDNSKNTLYLQMNSLRAEDTAVYYCAR
DGTIFGVLLGDYWGQGTLVTVSS, respectively; or (SEQ ID NO: 95)
DIQMTQSPSSVSASVGDRVTITCRASQGLIIWLAWYQQKPGKAPKLLIY
AASSLQSGVPSRFSGSGSGTDFTLTISSLQPEDFATYYCQQTNSFPPTF
GQGTKVEIKR and (SEQ ID NO: 96)
QVQLQESGPGLVKPSETLSLTCTVSGGSISSYYWSWIRQPAGKGLEWIG
RIYTSGSTNYNPSLKSRVTMSIDTSKNQFSLKLNSVTAADTAVYYCARD
VAVAGFDYWGQGTLVTVSS, respectively.

In one embodiment, the GIPR antigen protein, such as an antibody, comprises a light chain and heavy chain comprising the amino acid sequences of (SEQ ID NO: 97)
EIVMTQSPATLSVSPGERATLSCRASQSVSSNLAWYQQKPGQAPRLLIYGAATRATGI

PARVSGSGSGTEFTLTISSLQSEDFAVYYCQQYNNWPLTFGGGTKVEIKRTVAAPSVF

IFPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC and (SEQ ID NO: 98)
QVQLVESGGGVVQPGRSLRLSCAASGFTFSNYGMHWVRQAPGEGLEWVAAIWFDA

SDKYYADAVKGRFTISRDNSKNTLYLQMNSLRAEDTAVYYCARDQAIFGVVPDYW

GQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDG

VEVHNAKTKPCEEQYGSTYRCVSVLTVLHQDWLNGKEYKCKVSNKALPAPIEKTIS

KAKGQPREPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLSPGK, respectively;

(SEQ ID NO: 99)
QSVLTQPPSASGTPGQRVTISCSGSSSNIGSQTVNWYQHLPGTAPKLLIYTNNQRPSGV

PDRFSGSKSGTSASLAISGLQSEDEADYFCATFDESLSGPVFGGGTKLTVLGQPKAAP

SVTLFPPSSEELQANKATLVCLISDFYPGAVTVAWKADSSPVKAGVETTTPSKQSNNK

YAASSYLSLTPEQWKSHRSYSCQVTHEGSTVEKTVAPTECS and (SEQ ID NO: 100)
QMQVVQSGAEVKKPGASVKVSCKASGYTFTGYYMHWVRQAPGQGLEWMGWINP

NSGGTNYAQKFQGRVTMTRDTSISTAYMELSRLRSDDTAVYYCARGGDYVFGTYRP

HYYYGMDVWGQGTTVTVSSASTKGPSVFPLAPSSKSTSGGTAALGCLVKDYFPEPV

TVSWNSGALTSGVHTFPAVLQSSGLYSLSSVVTVPSSSLGTQTYICNVNHKPSNTKVD

KKVEPKSCDKTHTCPPCPAPELLGGPSVFLFPPKPKDTLMISRTPEVTCVVVDVSHED

PEVKFNWYVDGVEVHNAKTKPCEEQYGSTYRCVSVLTVLHQDWLNGKEYKCKVSN

KALPAPIEKTISKAKGQPREPQVYTLPPSREEMTKNQVSLTCLVKGFYPSDIAVEWES

NGQPENNYKTTPPVLDSDGSFFLYSKLTVDKSRWQQGNVFSCSVMHEALHNHYTQK

SLSLSPGK, respectively;

(SEQ ID NO: 101)
DIQMTQSPSSLSASIGDRVTITCRASQDIRDYLGWYQQKPGKAPKLLIYGASSLQSGV

PSRFSGSGSGTEFTLTISSLQPEDFATYYCLQHNNYPFTFGQGTKVDIKRTVAAPSVFIF

PPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC and (SEQ ID NO: 102)
QVQLVESGGGVVQPGRSLRLSCAASGFTFSYFGMHWVRQAPGKGLEWVAVIWYDA

SNKYYADAVKGRFTISRDNSKNTLYLQMNSLRAEDTAVYYCARDGTIFGVLLGDYW

GQGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVDG

-continued

VEVHNAKTKPCEEQYGSTYRCVSVLTVLHQDWLNGKEYKCKVSNKALPAPIEKTIS

KAKGQPREPQVYTLPPSREEMTKNQVSLTCLVKGFYPSDIAVEWESNGQPENNYKTT

PPVLDSDGSFFLYSKLTVDKSRWQQGNVFSCSVMHEALHNHYTQKSLSLSPGK, respectively;

(SEQ ID NO: 103)
DIQMTQSPSSVSASVGDRVTITCRASQGLIIWLAWYQQKPGKAPKLLIYAASSLQSGV

PSRFSGSGSGTDFTLTISSLQPEDFATYYCQQTNSFPPTFGQGTKVEIKRTVAAPSVFIF

PPSDEQLKSGTASVVCLLNNFYPREAKVQWKVDNALQSGNSQESVTEQDSKDSTYS

LSSTLTLSKADYEKHKVYACEVTHQGLSSPVTKSFNRGEC and (SEQ ID NO: 104)
QVQLQESGPGLVKPSETLSLTCTVSGGSISSYYWSWIRQPAGKGLEWIGRIYTSGSTN

YNPSLKSRVTMSIDTSKNQFSLKLNSVTAADTAVYYCARDVAVAGFDYWGQGTLVT

VSSASTKGPSVFPLAPSSKSTSGGTAALGCLVKDYFPEPVTVSWNSGALTSGVHTFPA

VLQSSGLYSLSSVVTVPSSSLGTQTYICNVNHKPSNTKVDKKVEPKSCDKTHTCPPCP

APELLGGPSVFLFPPKPKDTLMISRTPEVTCVVVDVSHEDPEVKFNWYVDGVEVHNA

KTKPCEEQYGSTYRCVSVLTVLHQDWLNGKEYKCKVSNKALPAPIEKTISKAKGQPR

EPQVYTLPPSREEMTKNQVSLTCLVKGFYPSDIAVEWESNGQPENNYKTTPPVLDSD

GSFFLYSKLTVDKSRWQQGNVFSCSVMHEALHNHYTQKSLSLSPGK, respectively; or (SEQ ID NO: 105)
MKLPVRLLVLMFWIPASSSDVVMTQTPLSLPVSLGDQASISCRSSQSLVHSNGDTYLH

WYLQKPGQSPKLLIYKVSNRFSGVPDRFSGSGSGTDFTLKISRVEAADLGVYFCSQST

HVPPFTFGGGTKLEIKRADAAPTVSIFPPSSEQLTSGGASVVCFLNNFYPKDINVKWKI

DGSERQNGVLNSWTDQDSKDSTYSMSSTLTLTKDEYERHNSYTCEATHKTSTSPIVK

SFNRNEC and (SEQ ID NO: 106)
MGWSYIILFLVATATDVHSQVQLQQPGAELVKPGASVKLSCRASGYTFTSNWMHW

VKQRPRQGLEWIGEINPSNGRSNYNEKFKTKATLTVDKSSSTAYMQLSSLTSEDSAV

YYCARFYYGTSWFAYWGQGTLVAVSAAKTTPPSVYPLAPGSAAQTNSMVTLGCLV

KGYFPEPVTVTWNSGSLSSGVHTFPAVLQSDLYTLSSSVTVPSSTWPSETVTCNVAHP

ASSTKVDKKIVPRDCGCKPCICTVPEVSSVFIFPPKPKDVLTITLTPKVTCVVVDISKDD

PEVQFSWFVDDVEVHTAQTQPREEQFASTFRSVSELPIMHQDWLNGKEFKCRVNSA

AFPAPIEKTISKTKGRPKAPQVYTIPPPKEQMAKDKVSLTCMITDFFPEDITVEWQWN

GQPAENYKNTQPIMDTDGSYFVYSKLNVQKSNWEAGNTFTCSVLHEGLHNHHTEKS

LSHSPGK, respectively.

In one embodiment, a GDF15 molecule comprising the amino acid sequence of SEQ ID NO: 39, 40, 41, 42, 43, 44, 45, 46, 47, 48, 49, 50, 51, 52, 53, 54, 55, 56 or 57 is administered with a GIPR antigen binding protein, such as an antibody, that comprises a CDRL1, CDRL2, CDRL3, CDRH1, CDRH2, and CDRH3 comprising the amino acid sequences of: SEQ ID NOs: 65-67 and 77-79; SEQ ID NOs: 68-70 and 80-82; SEQ ID NOs: 71-73 and 83-85; or SEQ ID NOs: 74-76 and 86-88; respectively.

In another embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; is administered with a GIPR antigen binding protein, such as an antibody, that comprises a CDRL1, CDRL2, CDRL3, CDRH1, CDRH2, and CDRH3 comprising the amino acid sequences of: SEQ ID NOs: 65-67 and 77-79; SEQ ID NOs: 68-70 and 80-82; SEQ ID NOs: 71-73 and 83-85; or SEQ ID NOs: 74-76 and 86-88; respectively.

In another embodiment, a GDF15 molecule and corresponding Fc molecule comprising the amino acid sequences of SEQ ID NOs: 50 and 36 (C-terminal lysine optional), respectively, is administered with a GIPR antigen binding protein, such as an antibody, that comprises a CDRL1, CDRL2, CDRL3, CDRH1, CDRH2, and CDRH3 comprising the amino acid sequences of: SEQ ID NOs: 65-67 and 77-79; SEQ ID NOs: 68-70 and 80-82; SEQ ID NOs: 71-73 and 83-85; or SEQ ID NOs: 74-76 and 86-88; respectively. In one embodiment, a GDF15 molecule and corresponding Fc molecule comprising the amino acid sequences of SEQ ID NOs: 50 and 36 (C-terminal lysine optional), respectively, is administered with an antibody that comprises a CDRL1, CDRL2, CDRL3, CDRH1, CDRH2, and CDRH3 comprising the amino acid sequences of: SEQ ID NOs: 65-67 and 77-79.

In another embodiment, a GDF15 molecule and corresponding Fc molecule comprising the amino acid sequences of SEQ ID NOs: 57 and 37 (C-terminal lysine optional), respectively, is administered with a GIPR antigen binding protein, such as an antibody, that comprises a CDRL1, CDRL2, CDRL3, CDRH1, CDRH2, and CDRH3 comprising the amino acid sequences of: SEQ ID NOs: 65-67 and 77-79; SEQ ID NOs: 68-70 and 80-82; SEQ ID NOs: 71-73 and 83-85; or SEQ ID NOs: 74-76 and 86-88; respectively. In another embodiment, a GDF15 molecule and corresponding Fc molecule comprising the amino acid sequences of SEQ ID NOs: 57 and 37 (C-terminal lysine optional), respectively, is administered with an antibody that comprises a CDRL1, CDRL2, CDRL3, CDRH1, CDRH2, and CDRH3 comprising the amino acid sequences of: SEQ ID NOs: 65-67 and 77-79.

In one embodiment, a GDF15 molecule comprising the amino acid sequence of SEQ ID NO: 39, 40, 41, 42, 43, 44, 45, 46, 47, 48, 49, 50, 51, 52, 53, 54, 55, 56 or 57 is administered with a GIPR antigen binding protein, such as an antibody, that comprises a light chain variable region and heavy chain variable region comprising the amino acid sequences of SEQ ID NOs: 89 and 90, SEQ ID NOs: 91 and 92, SEQ ID NOs: 93 and 94, or SEQ ID NOs: 95 and 96, respectively.

In another embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; is administered with a GIPR antigen binding protein, such as an antibody, that comprises a light chain variable region and heavy chain variable region comprising the amino acid sequences of SEQ ID NOs: 89 and 90, SEQ ID NOs: 91 and 92, SEQ ID NOs: 93 and 94, or SEQ ID NOs: 95 and 96, respectively.

In another embodiment, a GDF15 molecule and corresponding Fc molecule comprising the amino acid sequences of SEQ ID NOs: 50 and 36 (C-terminal lysine optional), respectively, is administered with a GIPR antigen binding protein, such as an antibody, that comprises a light chain variable region and heavy chain variable region comprising the amino acid sequences of SEQ ID NOs: 89 and 90, SEQ ID NOs: 91 and 92, SEQ ID NOs: 93 and 94, or SEQ ID NOs: 95 and 96, respectively. In one embodiment, a GDF15 molecule and corresponding Fc molecule comprising the amino acid sequences of SEQ ID NOs: 50 and 36 (C-terminal lysine optional), respectively, is administered with an antibody that comprises a light chain variable region and heavy chain variable region comprising the amino acid sequences of SEQ ID NOs: 89 and 90.

In another embodiment, a GDF15 molecule and corresponding Fc molecule comprising the amino acid sequences of SEQ ID NOs: 57 and 37 (C-terminal lysine optional), respectively, is administered with a GIPR antigen binding protein, such as an antibody, that comprises a light chain variable region and heavy chain variable region comprising the amino acid sequences of SEQ ID NOs: 89 and 90, SEQ ID NOs: 91 and 92, SEQ ID NOs: 93 and 94, or SEQ ID NOs: 95 and 96, respectively. In one embodiment, a GDF15 molecule and corresponding Fc molecule comprising the amino acid sequences of SEQ ID NOs: 57 and 37 (C-terminal lysine optional), respectively, is administered with an antibody that comprises a light chain variable region and heavy chain variable region comprising the amino acid sequences of SEQ ID NOs: 89 and 90.

In one embodiment, a GDF15 molecule comprising the amino acid sequence of SEQ ID NO: 39, 40, 41, 42, 43, 44, 45, 46, 47, 48, 49, 50, 51, 52, 53, 54, 55, 56 or 57 is administered with a GIPR antigen binding protein, such as an antibody, that comprises a light chain and heavy chain comprising the amino acid sequences of SEQ ID NOs: 97 and 98, SEQ ID NOs: 99 and 100, SEQ ID NOs: 101 and 102, SEQ ID NOs: 103 and 104, or SEQ ID NOs: 105 and 106, respectively.

In another embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; is administered with a GIPR antigen binding protein, such as an antibody, that comprises a light chain and heavy chain comprising the amino acid sequences of SEQ ID NOs: 97 and 98, SEQ ID NOs: 99 and 100, SEQ ID NOs: 101 and 102, SEQ ID NOs: 103 and 104, or SEQ ID NOs: 105 and 106, respectively.

In another embodiment, a GDF15 molecule and corresponding Fc molecule comprising the amino acid sequences of SEQ ID NOs: 50 and 36 (C-terminal lysine optional), respectively, is administered with a GIPR antigen binding protein, such as an antibody, that comprises a light chain and heavy chain comprising the amino acid sequences of SEQ ID NOs: 97 and 98, SEQ ID NOs: 99 and 100, SEQ ID NOs: 101 and 102, SEQ ID NOs: 103 and 104, or SEQ ID NOs: 105 and 106, respectively. In one embodiment, a GDF15 molecule and corresponding Fc molecule comprising the amino acid sequences of SEQ ID NOs: 50 and 36 (C-terminal lysine optional), respectively, is administered with an antibody that comprises a light chain and heavy chain comprising the amino acid sequences of SEQ ID NOs: 97 and 98.

In another embodiment, a GDF15 molecule and corresponding Fc molecule comprising the amino acid sequences of SEQ ID NOs: 57 and 37 (C-terminal lysine optional), respectively, is administered with a GIPR antigen binding protein, such as an antibody, that comprises a light chain and heavy chain comprising the amino acid sequences of SEQ ID NOs: 97 and 98, SEQ ID NOs: 99 and 100, SEQ ID NOs: 101 and 102, SEQ ID NOs: 103 and 104, or SEQ ID NOs: 105 and 106, respectively. In one embodiment, a GDF15 molecule and corresponding Fc molecule comprising the amino acid sequences of SEQ ID NOs: 57 and 37 (C-terminal lysine optional), respectively, is administered with an antibody that comprises a light chain and heavy chain comprising the amino acid sequences of SEQ ID NOs: 97 and 98.

In some embodiments, a GDF15 molecule disclosed herein is administered with a GIPR antibody conjugated to a GLP-1R agonist, such as disclosed in US Publication No. 2018/0311372, which is incorporated by reference herein in its entirety.

Other examples of agents that can be used in combination with a GDF15 molecule disclosed herein include rosiglitizone, pioglitizone, repaglinide, nateglitinide, metformin, exenatide, stiagliptin, pramlintide, glipizide, glimeprirideacarbose, orlistat, lorcaserin, phenterminetopiramate, naltrexonebupropion, setmelanotide, semaglutide, efpeglenatide, lixisenatide, canagliflozin, LIK-066, SAR-425899, Tt-401, FGFR4Rx, HDV-biotin and miglitol.

A GDF15 molecule administered with another therapeutic agent can include concurrent administration of a therapeutically effective amount of the GDF15 molecule (and optionally, its corresponding Fc molecule) and a therapeutically effective amount of the other therapeutic agent. A GDF15 molecule administered with another therapeutic agent can include subsequent administration of a therapeutically effective amount of the GDF15 molecule (and optionally, its corresponding Fc molecule) and a therapeutically effective amount of the other therapeutic agent, e.g., administration of a therapeutically effective amount of the GDF15 molecule (and optionally, its corresponding Fc molecule) followed by a therapeutically effective amount of the other therapeutic agent or administration of a therapeutically effective amount of the other therapeutic agent followed by administration of a therapeutically effective amount of the GDF15 molecule (and optionally, its corresponding Fc molecule). Administration of a therapeutically effective amount of the GDF15 molecule (and optionally, its corresponding Fc molecule) can be at least 1, 2, 3, 4, 5, 6, or 7 days after administration of a therapeutically effective amount of the other therapeutic agent. In another embodiment, administration of a therapeutically effective amount of a therapeutically effective amount of the other therapeutic agent can be at least 1, 2, 3, 4, 5, 6, or 7 days after at least 1, 2, 3, 4, 5, 6, or 7 days after administration of a therapeutically effective amount of the GDF15 molecule (and optionally, its corresponding Fc molecule).

A GDF15 molecule administered concurrently with another therapeutic agent can comprise administration of a composition comprising both the GDF15 molecule (and optionally its corresponding Fc molecule) and the other therapeutic agent, e.g., a therapeutically effective amount of the GDF15 molecule (and optionally its corresponding Fc molecule) is combined with a therapeutically effective amount of the other agent prior to administration. In another embodiment, concurrent administration of GDF15 molecule (and optionally its corresponding Fc molecule) and another therapeutic agent can comprise concurrent administration of a first composition comprising the GDF15 molecule and a second composition comprising the other therapeutic agent.

In some embodiments, administration of a GDF15 molecule with another therapeutic agent has a synergistic effect. In one embodiment, the effect is greater than the GDF15 molecule (and optionally its corresponding Fc molecule) alone or the other agent. In another embodiment, the effect is greater than an additive effect of both agents (the GDF15 molecule, and optionally its corresponding Fc molecule, plus the other agent). In one embodiment, combination therapy (i.e., administration of a GDF15 molecule, optionally with its corresponding Fc molecule, with another therapeutic agent) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy (administration of the GDF15 molecule, and optionally its corresponding Fc molecule). In another embodiment, combination therapy (i.e., administration of a GDF15 molecule, optionally with its corresponding Fc molecule, with another therapeutic agent) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than monotherapy with the other agent. The effect can be the amount of body weight lost (e.g., the decrease in total mass or percent body change); the decrease in blood glucose, insulin, triglyceride, or cholesterol levels; the improvement in glucose tolerance, energy expenditure, or insulin sensitivity; or the reduction food intake. The synergistic effect can be about 1, 2, 3, 4, 5, 6, 7, 8, 9, 10, 11, 12, 13, 14, 21, 28, 35, 42, 49, 56, 63, or 70 days after administration.

In one embodiment, a GDF15 molecule and corresponding Fc molecule comprising the amino acid sequences of SEQ ID NOs: 39 and 32 (C-terminal lysine optional), respectively; SEQ ID NOs: 40 and 33 (C-terminal lysine optional), SEQ ID NOs: 41 and 32 (C-terminal lysine optional), respectively; SEQ ID NOs: 42 and 32 (C-terminal lysine optional), respectively; SEQ ID NOs: 43 and 34 (C-terminal lysine optional), respectively; SEQ ID NOs: 44 and 34 (C-terminal lysine optional), respectively; SEQ ID NOs: 45 and 35 (C-terminal lysine optional), respectively; SEQ ID NOs: 46 and 35 (C-terminal lysine optional), respectively; SEQ ID NOs: 47 and 36 (C-terminal lysine optional) respectively; SEQ ID NOs: 48 and 36 (C-terminal lysine optional), respectively; SEQ ID NOs: 49 and 36 (C-terminal lysine optional) respectively; SEQ ID NOs: 50 and 36 (C-terminal lysine optional), respectively; SEQ ID NOs: 51 and 36 (C-terminal lysine optional), respectively; SEQ ID NOs: 52 and 36 (C-terminal lysine optional), respectively; SEQ ID NOs: 53 and 36 (C-terminal lysine optional), respectively; SEQ ID NOs: 54 and 36 (C-terminal lysine optional), respectively; SEQ ID NOs: 55 and 36 (C-terminal lysine optional), respectively; SEQ ID NOs: 56 and 37 (C-terminal lysine optional), respectively; or SEQ ID NOs: 57 and 37 (C-terminal lysine optional), respectively; administered with a GLP-1R agonist or a GIPR antagonist has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy; a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GLP-1R agonist or GIPR antagonist monotherapy (i.e., administration of GLP-1R agonist alone or GIPR antagonist alone); or both, about 1, 2, 3, 4, 5, 6, 7, 8, 9, 10, 11, 12, 13, 14, 21, 28, 35, 42, 49, 56, 63, or 70 days after administration of the agent(s).

In another embodiment, a GDF15 molecule and corresponding Fc molecule comprising the amino acid sequences of SEQ ID NOs: 50 and 36 (C-terminal lysine optional), respectively, administered with a GLP-1R agonist (e.g., dulaglutide) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy; a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GLP-1R agonist (e.g., dulaglutide) monotherapy; or both, about 1, 2, 3, 4, 5, 6, 7, 8, 9, 10, 11, 12, 13, 14, 21, 28, 35, 42, 49, 56, 63, or 70 days after administration of the GDF15 molecule and corresponding Fc molecule and/or dulaglutide.

In another embodiment, a GDF15 molecule and corresponding Fc molecule comprising the amino acid sequences of SEQ ID NOs: 57 and 37 (C-terminal lysine optional), respectively, administered with a GLP-1R agonist (e.g., dulaglutide) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy; a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GLP-1R agonist (e.g., dulaglutide) monotherapy; or both, about 1, 2, 3, 4, 5, 6, 7, 8, 9, 10, 11, 12, 13, 14, 21, 28, 35, 42, 49, 56, 63, or 70 days after administration of the GDF15 molecule and corresponding Fc molecule and/or dulaglutide.

In another embodiment, a GDF15 molecule and corresponding Fc molecule comprising the amino acid sequences of SEQ ID NOs: 50 and 36 (C-terminal lysine optional), respectively, administered with a GIPR antigen binding protein (e.g., an antibody that comprises a CDRL1, CDRL2, CDRL3, CDRH1, CDRH2, and CDRH3 comprising the amino acid sequences of: SEQ ID NOs: 65-67 and 77-79; SEQ ID NOs: 68-70 and 80-82; SEQ ID NOs: 71-73 and 83-85; or SEQ ID NOs: 74-76 and 86-88; respectively; or an antibody, that comprises a light chain variable region and heavy chain variable region comprising the amino acid sequences of SEQ ID NOs: 89 and 90, SEQ ID NOs: 91 and 92, SEQ ID NOs: 93 and 94, or SEQ ID NOs: 95 and 96, respectively; or an antibody, that comprises a light chain and heavy chain comprising the amino acid sequences of SEQ ID NOs: 97 and 98, SEQ ID NOs: 99 and 100, SEQ ID NOs: 101 and 102, SEQ ID NOs: 103 and 104, or SEQ ID NOs: 105 and 106, respectively) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy; a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GIPR antigen binding protein monotherapy; or both, about 1, 2, 3, 4, 5, 6, 7, 8, 9, 10, 11, 12, 13, 14, 21, 28, 35, 42, 49, 56, 63, or 70 days after administration of the GDF15 molecule and corresponding Fc molecule and/or GIPR antigen binding protein.

In another embodiment, a GDF15 molecule and corresponding Fc molecule comprising the amino acid sequences of SEQ ID NOs: 57 and 37 (C-terminal lysine optional), respectively, administered with a GIPR antigen binding protein (e.g., an antibody that comprises a CDRL1, CDRL2, CDRL3, CDRH1, CDRH2, and CDRH3 comprising the amino acid sequences of: SEQ ID NOs: 65-67 and 77-79; SEQ ID NOs: 68-70 and 80-82; SEQ ID NOs: 71-73 and 83-85; or SEQ ID NOs: 74-76 and 86-88; respectively; or an antibody, that comprises a light chain variable region and heavy chain variable region comprising the amino acid sequences of SEQ ID NOs: 89 and 90, SEQ ID NOs: 91 and 92, SEQ ID NOs: 93 and 94, or SEQ ID NOs: 95 and 96, respectively; or an antibody, that comprises a light chain and heavy chain comprising the amino acid sequences of SEQ ID NOs: 97 and 98, SEQ ID NOs: 99 and 100, SEQ ID NOs: 101 and 102, SEQ ID NOs: 103 and 104, or SEQ ID NOs: 105 and 106, respectively) has a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GDF15 monotherapy; a greater than 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, 20, 21, 22, 23, 24, 25, 26, 27, 28, 29, or 30 fold effect than GIPR antigen binding protein monotherapy; or both, about 1, 2, 3, 4, 5, 6, 7, 8, 9, 10, 11, 12, 13, 14, 21, 28, 35, 42, 49, 56, 63, or 70 days after administration of the GDF15 molecule and corresponding Fc molecule and/or GIPR antigen binding protein.

In one embodiment, the molar ratio of the GDF15 molecule to the GLP-1R agonist or GIPR antagonist is from about 1:1 to 1:100, 1:1 to 1:75, 1:1 to 1:50, 1:1 to 1:25, 1:1 to 1:10, or 1:1 to 1:5. In one embodiment, the molar ratio of the GDF15 molecule to the GLP-1R agonist or GIPR antagonist is about 1:1, about 1:2, about 1:3, about 1:4, about 1:5, about 1:10, about 1:20, about 1:30, about 1:40, or about 1:50. In one embodiment, the molar ratio of the GDF15 molecule to the GLP-1R agonist (e.g., dulaglutide) is from about 1:1 to 1:100, 1:1 to 1:75, 1:1 to 1:50, 1:1 to 1:25, 1:1 to 1:10, or 1:1 to 1:5; or about 1:1, about 1:2, about 1:3, about 1:4, about 1:5, about 1:10, about 1:20, about 1:30, about 1:40, or about 1:50. In another embodiment, the molar ratio of the GDF15 molecule to the GIPR antagonist (e.g., GIPR antibody) is from about 1:1 to 1:100, 1:1 to 1:75, 1:1 to 1:50, 1:1 to 1:25, 1:1 to 1:10, or 1:1 to 1:5; or about 1:1 to 1:110, 1:1 to 1:100, 1:1 to 1:75, 1:1 to 1:50, 1:1 to 1:25, 1:1 to 1:10, or 1:1 to 1:5, or is about 1:1, about 1:2, about 1:3, about 1:4, about 1:5, about 1:10, about 1:20, about 1:30, about 1:33, about 1:40, or about 1:50.

In one embodiment, the GDF15 molecule and the GLP-1R agonist or GIPR antagonist are present in doses that are at least about 1.1 to 1.4, 1.5, 2, 3, 4, 5, 6, 7, 8, 9, or 10 fold lower than the doses of each compound alone required to have a therapeutic effect (e.g., treat a condition and/or disease; decrease body weight lost; decrease blood glucose, insulin, triglyceride, or cholesterol levels; improve glucose tolerance, energy expenditure, or insulin sensitivity; or reduce food intake).

The detailed description and following examples illustrate the present invention and are not to be construed as limiting the present invention thereto. Various changes and modifications can be made by those skilled in the art on the basis of the description of the invention, and such changes and modifications are also included in the present invention.

EXAMPLES

The following examples, including the experiments conducted and results achieved, are provided for illustrative purposes only and are not to be construed as limiting the present invention.

Example 1: GDF15 Molecule Production

FcΔ10(−)-(G4S)4-GDF15 (SEQ ID NO: 39) was stably expressed in a serum free, suspension adapted CHO-K1 cell line. It was cloned into a stable expression vector containing puromycin resistance while the Fc chain for forming a heterodimer with FcΔ10(−)-(G4S)4-GDF15, FcΔ10(+,K) (SEQ ID NO: 32), was cloned into a hygromycin containing expression vector (Selexis, Inc.). The plasmids were transfected at a 1:1 ratio using lipofectamine LTX and cells were selected 2 days post transfection in a proprietary growth media containing 10 ug/mL puromycin and 600 ug/mLhygromycin. Media was exchanged 2 times per week during selection. When cells reached about 90% viability, they were scaled up for a batch production run. Cells were seeded at $2\times10^6$/mL in production media. The conditioned medium (CM) produced by the cells was harvested on day 7 and clarified. Endpoint viabilities typically were above 90%.

FcΔ10(−)-(G4S)4-GDF15 (SEQ ID NO: 39) (and any paired Fc) were clarified. Conditioned media was purified using a two-step chromatography procedure. Approximately 5 L of the CM was applied directly to a GE MabSelect SuRe column that had previously been equilibrated with Dulbecco's Phosphate Buffered Saline (PBS). The bound protein underwent three wash steps: first, 3 column volumes (CV) of PBS; next, 1 CV of 20 mM Tris, 100 mM sodium chloride, pH 7.4; and finally, 3 CV of 500 mM L-arginine, pH 7.5. These wash steps remove unbound or lightly bound media components and host cell impurities. The column was then re-equilibrated with 5 CV of 20 mM Tris, 100 mM sodium chloride at pH 7.4 which brings the UV absorbance back to baseline. The desired protein was eluted with 100 mM acetic acid at pH 3.6 and collected in bulk. The protein pool was quickly titrated to within a pH range of 5.0 to 5.5 with 1 M Tris-HCl, pH 9.2. The pH adjusted protein pool was next loaded onto a GE SP Sepharose HP column that had been previously equilibrated with 20 mM MES at pH 6.0. The bound protein was then washed with 5 CV of equilibration buffer, and finally eluted over a 20 CV, 0 to 50% linear gradient from 0 to 400 mM sodium chloride in 20 mM MES at pH 6.0. Fractions were collected during the elution and analyzed by analytical size-exclusion chromatography (Superdex 200) to determine the appropriate fractions to pool for a homogeneous product. The SP HP chromatography removes product-related impurities such as free Fc, clipped species, and Fc-GDF15 multimers. The SP HP pool was then buffer exchanged into 10 mM sodium acetate, 5% proline, pH 5.2 by dialysis. It was concentrated to approximately 15 mg/ml using the Sartorius Vivaspin 20 Ten kilo-Dalton molecular weight cut-off centrifugal device. Finally, it was sterile filtered and the resulting solution containing the purified Fc-GDF15 molecules is stored at 5° C. Final products were assessed for identity and purity using mass spectral analysis, sodium dodecyl sulfate polyacrylamide electrophoresis and size exclusion high performance liquid chromatography.

Example 2: GDF15, Dulaglutide, and/or GIPR Antibody Administration

Male C57Bl/6 DIO mice, 19-20 weeks old (13-14 weeks on high fat diet) at beginning of dosing, were placed into the following treatment groups: Group A—Vehicle, in which the animals were administered vehicle weekly; Group B—Dulaglutide, in which the animals were administered 0.1 mg/kg (2 nmol/kg) of dulaglutide twice per week; Group C—GIPR Ab, in which the animals were administered 5 mg/kg (33 nmol/kg) of antibody 2.63.1 (having a light and heavy chain sequence of SEQ ID NOs: 105 and 106, respectively) weekly and vehicle weekly (the latter being on the alternate dulaglutide dosing day); Group D—GDF15, in which the animals were administered 0.125 mg/kg (1 nmol/kg) of FcΔ10(−)-(G4S)4-GDF15 (SEQ ID NO: 39) (along with its heterodimerization partner, FcΔ10(+,K) (SEQ ID NO: 32)) weekly and vehicle weekly (the latter on the alternate dulaglutide dosing day); Group E—GDF15+Dulaglutide, in which the animals were administered 0.125 mg/kg (1 nmol/kg) of FcΔ10(−)-(G4S)4-GDF15) (along with its heterodimerization partner, FcΔ10(+,K)) weekly and 0.1 mg/kg (2 nmol/kg) of dulaglutide twice per week; Group F—GDF15+GIPR Ab, in which the animals were administered 0.125 mg/kg (1 nmol/kg) of FcΔ10(−)-(G4S)4-GDF15 (along with its heterodimerization partner, FcΔ10(+,K)) weekly and 5 mg/kg (33 nmol/kg) of antibody 2.63.1 weekly. The animals were dosed for 5 weeks with through subcutaneous injection.

Figure 1B:
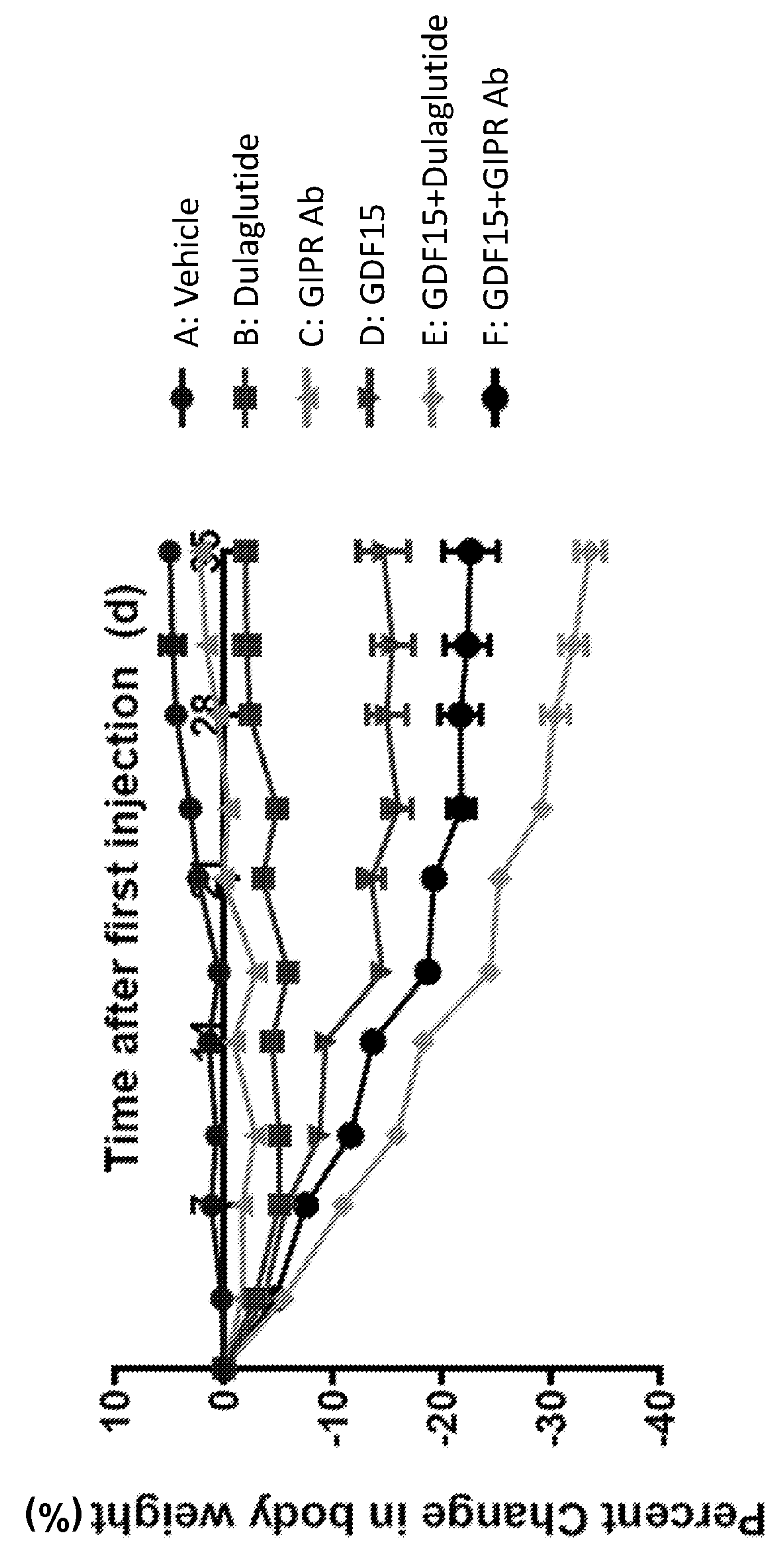
FIG. 1B shows the percent body weight change of the mice in Groups A-F.

Body weight was measured twice per week. FIG. 1 shows the body weight change (FIG. 1A in grams, FIG. 1B in percent body weight change). The significance of the body weight change is shown in Table 7.

TABLE 7

Significance of Body Weight Change

| Group | D-4 | D0 | D3 | D7 | D10 | D14 | D17 | D21 | D31 | D35 |
|---|---|---|---|---|---|---|---|---|---|---|
| A | — | — | — | — | — | — | — | — | — | — |
| B | ns | ns | ns | ns | ** | ** | **** | *** | *** | *** |
| C | ns | ns | ns | ns | ns | ns | ns | ns | ns | ns |
| D | ns | ns | ns | ** | **** | **** | **** | **** | *** | *** |
| E | ns | ns | ** | **** | **** | **** | **** | **** | **** | **** |
| F | ns | ns | ns | **** | **** | **** | **** | **** | **** | **** |

ns: not significant;
*p < 0.05, p < 0.005, *p < 0.001, ****p < 0.0001 by 2-way ANOVA with Dunnett's analysis in Graphpad prism.

Figure 2A:
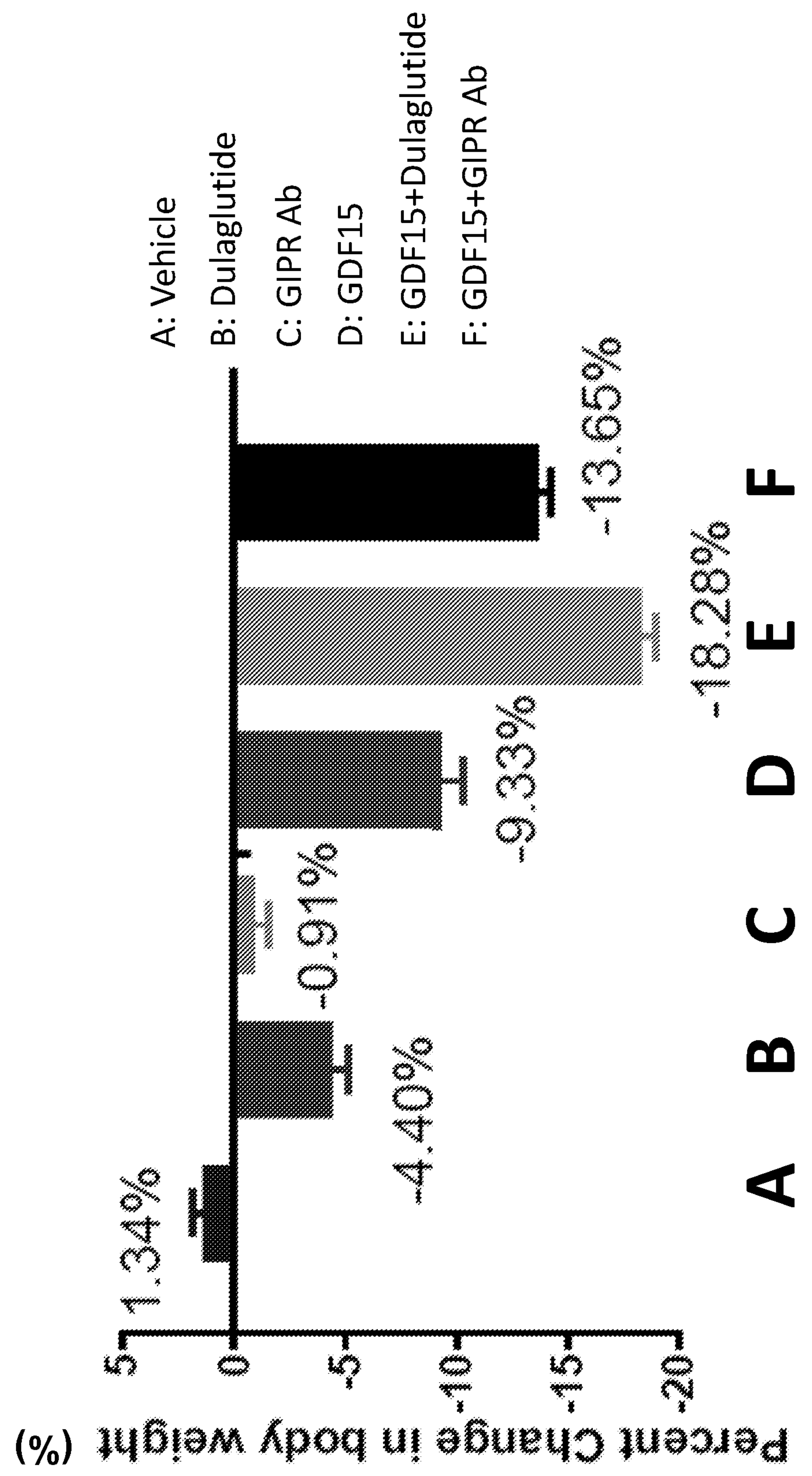
FIG. 2A shows the percent body weight change of the mice in Groups A-F 2 weeks after treatment started.
Figure 2B:
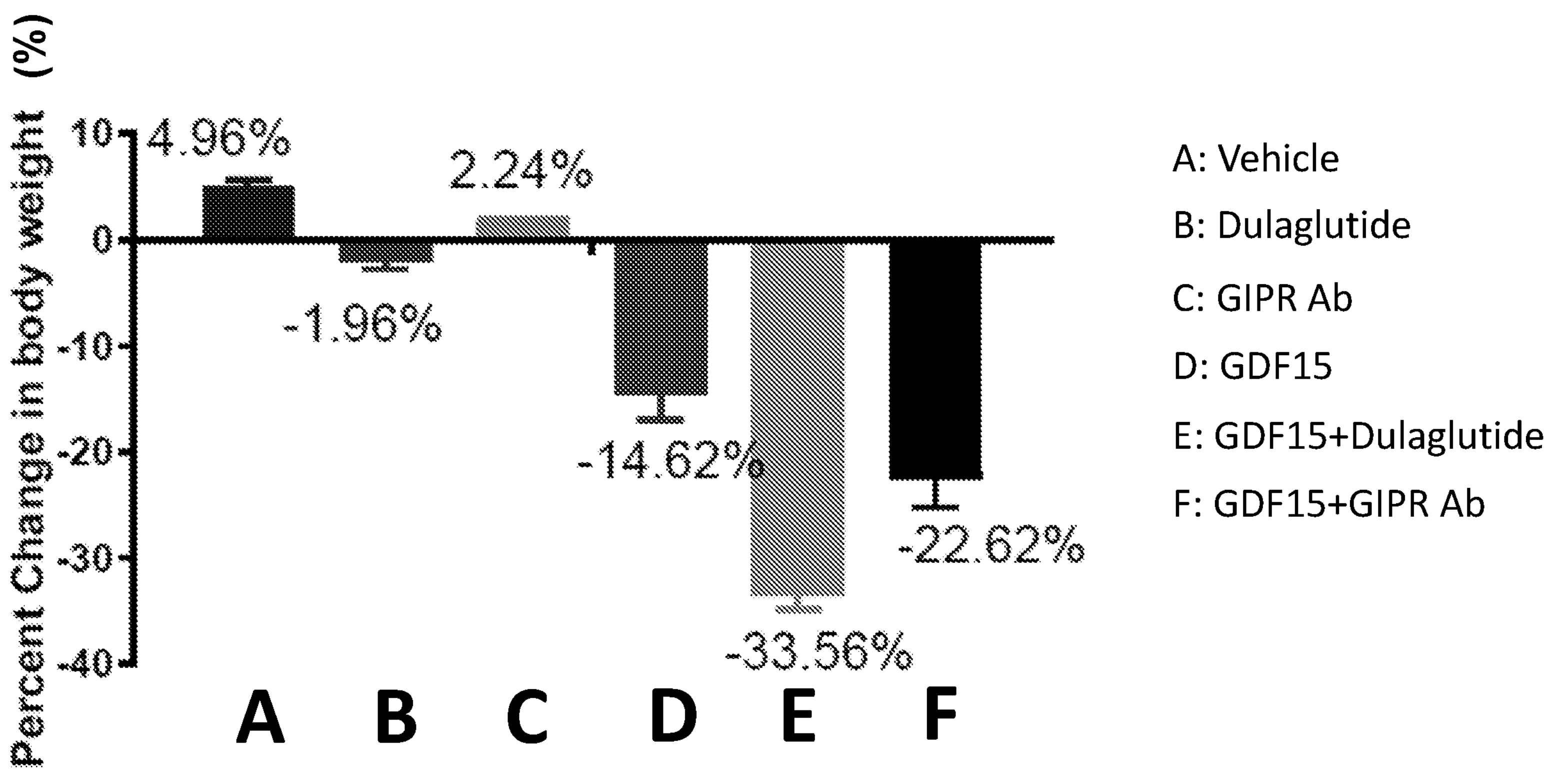
FIG. 2B shows the percent body weight change of the mice in Groups A-F 5 weeks after treatment started.

FIG. 2 shows the percent body weight change 2 weeks (FIG. 2A) and 5 weeks (FIG. 2B) after treatment started. The data shows that combination treatment of GDF15 with either Dulaglutide or GIPR Ab was synergistic. At two weeks after treatment, mice in Group D (GDF15) had −9.33% change in body weight, while mice in Group B (Dulaglutide) or Group C (GIPR Ab) had a 4.40% and −0.91% change in body weight, respectively. However, mice in Group E (GDF15+Dulaglutide) had a −18.28% change in body weight, greater than an additive effect of −13.73%. The decrease was more than three-fold as compared to Dulaglutide treatment alone and almost two-fold the decrease seen in GDF15 treatment alone. Mice in Group F (GDF15+GIPR Ab) had a −13.65% change in body weight, greater than an additive effect of −14.56%, The decrease was more than thirteen-fold as compared to GIPR Ab treatment alone and almost 1.5 fold the decrease seen m CDF15 treatment alone.

At five weeks after treatment, mice in Group D (GDF15) had −14.62% change in body weight, while mice in Group B (Dulaglutide) or Group C (GIPR Ab) had a −1.96% and 2.24% change in body weight, respectively. However, mice in Group E (GDF15+Dulaglutide) had a −33.56% change in body weight, greater than an additive effect of −15,58%. The decrease was more than fifteen-Told as compared to Dulaglutide treatment alone and more than two-fold the decrease seen in GDF15 treatment alone. Mice in Group F (GDF15+GIPR Ab) had a −22.62% change in body weight, greater than an additive effect of −12.38%. The decrease was more than twenty-fold as compared to GIPR Ab treatment alone and more than 1.5 fold the decrease seen m GDF15 treatment alone.

Figure 3A:
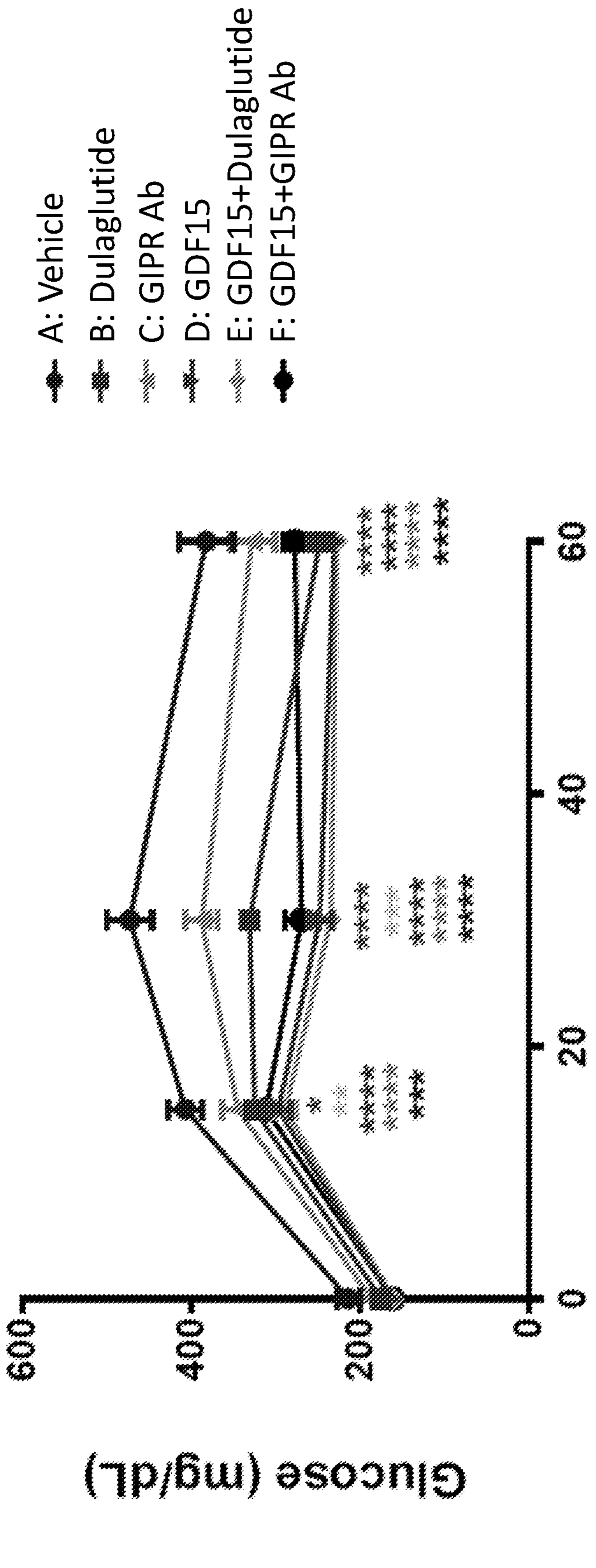
FIG. 3A shows the glucose levels from the oral glucose tolerance test (OGTT) of the mice in Groups A-F two weeks after treatment.
Figure 3B:
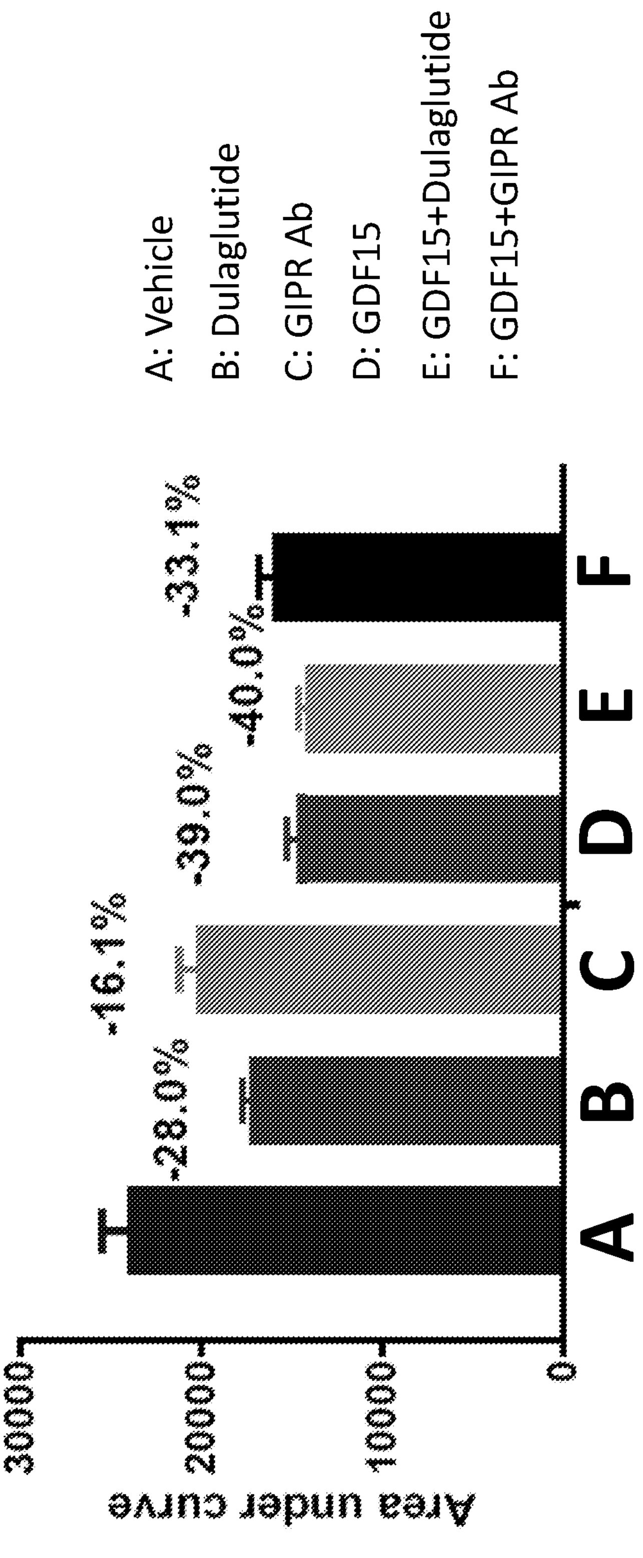
FIG. 3B shows the glucose AUC results from the OGTT of the mice in Groups A-F two weeks after treatment.

An oral glucose tolerance test (OGTT) was conducted 2 weeks after first treatment and FIG. 3 shows the glucose levels (FIG. 3A) and glucose AUC (FIG. 3B) during oral glucose tolerance test 2 weeks after treatment started, with the AUC differences between treatment groups and vehicle group labeled on top of each bar in FIG. 3B. Combination therapy did not have a greater effect than GDF15 monotherapy (Groups E and F having −40.0% AUC and −33.1% AUC, respectively, as compared to Group D having −39.0% AUC).

Figure 4A:
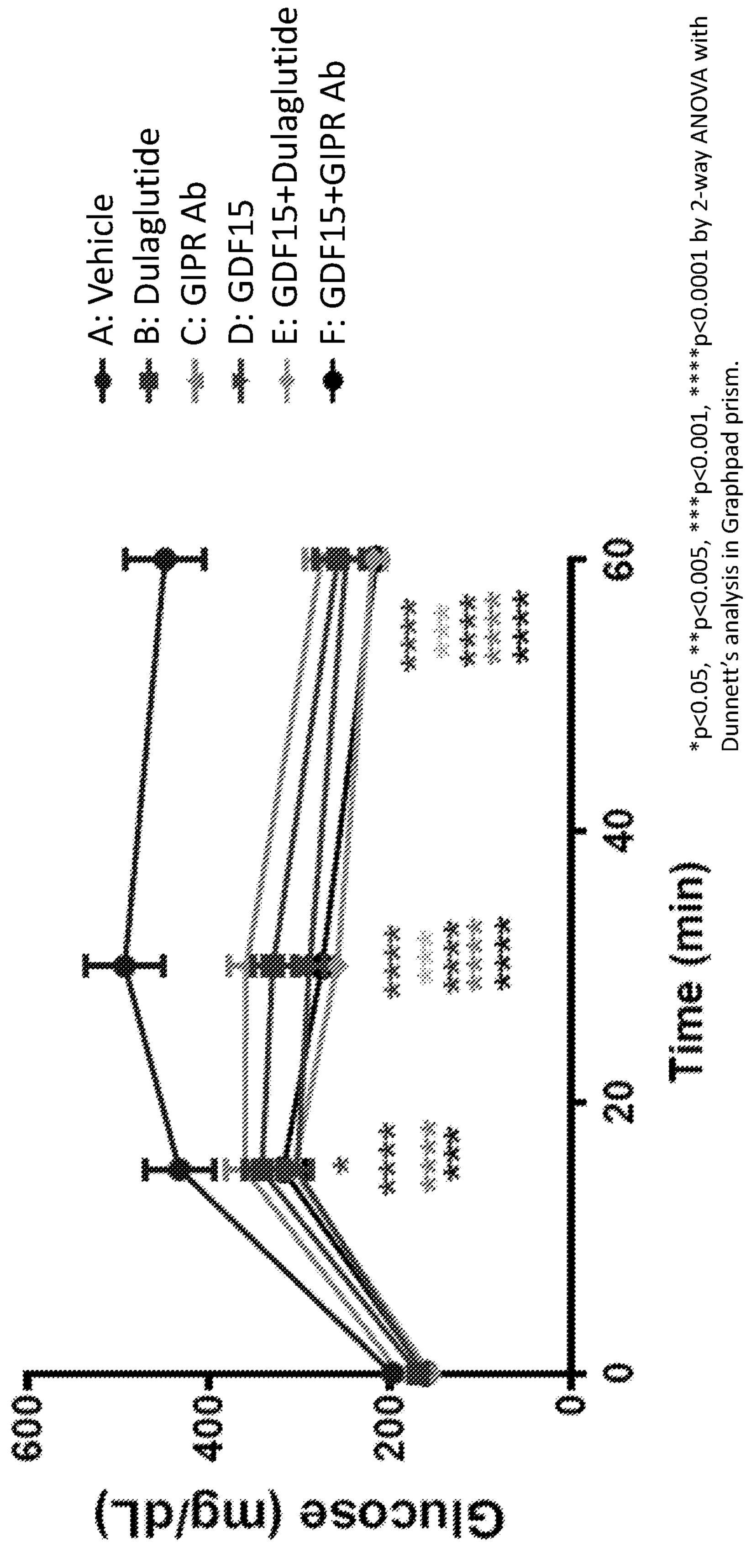
FIG. 4A shows the glucose levels from the intraperitoneal glucose tolerance test (IPGTT) of the mice in Groups A-F five weeks after treatment.
Figure 4B:
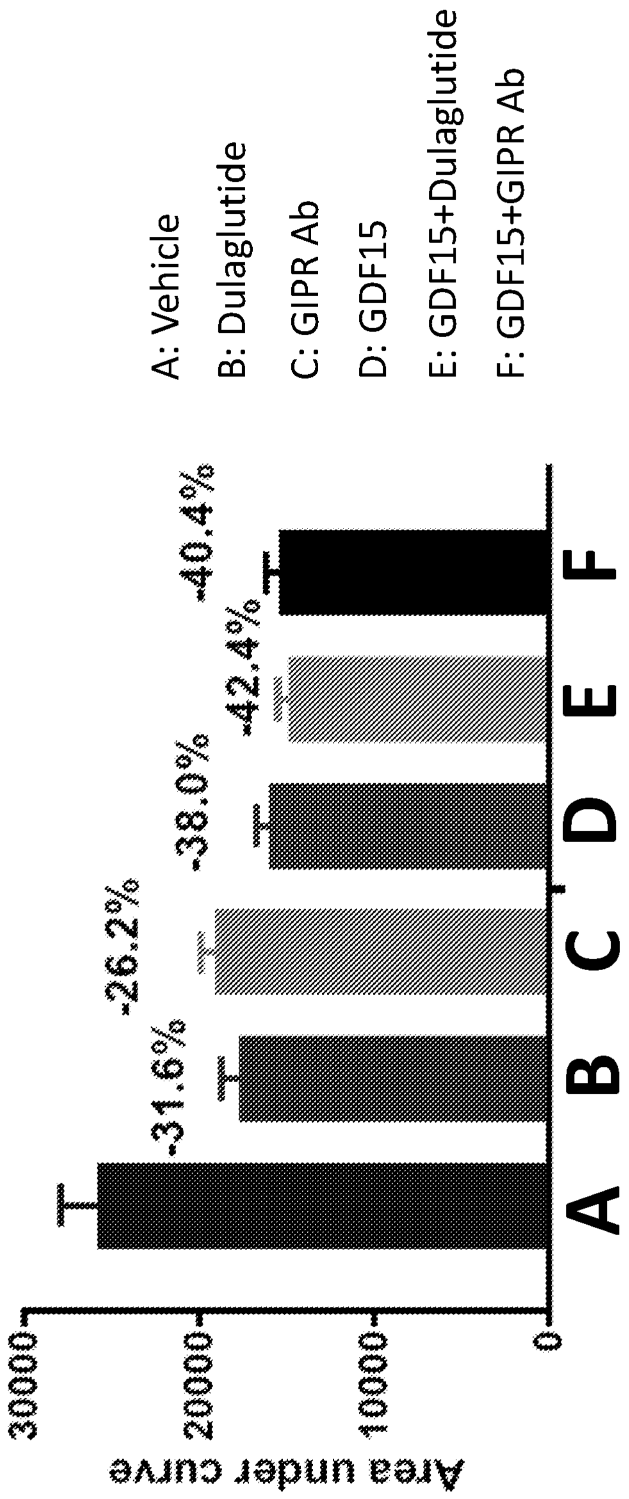
FIG. 4B shows the glucose AUC results from the IPGTT of the mice in Groups A-F five weeks after treatment.

Similarly, combination therapy did not have a greater effect than GDF15 monotherapy in an intraperitoneal glucose tolerance test (IPGTT). An IPGTT was conducted 5 weeks after first treatment and FIG. 4 shows the glucose levels (FIG. 4A) and glucose AUC (FIG. 4B) of the IPGTT test 5 weeks after treatment started, with the AUC differences between treatment groups and vehicle group labeled on top of each bar in FIG. 4B. The combination therapy groups, Groups E and F, had a −42.4% AUC and −40.4% AUC, respectively, as compared to the GDF15 monotherapy group, Group D, with −38.0% AUC.

Figure 5A:
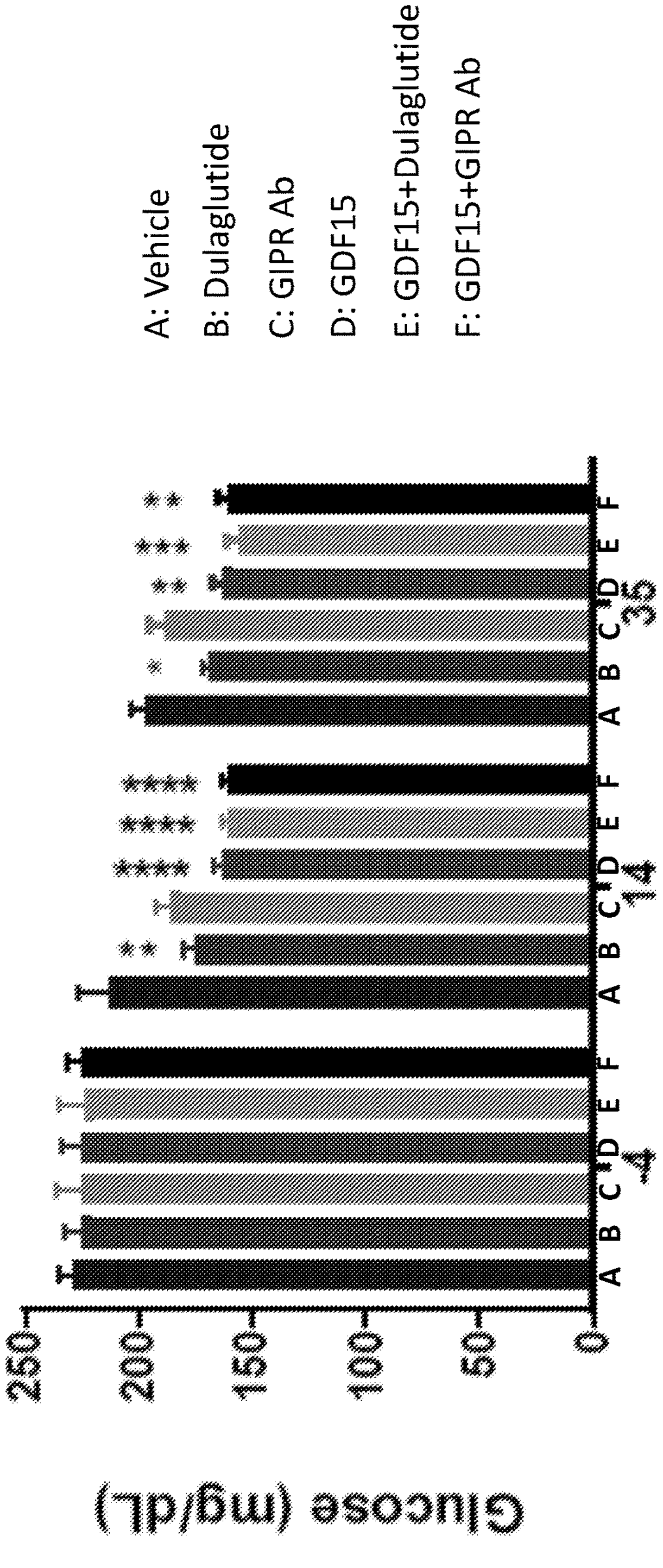
FIG. 5A shows the fasting blood glucose levels measured two weeks and five weeks after treatment of the mice in Groups A-F.
Figure 5B:
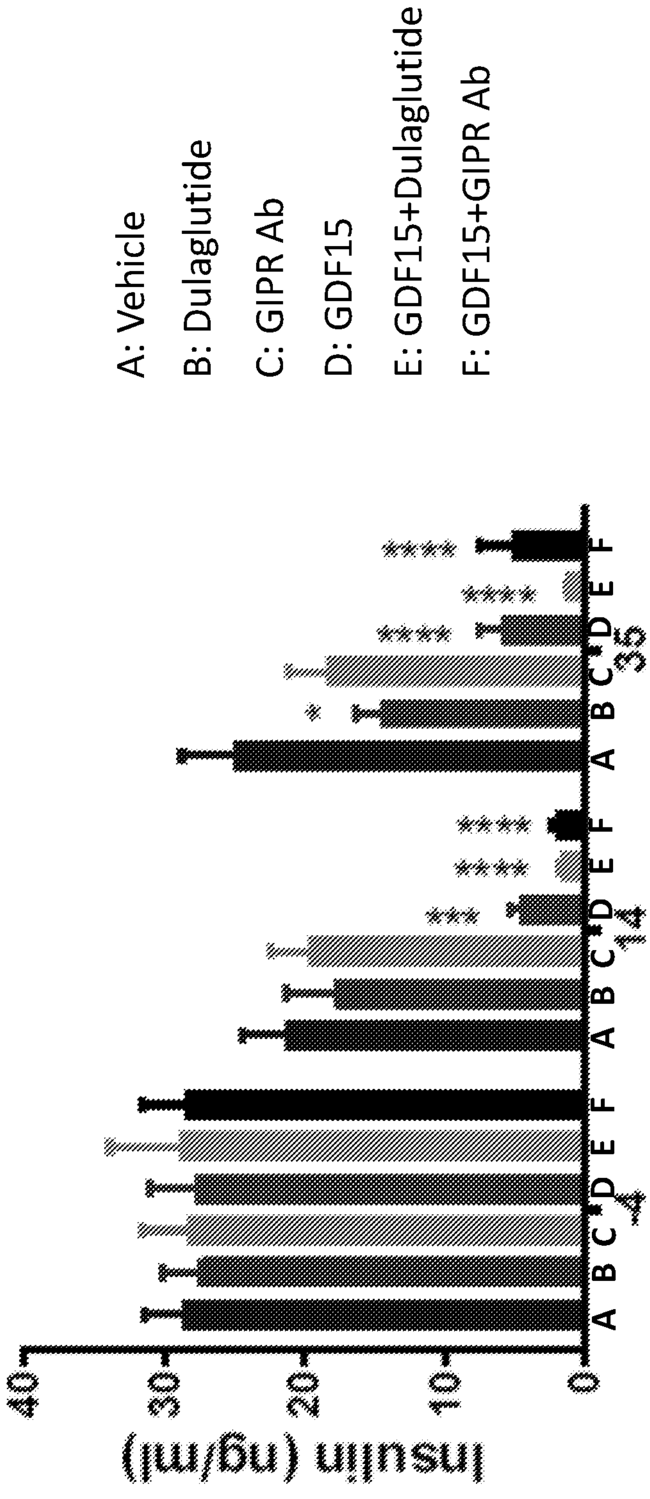
FIG. 5B shows the serum insulin levels measured two weeks and five weeks after treatment of the mice in Groups A-F.
Figure 5C:
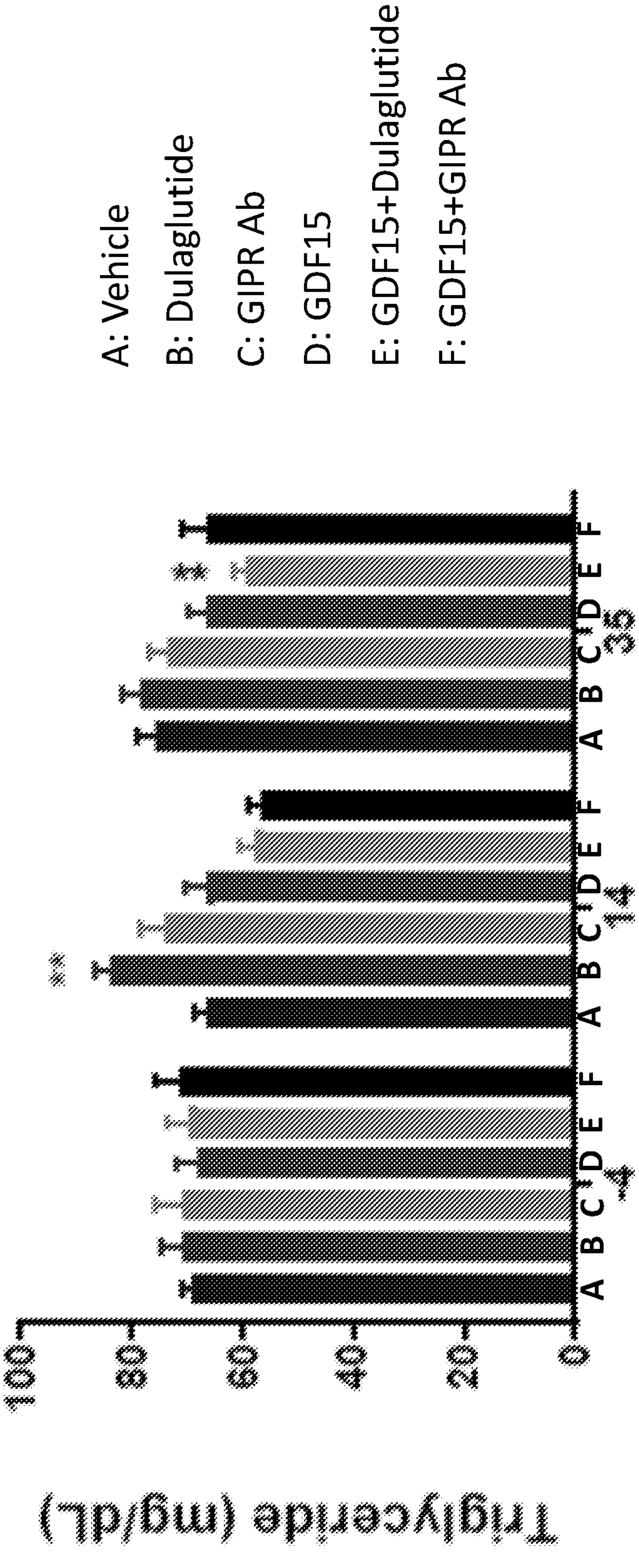
FIG. 5C shows the serum triglyceride levels measured two weeks and five weeks after treatment of the mice m Groups A-F.
Figure 5D:
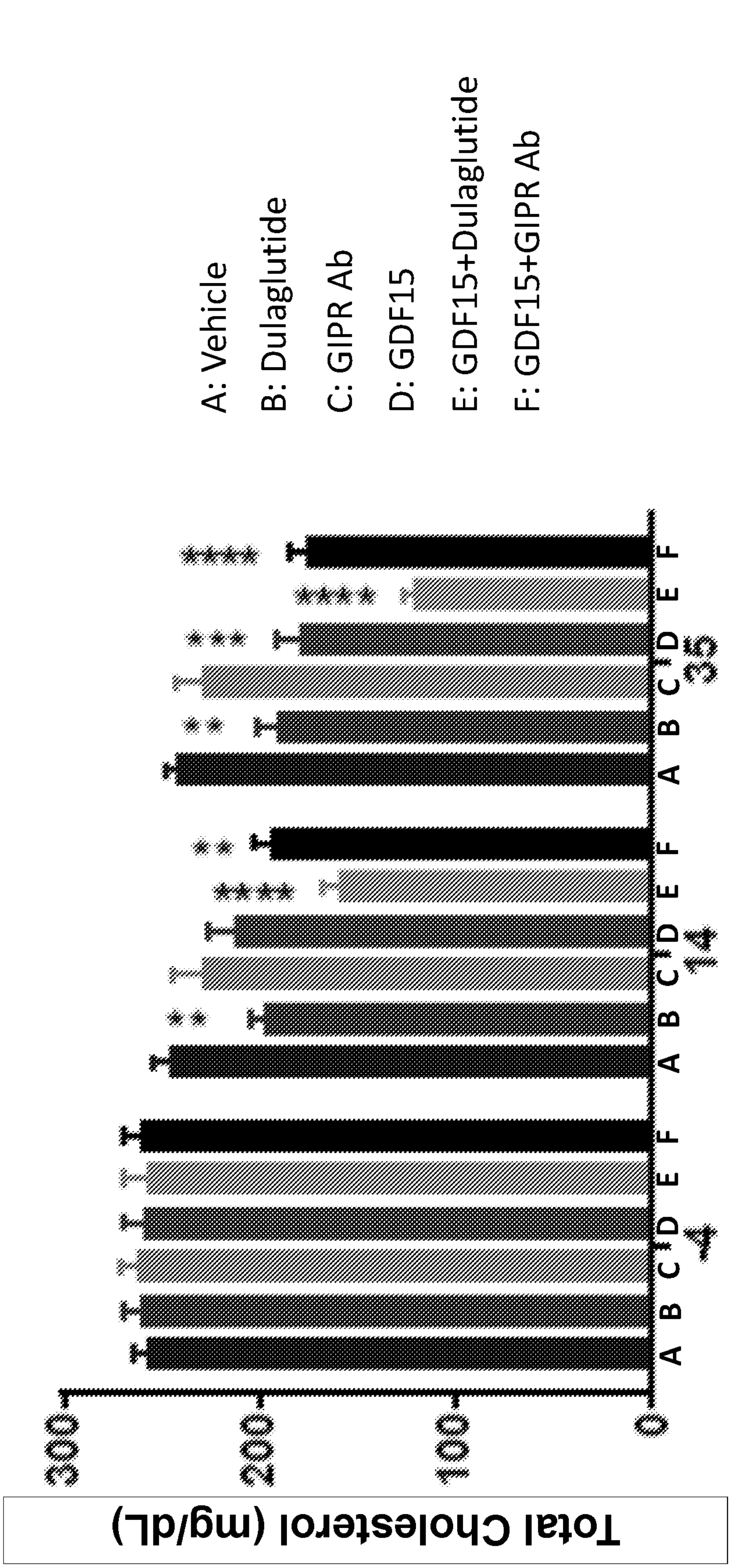
FIG. 5D shows the serum total cholesterol levels measured two weeks and weeks after treatment of the mice in Groups A-F.

Fasting blood glucose, serum insulin, serum triglyceride and serum total cholesterol levels were measured 2 weeks and 5 weeks after first treatment (FIGS. 5A-5D, respectively). Combination therapy (Groups E and F) did not have a greater effect in reducing fasting blood glucose levels or triglyceride levels than GDF15 monotherapy (Group D) (FIGS. 5A and 5C, respectively), but at two weeks, combination therapy did have a greater effect than GDF15 monotherapy in reducing serum insulin levels, and at five weeks, the combination of GDF15+Dulaglutide had a greater effect in reducing serum insulin levels than GDF15 monotherapy (FIG. 5B). The combination of GDF15+Dulaglutide also had a greater effect than GDF15 monotherapy in reducing the total cholesterol level (FIG. 5D).

Figure 6:
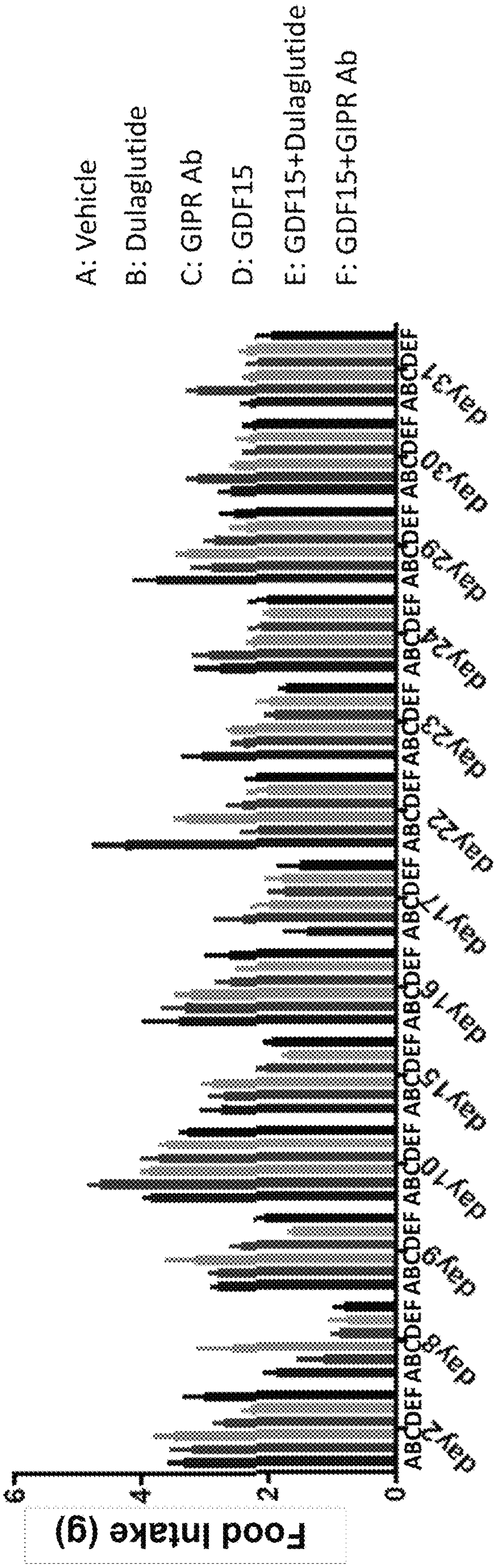
FIG. 6 shows the daily food intake measured three consecutive days a week during the treatment of the mice in Groups A-F.

Food intake was measured three consecutive days per week and the results are shown in FIG. 6. The significance of the data is shown in Table 8.

TABLE 8

Significance of Food Intake Assay

| Group | D2 | D8 | D9 | D10 | D15 | D16 | D17 | D22 | D23 | D24 | D29 | D30 | D31 |
|---|---|---|---|---|---|---|---|---|---|---|---|---|---|
| A | — | — | — | — | — | — | — | — | — | — | — | — | — |
| B | ns | ns | ns | ns | ns | ns | * | **** | ns | ns | ns | ns | ns |
| C | ns | ns | ns | ns | ns | ns | ns | * | ns | ns | ns | ns | ns |
| D | ns | * | ns | ns | ns | ns | ns | **** | ** | ns | * | ns | ns |
| E | * | * | * | ns | ** | ** | ns | **** | ** | ns | *** | ns | ns |
| F | ns | * | ns | ns | ns | ns | ns | **** | *** | ns | ** | ns | ns |

ns: not significant;
*p < 0.05, p < 0.005, *p < 0.001, ****p < 0.0001 by 2-way ANOVA with Dunnett's analysis in Graphpad prism.

While the present invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this application are expressly incorporated by reference herein for any purpose.

What is claimed is:

1. A method of decreasing body weight in a subject comprising administering a growth differentiation factor 15 (GDF15) molecule and a glucose-dependent insulinotropic polypeptide receptor (GIPR) antagonist to the subject, wherein:

the GDF15 molecule is a fusion protein comprising a GDF15 region joined to an Fc region, wherein the GDF15 region comprises an amino acid sequence selected from SEQ ID NOs: 6 and 13-18 and the Fc region comprises an amino acid sequence selected from SEQ ID NOs: 26-37; and the GIPR antagonist is a GIPR antigen-binding protein that comprises a light chain and a heavy chain comprising the amino acid sequences of SEQ ID NOs: 97 and 98; 99 and 100; 101 and 102; 103 and 104; or 105 and 106, respectively, and further wherein the GDF15 molecule and the GIPR antagonist are administered to the subject at a molar ratio in the range of 1:1 to 1:50.

2. The method of claim 1, wherein the GDF15 molecule and the GIPR antagonist are administered concurrently.

3. The method of claim 1, wherein the GDF15 molecule and the GIPR antagonist are administered sequentially.

4. The method of claim 1, wherein the GIPR antagonist is an antibody.

5. The method of claim 1, wherein the GDF15 region is joined to the Fc region via a linker.

6. The method of claim 5, wherein the linker is a (G4S) n or (G4Q) n linker, wherein n is greater than 0.

7. The method of claim 5, wherein the linker comprises an amino acid sequence selected from SEQ ID NOs: 19-25 and 107.

8. The method of claim 5, wherein the linker comprises the amino acid sequence of SEQ ID NO: 25.

9. The method of claim 1, wherein the GDF15 molecule comprises an amino acid sequence selected from SEQ ID NOs: 39-57.

10. The method of claim 1, wherein the GDF15 molecule comprises the amino acid sequence of SEQ ID NO: 39.

11. The method of claim 1, wherein administration of the GDF15 molecule and the GIPR antagonist has a greater than 1.4-fold effect on body weight relative to GDF15 monotherapy 35 days after administration.

12. The method of claim 1, wherein the molar ratio of the GDF15 molecule to the GIPR antagonist is in the range of 1:1 to 1:40.

* * * * *